(12) United States Patent
Conte et al.

(10) Patent No.: US 7,795,247 B2
(45) Date of Patent: Sep. 14, 2010

(54) TETRACYCLIC INDOLE DERIVATIVES AS ANTIVIRAL AGENTS

(75) Inventors: Immacolata Conte, Rome (IT); Caterina Ercolani, Rome (IT); Frank Narjes, Rome (IT); Marco Pompei, Rome (IT); Michael Rowley, Rome (IT); Ian Stansfield, Rome (IT)

(73) Assignee: Istituto di Ricerche di Biologia Molecolare P. Angeletti SpA, Pomezia (Rome) (IT)

( * ) Notice: Subject to any disclaimer, the term of this patent is extended or adjusted under 35 U.S.C. 154(b) by 47 days.

(21) Appl. No.: 11/258,445

(22) Filed: Oct. 25, 2005

(65) Prior Publication Data

US 2006/0100262 A1 May 11, 2006

Related U.S. Application Data

(60) Provisional application No. 60/659,951, filed on Mar. 9, 2005.

(30) Foreign Application Priority Data

Oct. 26, 2004 (GB) .................................. 0423767.3
Jun. 21, 2005 (GB) .................................. 0512519.0

(51) Int. Cl.
*A61K 31/353* (2006.01)
*A61K 31/554* (2006.01)
*C07D 487/00* (2006.01)
*C07D 491/00* (2006.01)
*C07D 513/00* (2006.01)

(52) U.S. Cl. .................................. 514/211.09; 540/468
(58) Field of Classification Search ........................ None
See application file for complete search history.

(56) References Cited

U.S. PATENT DOCUMENTS

| | | | |
|---|---|---|---|
| 5,206,382 A | 4/1993 | Costa et al. | |
| 7,153,848 B2 | 12/2006 | Hudyma et al. | |
| 2005/0239767 A1 | 10/2005 | Chan et al. | |
| 2007/0049593 A1* | 3/2007 | Oka et al. | .................. 514/243 |

FOREIGN PATENT DOCUMENTS

| | | | |
|---|---|---|---|
| EP | 1 719 773 A1 | 11/2006 | |
| EP | 1719773 A1 | 11/2006 | |
| WO | WO 93/00334 A1 | 1/1993 | |
| WO | WO/02059321 | 8/2002 | |
| WO | WO 03/099824 A1 | 12/2003 | |
| WO | WO 2004/065367 A1 | 8/2004 | |
| WO | WO 2004/087714 A1 | 10/2004 | |
| WO | WO 2005/080399 A1 | 9/2005 | |
| WO | WO2006/020082 A1 | 2/2006 | |
| WO | WO2006/046030 | 5/2006 | |
| WO | WO 2007/033032 A1 | 3/2007 | |
| WO | WO 2007/033175 A1 | 3/2007 | |

OTHER PUBLICATIONS

Bahadur et al. Journal of the Chemical Society, Perkin Transactions 1: Organic and Bio-organic, 1980, 12, 2870-77.*
"Prophylactic treatment from online medical dictionary", http://cancerweb.ncl.ac.uk/cgi-bin/omd?prophylactic+treatment, accessed May 7, 2007.*
Vlakhakis, Stacey. Lebanese Medical Journal, 2006, 54 (2), 106-110.*
Asselah et al. Gut, 2006, 55, 123-130.*
Padwa et al. Journal of the American Chemical Society, 1992, 114, 593-601.*
Goudreau et al. Expert Opinion on Investigational Drugs, 2005, 14(9), 1129-44.*
Randall, Journal of Pediatric Oncology Nursing, 2001, 18(1), 4-15. (abstract only).*
Koev et al. Expert Opinion on Investigational Drugs, 2008, 17(3), 303-19.*
U.S. Appl. No. 11/666,583, (unpublished), Caterina Ercolani et al.
Lohman et al.. "Replication of Subgenomic Hepatitis C Virus RNAs in a Hepatoma Cell Line", Science, vol. 285, pp. 110-113 (1999).
Still et al. "Rapid Chromatographic Technique for Preparative Separations with Moderate Resolution", Journal of OrganicChemistry, vol. 43, No. 14, pp. 2923-2925 (1978).
Szmynifka et al. "The Synthesis and Reactions of 4-Carbomethoxy Beta-Sultams", Tetrahedron Letters, vol. 30 No. 22, pp. 2869-2872 (1989).

* cited by examiner

*Primary Examiner*—James O Wilson
*Assistant Examiner*—Noble Jarrell
(74) *Attorney, Agent, or Firm*—Julie M. Lake; Kenneth R. Walton; Sheldon O. Heber

(57) ABSTRACT

The present invention relates to tetracyclic indole compounds of formula (I):

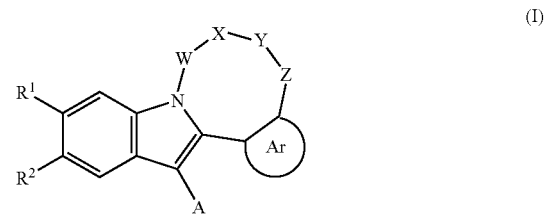

wherein $R^1$, $R^2$, A, Ar, W, X, Y and Z are defined herein, and pharmaceutically acceptable salts thereof, pharmaceutical compositions comprising them, and their use for the treatment or prevention of infection by hepatitis C virus.

31 Claims, No Drawings

TETRACYCLIC INDOLE DERIVATIVES AS ANTIVIRAL AGENTS

This application claims the benefit of United Kingdom Application Nos. 0423767.3 (filed Oct. 26, 2004) and 0512519.0 (filed Jun. 21, 2005) and U.S. Provisional Application No. 60/659,951 (filed Mar. 9, 2005).

The present invention relates to tetracyclic indole compounds, to pharmaceutical compositions containing them, to their use in the prevention and treatment of hepatitis C infections and to methods of preparation of such compounds and compositions.

Hepatitis C (HCV) is a cause of viral infections. There is as yet no adequate treatment for HCV infection but it is believed that inhibition of its RNA polymerase in mammals, particularly humans, would be of benefit.

Published International patent application WO 93/00334 (Fidia-Georgetown Institute for the Neurosciences) discloses the following indole derivatives:

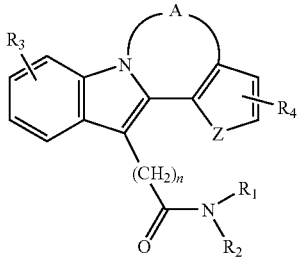

where A, Z, $R_1$, $R_2$, $R_3$, $R_4$ and n are defined therein, as useful in compositions and methods for treating psychiatric and neurological disorders. However, this document does not disclose the use of tetracyclic indole derivatives in treating or preventing viral infections.

Published International patent application WO 2005/080399 (Japan Tobacco Inc.) discloses the following fused heterotetracyclic compounds:

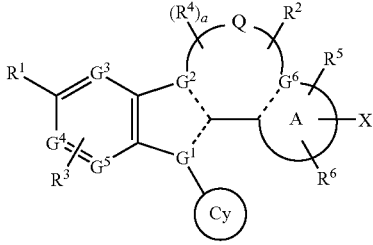

where A, X, Cy, $G^1$, $G^2$, $G^3$, $G^4$, $G^5$, $G^6$, $R^1$, $R^2$, $R^3$, $R^4$, $R^5$, $R^6$ and a are defined therein, and their use as HCV polymerase inhibitors.

The present invention provides the compound of the formula (I):

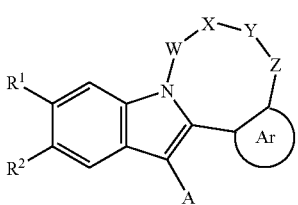

(I)

wherein

A is $C_{3-8}$cycloalkyl, optionally substituted by halogen, hydroxy, $C_{1-4}$alkyl or $C_{1-4}$alkoxy;

Ar is a moiety containing at least one aromatic ring and possesses 5, 6, 9 or 10 ring atoms, optionally containing 1, 2 or 3 heteroatoms independently selected from N, O and S, such as phenyl, pyridyl, pyridazinyl, pyrimidinyl, pyrazinyl, thienyl, furanyl, pyrazolyl and imidazolyl, which ring is optionally substituted by groups $Q^1$ and $Q^2$;

$Q^1$ is halogen, hydroxy, $C_{1-6}$alkyl, $C_{1-6}$alkoxy, $(CH_2)_{0-3}$aryl, heteroaryl, $CONR^cR^d$, $(CH_2)_{0-3}NR^cR^d$, $O(CH_2)_{0-3}$ $C_{3-8}$cycloalkyl, $O(CH_2)_{1-3}NR^cR^d$, $O(CH_2)_{0-3}CONR^cR^d$, $O(CH_2)_{0-3}CO_2H$, $O(CH_2)_{0-3}$aryl, $O(CH_2)_{0-3}$heteroaryl, $OCHR^eR^f$ or $O(CH_2)_{0-3}S(O)_2(CH_2)_{0-3}NR^cR^d$;

$R^c$ and $R^d$ are independently selected from hydrogen, $C_{1-6}$alkyl and $C(O)C_{1-6}$alkyl;

or $R^c$ and $R^d$, together with the nitrogen atom to which they are attached, form a heteroaliphatic ring of 4 to 7 ring atoms, optionally containing 1 or 2 more heteroatoms independently selected from O and S and/or 1 or 2 groups independently selected from NH and $NC_{1-4}$alkyl, where said ring is optionally substituted by halogen, hydroxy, $C_{1-4}$alkyl or $C_{1-4}$alkoxy;

$R^e$ and $R^f$ are independently selected from hydrogen, $C_{1-4}$alkyl and $C_{1-4}$alkoxy;

or $R^e$ and $R^f$ are linked by a heteroatom selected from N, O and S to form a heteroaliphatic ring of 4 to 7 ring atoms, where said ring is optionally substituted by halogen, hydroxy, $C_{1-4}$alkyl or $C_{1-4}$alkoxy;

and where said $C_{1-4}$alkyl, $C_{1-4}$alkoxy and aryl groups are optionally substituted by halogen or hydroxy;

$Q^2$ is halogen, hydroxy, $C_{1-4}$alkyl or $C_{1-4}$alkoxy, where said $C_{1-4}$alkyl and $C_{1-4}$alkoxy groups are optionally substituted by halogen or hydroxy;

or $Q^1$ and $Q^2$ may be linked to form a ring of 4 to 7 atoms, where said ring optionally contains 1 or 2 heteroatoms independently selected from N, O and S, and is optionally substituted by halogen, hydroxy, $C_{1-4}$alkyl or $C_{1-4}$alkoxy;

one of $R^1$ and $R^2$ is $CO_2H$, $C(O)NHS(O)_2NR^aR^b$, $C(O)NHS(O)_2C_{1-6}$alkyl, $C(O)NHS(O)_2(CH_2)_{0-3}CO_2R^c$ or $C(O)NHS(O)_2(CH_2)_{0-3}$aryl, and the other of $R^1$ and $R^2$ is hydrogen;

$R^a$ and $R^b$ are independently selected from hydrogen and $C_{1-6}$alkyl, or $R^a$ and $R^b$, together with the nitrogen atom to which they are attached, form a heteroaliphatic ring of 4 to 7 ring atoms, which ring may optionally contain 1 or 2 more heteroatoms independently selected from O and S and/or 1 or 2 groups independently selected from $S(O)$, $S(O)_2$, NH and $NC_{1-4}$ alkyl;

W is $—CH_2—$ or $—CH_2CH_2—$;

X is C=O, $—CR^{14}R^{15}—$ or $NR^{14}$;

Y is $—CR^{14a}R^{15a}—$ or $NR^{14a}$;

Z is O, $—CHR^{10}—$ or $—CHR^{10}CH_2—$;

$R^{10}$ is hydrogen, hydroxy, $C_{1-6}$alkyl, $C_{2-6}$alkenyl, oxo, $O(CH_2)_{1-3}NR^cR^d$ or $N(CH_2)_{1-3}NR^cR^d$;

$R^{14}$, $R^{14a}$, $R^{15}$ and $R^{15a}$ are each independently selected from hydrogen, hydroxy, $C_{1-6}$alkyl, $C_{2-6}$alkenyl, $C_{2-6}$alkynyl, $(CH_2)_{0-3}C_{3-8}$cycloalkyl, $C_{1-6}$alkoxy, $C(O)C_{1-6}$alkyl, $(CH_2)_{0-3}$aryl, $(CH_2)_{0-3}$Het, $C(O)(CH_2)_{0-3}$Het, $(CH_2)_{0-3}$ $NR^{16}R^{17}$, $(CH_2)_{0-3}OR^{16}$, $(CH_2)_{0-3}C(O)(CH_2)_{0-3}NR^{16}R^{17}$, $NR^{18}C(O)(CH_2)_{0-3}NR^{16}R^{17}$, $S(O)_{0-2}(CH_2)_{0-3}NR^{16}R^{17}$, $(CH_2)_{0-3}$heteroaryl or $C(O)(CH_2)_{0-3}$heteroaryl, optionally substituted by one or two groups independently selected from $C_{1-6}$alkyl, hydroxy, halogen, $C_{1-6}$alkoxy, SH and $S(C_{1-6}$alkyl);

$R^{16}$ and $R^{17}$ are independently selected from hydrogen, $C_{1-6}$alkyl, $(CH_2)_{0-4}NR^{18}R^{19}$, $(CH_2)_{0-3}$Het, $(CH_2)_{0-3}$heteroaryl, $(CH_2)_{0-3}C(O)(CH_2)_{0-3}NR^{18}R^{19}$ or $(CH_2)_{0-3}C_{3-8}$cycloalkyl, optionally substituted by $C_{1-6}$alkyl, $(CH_2)_{0-3}OH$ or $(CH_2)_{0-3}C_{1-6}$alkoxy;

or $R^{16}$ and $R^{17}$, together with the nitrogen atom to which they are attached, form a heteroaliphatic ring of 4 to 7 ring atoms, which ring may optionally contain 1 or 2 more heteroatoms selected from O and S and/or 1 or 2 groups independently selected from $S(O)$, $S(O)_2$, NH, $NC_{1-4}$alkyl and $N(CH_2)_{0-3}C_{1-4}$alkoxy, and which ring is optionally substituted by halogen, hydroxy, $C_{1-4}$alkyl or $C_{1-4}$alkoxy;

$R^{18}$ and $R^{19}$ are independently selected from hydrogen, $C_{1-6}$alkyl and heteroaryl;

or $R^{18}$ and $R^{19}$, together with the nitrogen atom to which they are attached, form a heteroaliphatic ring of 4 to 7 ring atoms, which ring may optionally contain 1 or 2 more heteroatoms selected from O and S and/or 1 or 2 groups selected from $S(O)$, $S(O)_2$, NH and $NC_{1-4}$alkyl, and which ring is optionally substituted by halogen, hydroxy, $C_{1-4}$alkyl or $C_{1-4}$alkoxy;

and pharmaceutically acceptable salts thereof;

with the proviso that the compound of formula (I) is not:
14-cyclohexyl-7,8-dihydro-6H-indolo[1,2-e][1,5]benzoxazine-11-carboxylic acid,
14-cyclohexyl-6-methyl-5,6,7,8-tetrahydroindolo[2,1-a][2,5]benzodiazocine-11-carboxylic acid,
14-cyclohexyl-3-methoxy-5,6,7,8-tetrahydroindolo[2,1-a][2,5]benzodiazocine-11-carboxylic acid, or
14-cyclohexyl-3-methoxy-6-methyl-5,6,7,8-tetrahydroindolo[2,1-a][2,5]benzodiazocine-11-carboxylic acid.

In one embodiment, X is —$CR^{14}R^{15}$— and Y is $NR^{14a}$.

In another embodiment, Y is —$CR^{14a}R^{15a}$— and X is $NR^{14}$.

One favoured group of compounds of the present invention is of formula (Ii) and pharmaceutically acceptable salts thereof:

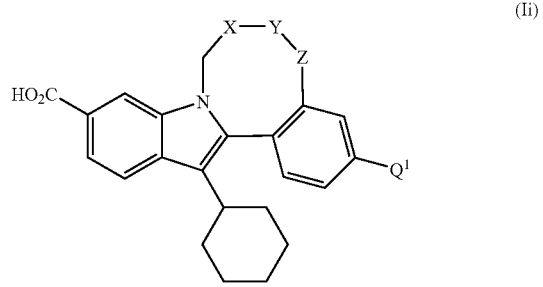

(Ii)

where
X is —$CHR^{14}$—;
Y is —$CH_2$— or $NR^{14a}$;
Z is O or —$CH_2$—;
$Q^1$, $R^{14}$ and $R^{14a}$ are as defined in relation to formula (I);

with the proviso that when Y is $NR^{14}$, Z is not O.

The following embodiments apply in relation to the compounds of formulae (I) and (Ii):

In one embodiment, Y is —$CH_2$— when Z is O.

In another embodiment, Y is $NR^{14a}$ when Z is —$CH_2$—.

In another embodiment, Y is $NR^{14a}$ when X is —$CH_2$—.

In another embodiment, Y is —$CH_2$— when $R^{14}$ is other than hydrogen.

In another embodiment, $R^{14}$ is $(CH_2)_{0-1}OR^{16}$ or $(CH_2)_{0-1}NR^{16}R^{17}$ where $R^{16}$ and $R^{17}$ are as defined in relation to formula (I). Preferably, $R^{14}$ is $OR^{16}$ or $NR^{16}R^{17}$.

When $R^{14}$ is $OR^{16}$, preferably $R^{16}$ is hydrogen, $(CH_2)_{1-3}(C_{1-6}$alkoxy) or $(CH_2)_{1-3}NR^{18}R^{19}$ where $R^{18}$ and $R^{19}$ are as defined in relation to formula (I). More preferably, $R^{16}$ is hydrogen, $(CH_2)_{2-3}(C_{1-4}$alkoxy), $(CH_2)_{2-3}N(C_{1-4}$alkyl$)_2$ or $(CH_2)_{2-3}NR^{18}R^{19}$ where $R^{18}$ and $R^{19}$, together with the nitrogen atom to which they are attached, form a 5- or 6-membered heteroaliphatic ring, which ring may optionally contain 1 or 2 more heteroatoms selected from O and S and/or 1 or 2 groups selected from $S(O)$, $S(O)_2$, NH and $NC_{1-4}$alkyl. Examples of suitable $R^{16}$ groups include hydrogen,

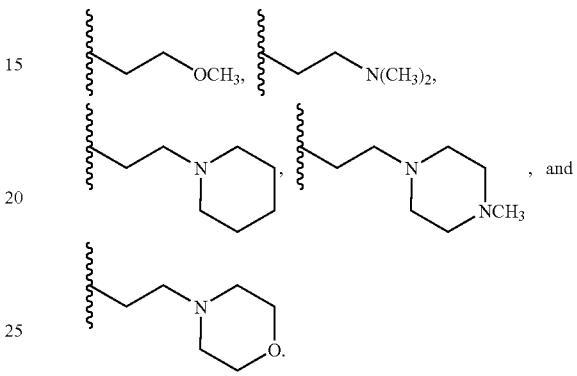

When $R^{14}$ is $NR^{16}R^{17}$, preferably $R^{16}$ is hydrogen, $C_{1-4}$alkyl, $C_{3-8}$cycloalkyl, $(CH_2)_{1-3}NR^{18}R^{19}$, $(CH_2)_{0-3}C_{1-4}$alkoxy, $(CH_2)_{0-2}C(O)(CH_2)_{0-2}N(C_{1-4}$alkyl$)_2$ or Het, optionally substituted by $C_{1-4}$alkyl, where $R^{18}$ and $R^{19}$ are independently selected from hydrogen, $C_{1-4}$alkyl and heteroaryl, or $R^{18}$ and $R^{19}$, together with the nitrogen atom to which they are attached, form a 5- or 6-membered heteroaliphatic ring, which ring may optionally contain 1 or 2 more heteroatoms selected from O and S and/or 1 or 2 groups selected from $S(O)$, $S(O)_2$, NH and $NC_{1-4}$alkyl.

When $R^{14}$ is $NR^{16}R^{17}$, preferably, $R^{17}$ is hydrogen or $C_{1-6}$alkyl. More preferably, $R^{17}$ is hydrogen, methyl, ethyl or i-propyl.

Alternatively, when $R^{14}$ is $NR^{16}R^{17}$, $R^{16}$ and $R^{17}$, together with the nitrogen atom to which they are attached, form a 5- or 6-membered heteroaliphatic ring, which ring may optionally contain 1 or 2 more O atoms and/or 1 or 2 groups selected from NH, $NC_{1-4}$alkyl and $N(CH_2)_{0-3}C_{1-4}$alkoxy. Examples of suitable $NR^{16}R^{17}$ groups include:

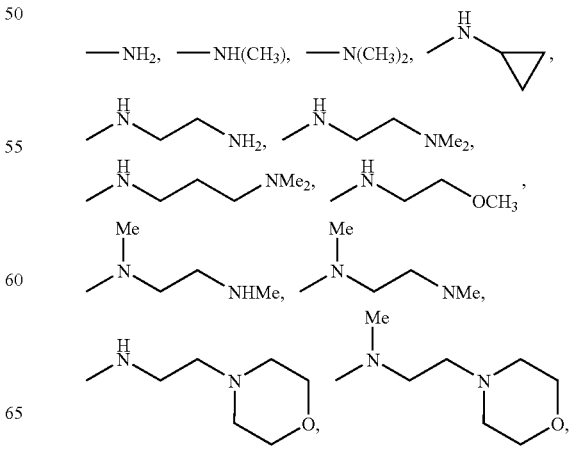

-continued

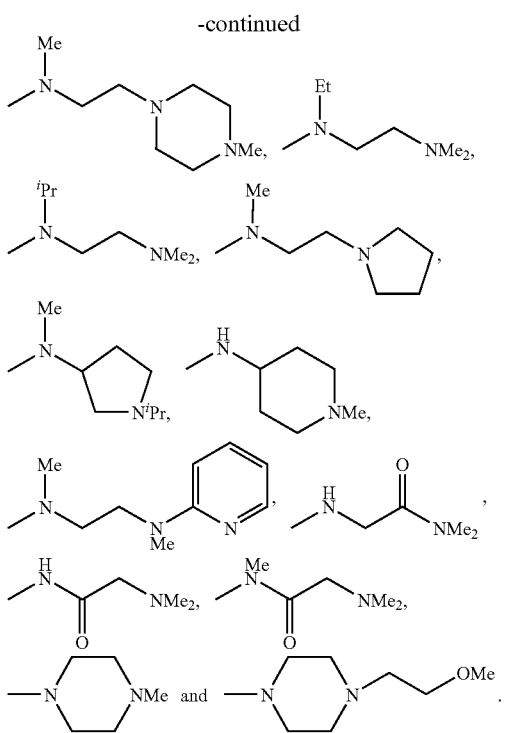

In another embodiment, $R^{14a}$ is hydrogen, $C_{1-6}$alkyl, $C_{2-6}$alkenyl, Het, $(CH_2)_{0-3}NR^{16}R^{17}$ or $C(O)(CH_2)_{0-3}NR^{16}R^{17}$, where $R^{16}$ and $R^{17}$ are as defined in relation to formula (I). Preferably, $R^{14a}$ is hydrogen, $C_{1-5}$alkyl, $C_{2-4}$alkenyl, Het, $(CH_2)_2NR^{16}R^{17}$ or $C(O)(CH_2)_{1-2}NR^{16}R^{17}$, where $R^{16}$ and $R^{17}$ are independently $C_{1-6}$alkyl, or $R^{16}$ and $R^{17}$, together with the nitrogen atom to which they are attached, form a 5- or 6-membered heteroaliphatic ring, which ring may optionally contain 1 or 2 more O atoms and/or 1 or 2 groups selected from NH and $NC_{1-4}$alkyl. Examples of suitable $R^{14a}$ groups include hydrogen, methyl, ethyl, propyl, butyl, pentyl, allyl,

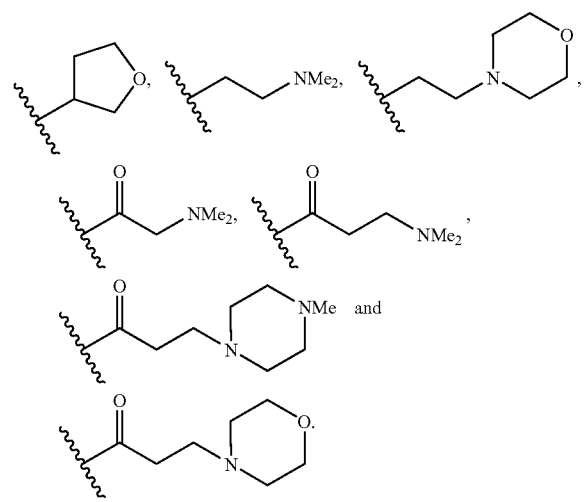

In another embodiment, $Q^1$ is hydrogen, halogen, hydroxy, $C_{1-6}$alkoxy, $O(CH_2)_{0-3}C(O)(CH_2)_{0-3}N(C_{1-4}alkyl)_2$, $O(CH_2)_{0-3}$aryl or $O(CH_2)_{0-3}$heteroaryl. Preferably, $Q^1$ is hydrogen, fluorine, chlorine, hydroxy, $C_{1-4}$alkoxy, $O(CH_2)_{0-3}C(O)N(C_{1-4}alkyl)_2$, $O(CH_2)_{0-1}$aryl or $O(CH_2)_{0-1}$heteroaryl. More preferably, $Q^1$ is hydrogen, fluorine, chlorine, hydroxy, $C_{1-3}$alkoxy, $O(CH_2)_{1-2}C(O)N(C_{1-3}alkyl)_2$, $O(CH_2)_{0-1}$phenyl, $O(CH_2)_{0-1}$pyridyl, $O(CH_2)_{0-1}$pyridazinyl, $O(CH_2)_{0-1}$pyrimidinyl or $O(CH_2)_{0-1}$pyrazinyl. Most preferably, $Q^1$ is hydrogen, fluorine, chlorine, hydroxy, methoxy, ethoxy, i-propoxy, $OCH_2C(O)N(CH_3)_2$, benzyloxy, O-pyridinyl, $OCH_2$pyridinyl, $OCH_2$pyridazinyl, $OCH_2$pyrimidinyl or O-pyrazinyl.

Another favoured group of compounds of the present invention is the compound of formula (Ia):

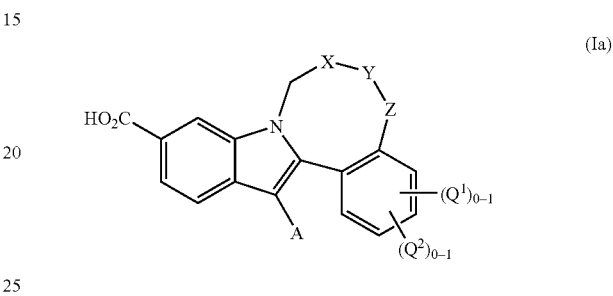

(Ia)

wherein

A is cyclopentyl or cyclohexyl, optionally substituted by halogen, hydroxy, $C_{1-4}$alkyl or $C_{1-4}$alkoxy;

$Q^1$ is halogen, hydroxy, $C_{1-6}$alkyl, $C_{1-6}$alkoxy, aryl, heteroaryl, $CONR^cR^d$, $(CH_2)_{0-3}NR^cR^d$, $O(CH_2)_{1-3}NR^cR^d$, $O(CH_2)_{0-3}CONR^cR^d$, $O(CH_2)_{0-3}$aryl, $O(CH_2)_{0-3}$heteroaryl, $OCHR^eR^f$;

$R^c$ and $R^d$ are each independently selected from hydrogen, $C_{1-4}$alkyl and $C(O)C_{1-4}$alkyl;

or $R^c$, $R^d$ and the nitrogen atom to which they are attached form a heteroaliphatic ring of 4 to 7 ring atoms, where said ring is optionally substituted by halogen, hydroxy, $C_{1-4}$alkyl or $C_{1-4}$alkoxy;

$R^e$ and $R^f$ are each independently selected from hydrogen and $C_{1-4}$alkoxy;

or $R^e$ and $R^f$ are linked by a heteroatom selected from N, O and S to form a heteroaliphatic ring of 4 to 7 ring atoms, where said ring is optionally substituted by halogen, hydroxy, $C_{1-4}$alkyl or $C_{1-4}$alkoxy;

and wherein said $C_{1-4}$alkyl, $C_{1-4}$alkoxy and aryl groups are optionally substituted by halogen or hydroxy;

$Q^2$ is halogen, hydroxy, $C_{1-4}$alkyl or $C_{1-4}$alkoxy, where said $C_{1-4}$alkyl and $C_{1-4}$alkoxy groups are optionally substituted by halogen or hydroxy;

or $Q^1$ and $Q^2$ may be linked by a bond or a heteroatom selected from N, O and S to form a ring of 4 to 7 atoms, where said ring is optionally substituted by halogen, hydroxy, $C_{1-4}$alkyl or $C_{1-4}$alkoxy;

X is C=O, $-CR^{14}R^{15}-$ or $NR^{14}$;

Y is $-CR^{14a}R^{15a}-$ or $NR^{14a}$;

Z is O, $-CH_2-$ or $-CH_2CH_2-$;

$R^{14}$, $R^{14a}$, $R^{15}$ and $R^{15a}$ are each independently selected from hydrogen, hydroxy, $C_{1-6}$alkyl, $C_{2-6}$alkenyl, $C_{1-6}$alkoxy, $C(O)C_{1-6}$alkyl, Het, $(CH_2)_{0-3}NR^{16}R^{17}$, $C(O)(CH_2)_{0-3}NR^{16}R^{17}$ and $NHC(O)(CH_2)_{0-3}NR^{16}R^{17}$;

$R^{16}$ and $R^{17}$ are independently selected from hydrogen, $C_{1-6}$alkyl and $(CH_2)_{0-4}NR^{18}R^{19}$;

or $R^{16}$, $R^{17}$ and the nitrogen atom to which they are attached form a heteroaliphatic ring of 4 to 7 ring atoms, which ring may optionally contain 1 or 2 more heteroatoms selected from O or S or a group S(O), S(O)$_2$, NH or NC$_{1-4}$alkyl, and which ring is optionally substituted by halogen, hydroxy, C$_{1-4}$alkyl or C$_{1-4}$alkoxy;

R$^{18}$ and R$^{19}$ are independently selected from hydrogen and C$_{1-6}$alkyl;

or R$^{18}$, R$^{19}$ and the nitrogen atom to which they are attached form a heteroaliphatic ring of 4 to 7 ring atoms, which ring may optionally contain 1 or 2 more heteroatoms selected from O or S or a group S(O), S(O)$_2$, NH or NC$_{1-4}$alkyl, and which ring is optionally substituted by halogen, hydroxy, C$_{1-4}$alkyl or C$_{1-4}$alkoxy;

and pharmaceutically acceptable salts thereof;

with the proviso that:

when Z is O, then Q$^1$ does not contain a ring that is either a C$_{6-14}$aryl group, a C$_{3-10}$cycloalkyl group, or a heterocyclic group including 1 to 4 heteroatoms selected from O, N and S, and the compound of formula (Ia) is not:

14-cyclohexyl-7,8-dihydro-6H-indolo[1,2-e][1,5]benzoxazine-11-carboxylic acid, 14-cyclohexyl-6-methyl-5,6,7,8-tetrahydroindolo[2,1-a][2,5]benzodiazocine-11-carboxylic acid, 14-cyclohexyl-3-methoxy-5,6,7,8-tetrahydroindolo[2,1-a][2,5]benzodiazocine-11-carboxylic acid, or 14-cyclohexyl-3-methoxy-6-methyl-5,6,7,8-tetrahydroindolo[2,1-a][2,5]benzodiazocine-11-carboxylic acid.

In one embodiment, A is cyclohexyl, optionally substituted by halogen, hydroxy, C$_{1-4}$alkyl or C$_{1-4}$alkoxy. Preferably, A is unsubstituted or substituted by fluorine, chlorine, methyl or methoxy. More preferably, A is unsubstituted.

In another embodiment, Q$^1$ is halogen, hydroxy, C$_{1-4}$alkyl or C$_{1-4}$alkoxy. More preferably, Q$^1$ is fluorine, chlorine, methyl or methoxy.

In another embodiment, Q$^2$ is absent.

Another favoured group of compounds of the present invention is of formula (Iaa) and pharmaceutically acceptable salts thereof:

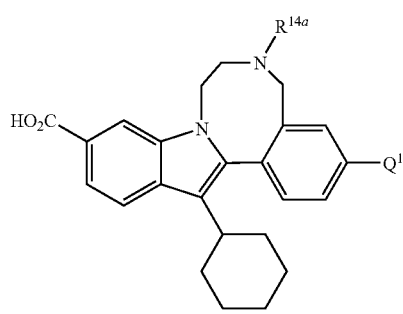

(Iaa)

wherein Q$^1$ and R$^{14a}$ are as defined in relation to formula (Ia)

with the proviso that the compound of formula (Iaa) is not:

14-cyclohexyl-6-methyl-5,6,7,8-tetrahydroindolo[2,1-a][2,5]benzodiazocine-11-carboxylic acid, 14-cyclohexyl-3-methoxy-5,6,7,8-tetrahydroindolo[2,1-a][2,5]benzodiazocine-11-carboxylic acid, or 14-cyclohexyl-3-methoxy-6-methyl-5,6,7,8-tetrahydroindolo[2,1-a][2,5]benzodiazocine-11-carboxylic acid.

In one embodiment, Q$^1$ is halogen or absent. Preferably Q$^1$ is fluorine, chlorine or absent.

In another embodiment, R$^{14a}$ is (CH$_2$)$_{0-3}$NR$^{16}$R$^{17}$ or C(O)(CH$_2$)$_{0-3}$NR$^{16}$R$^{17}$ where R$^{16}$ and R$^{17}$ are as defined in relation to formula (Ia). Preferably, R$^{16}$ and R$^{17}$ are independently selected from hydrogen and C$_{1-6}$alkyl. More preferably, R$^{16}$ and R$^{17}$ are independently selected from hydrogen, methyl and ethyl. Most preferably, R$^{16}$ and R$^{17}$ are both methyl. Examples of suitable R$^{14}$ groups include:

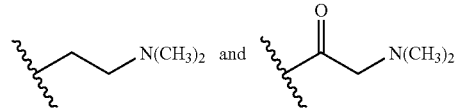

Another favoured group of compounds of the present invention is of formula (Ib) and pharmaceutically acceptable salts thereof:

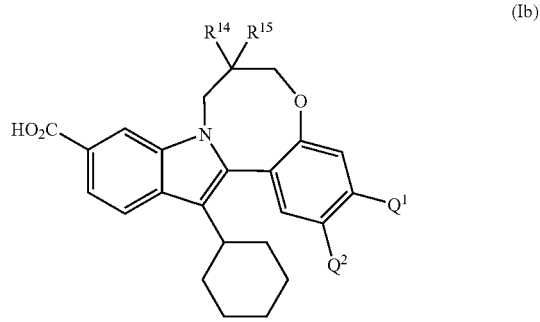

(Ib)

where Q$^1$, Q$^2$, R$^{14}$ and R$^{15}$ are as defined in relation to formula (I), with the proviso that the compound of formula (Ib) is not 14-cyclohexyl-7,8-dihydro-6H-indolo[1,2-e][1,5]benzoxazine-11-carboxylic acid.

In one embodiment, Q$^1$ is absent, fluorine or chlorine. Preferably, Q$^1$ is absent.

In another embodiment, Q$^2$ is absent or fluorine. Preferably, Q$^2$ is absent.

In another embodiment, R$^{14}$ is (CH$_2$)$_{0-1}$OR$^{16}$ or (CH$_2$)$_{0-1}$NR$^{16}$R$^{17}$, where R$^{16}$ and R$^{17}$ are as defined in relation to formula (I). Preferably, R$^{14}$ is OR$^{16}$ or NR$^{16}$R$^{17}$.

When R$^{14}$ is OR$^{16}$, preferably R$^{16}$ is hydrogen, (CH$_2$)$_{1-3}$(C$_{1-6}$alkoxy) or (CH$_2$)$_{1-3}$NR$^{18}$R$^{19}$ where R$^{18}$ and R$^{19}$ are as defined in relation to formula (I). More preferably, R$^{16}$ is hydrogen, (CH$_2$)$_{2-3}$(C$_{1-4}$alkoxy), (CH$_2$)$_{2-3}$N(C$_{1-4}$alkyl)$_2$ or (CH$_2$)$_{2-3}$NR$^{18}$R$^{19}$ where R$^{18}$ and R$^{19}$, together with the nitrogen atom to which they are attached, form a 5- or 6-membered heteroaliphatic ring, which ring may optionally contain 1 or 2 more heteroatoms selected from O and S and/or 1 or 2 groups selected from S(O), S(O)$_2$, NH and NC$_{1-4}$alkyl. Examples of suitable R$^{16}$ groups include hydrogen,

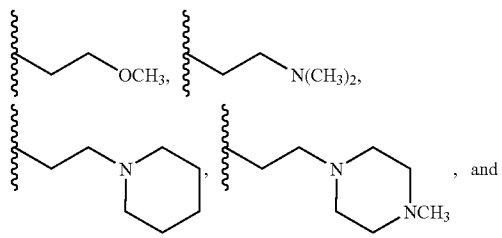

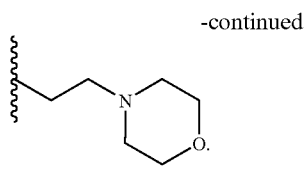

When $R^{14}$ is $NR^{16}R^{17}$, preferably $R^{16}$ is hydrogen, $C_{1-4}$alkyl, $C_{3-8}$cycloalkyl, $(CH_2)_{1-3}NR^{18}R^{19}$, $(CH_2)_{0-3}C_{1-4}$alkoxy, $(CH_2)_{0-2}C(O)(CH_2)_{0-2}N(C_{1-4}alkyl)_2$ or Het, optionally substituted by $C_{1-4}$alkyl, where $R^{18}$ and $R^{19}$ are independently selected from hydrogen, $C_{1-4}$alkyl and heteroaryl, or $R^{18}$ and $R^{19}$, together with the nitrogen atom to which they are attached, form a 5- or 6-membered heteroaliphatic ring, which ring may optionally contain 1 or 2 more heteroatoms selected from O and S and/or 1 or 2 groups selected from $S(O)$, $S(O)_2$, NH and $NC_{1-4}$alkyl.

When $R^{14}$ is $NR^{16}R^{17}$, preferably, $R^{17}$ is hydrogen or $C_{1-6}$alkyl. More preferably, $R^{17}$ is hydrogen methyl, ethyl or i-propyl.

Alternatively, when $R^{14}$ is $NR^{16}R^{17}$, $R^{16}$ and $R^{17}$, together with the nitrogen atom to which they are attached, form a 5- or 6-membered heteroaliphatic ring, which ring may optionally contain 1 or 2 more O atoms and/or 1 or 2 groups selected from NH, $NC_{1-4}$alkyl and $N(CH_2)_{0-3}C_{1-4}$alkoxy. Examples of suitable $NR^{16}R^{17}$ groups include:

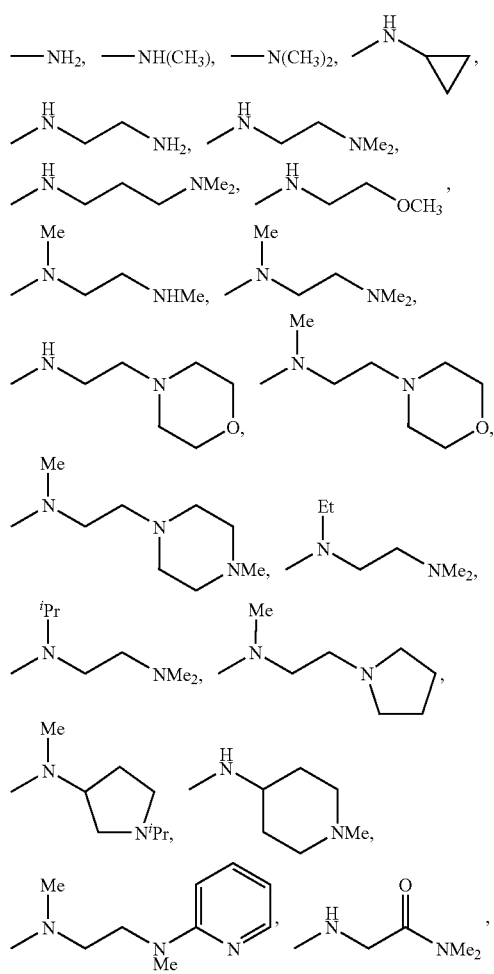

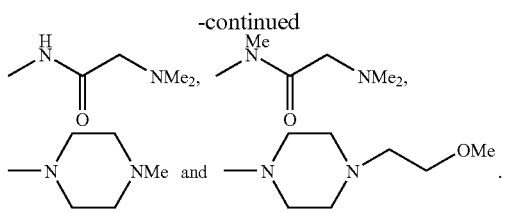

In another embodiment, $R^{15}$ is hydrogen.

Another favoured group of compounds of the present invention is of formula (Ic) and pharmaceutically acceptable salts thereof:

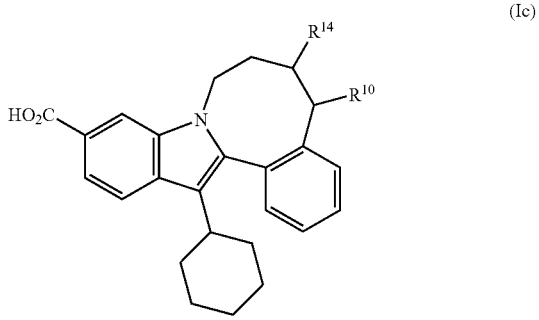

(Ic)

where $R^{10}$ and $R^{14}$ are as defined in relation to formula (I).

In one embodiment, $R^{10}$ is hydrogen, hydroxy, oxo, $OCH_2CH_2NR^cR^d$ or $NHCH_2CH_2NR^cR^d$ where $R^c$ and $R^d$ are as defined in relation to formula (I). Examples of suitable $NR^cR^d$ groups are $NH_2$, $NH(CH_3)$, $N(CH_3)_2$ and pyrrolidinyl.

In another embodiment, $R^{14}$ is hydrogen, $(CH_2)_{0-3}OR^{16}$ or $(CH_2)_{0-3}NR^{16}R^{17}$ where $R^{16}$ and $R^{17}$ are as defined in relation to formula (I). Preferably, $R^{14}$ is hydrogen, $O(CH_2)_{1-3}NR^{18}R^{19}$ or $NH(CH_2)_{1-3}NR^{18}R^{19}$ where $R^{18}$ and $R^{19}$ are as defined in relation to formula (I). More preferably, $R^{14}$ is hydrogen or

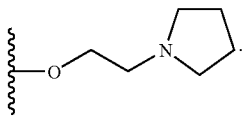

When any variable occurs more than one time in formula (I) or in any substituent, its definition on each occurrence is independent of its definition at every other occurrence.

As used herein, the term "alkyl" or "alkoxy" as a group or part of a group means that the group is straight or branched. Examples of suitable alkyl groups include methyl, ethyl, n-propyl, i-propyl, n-butyl, s-butyl and t-butyl. Examples of suitable alkoxy groups include methoxy, ethoxy, n-propoxy, i-propoxy, n-butoxy, s-butoxy and t-butoxy.

The cycloalkyl groups referred to herein may represent, for example, cyclopropyl, cyclobutyl, cyclopentyl or cyclohexyl. A suitable cycloalkylalkyl group may be, for example, cyclopropylmethyl.

As used herein, the term "alkenyl" as a group or part of a group means that the group is straight or branched. Examples of suitable alkenyl groups include vinyl and allyl.

When used herein, the term "halogen" means fluorine, chlorine, bromine and iodine.

When used herein, the term "aryl" as a group or part of a group means a carbocyclic aromatic ring. Examples of suitable aryl groups include phenyl and naphthyl.

When used herein, the term "heteroaryl" as a group or part of a group means a 5- to 10-membered heteroaromatic ring system containing 1 to 4 heteroatoms selected from N, O and S. Particular examples of such groups include pyrrolyl, furanyl, thienyl, pyridyl, pyrazolyl, imidazolyl, oxazolyl, isoxazolyl, thiazolyl, isothiazolyl, pyrazinyl, pyrimidinyl, pyridazinyl, triazolyl, oxadiazolyl, thiadiazolyl, triazinyl, tetrazolyl, indolyl, benzothienyl, benzimidazolyl and quinolinyl.

When used herein, the term "Het" as a group or part of a group means a heteroaliphatic ring of 4 to 7 atoms, which ring may contain 1, 2 or 3 heteroatoms selected from N, O and S or a group $S(O)$, $S(O)_2$, NH or $NC_{1-4}$alkyl.

Where a compound or group is described as "optionally substituted" one or more substituents may be present. Optional substituents may be attached to the compounds or groups which they substitute in a variety of ways, either directly or through a connecting group of which the following are examples: amine, amide, ester, ether, thioether, sulfonamide, sulfamide, sulfoxide, urea, thiourea and urethane. As appropriate an optional substituent may itself be substituted by another substituent, the latter being connected directly to the former or through a connecting group such as those exemplified above.

Specific compounds within the scope of this invention include those named in the Examples and Tables below and their pharmaceutically acceptable salts.

For use in medicine, the salts of the compounds of formula (I) will be non-toxic pharmaceutically acceptable salts. Other salts may, however, be useful in the preparation of the compounds according to the invention or of their non-toxic pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, fumaric acid, p-toluenesulfonic acid, maleic acid, succinic acid, acetic acid, citric acid, tartaric acid, carbonic acid, phosphoric acid or sulfuric acid. Salts of amine groups may also comprise quaternary ammonium salts in which the amino nitrogen atom carries a suitable organic group such as an alkyl, alkenyl, alkynyl or aralkyl moiety. Furthermore, where the compounds of the invention carry an acidic moiety, suitable pharmaceutically acceptable salts thereof may include metal salts such as alkali metal salts, e.g. sodium or potassium salts; and alkaline earth metal salts, e.g. calcium or magnesium salts.

The salts may be formed by conventional means, such as by reacting the free base form of the product with one or more equivalents of the appropriate acid in a solvent or medium in which the salt is insoluble, or in a solvent such as water which is removed in vacuo or by freeze drying or by exchanging the anions of an existing salt for another anion on a suitable ion exchange resin.

The present invention includes within its scope prodrugs of the compounds of formula (I) above. In general, such prodrugs will be functional derivatives of the compounds of formula (I) which are readily convertible in vivo into the required compound of formula (I). Conventional procedures for the selection and preparation of suitable prodrug derivatives are described, for example, in "Design of Prodrugs", ed. H. Bundgaard, Elsevier, 1985.

A prodrug may be a pharmacologically inactive derivative of a biologically active substance (the "parent drug" or "parent molecule") that requires transformation within the body in order to release the active drug, and that has improved delivery properties over the parent drug molecule. The transformation in vivo may be, for example, as the result of some metabolic process, such as chemical or enzymatic hydrolysis of a carboxylic, phosphoric or sulfate ester, or reduction or oxidation of a susceptible functionality.

The present invention includes within its scope solvates of the compounds of formula (I) and salts thereof, for example, hydrates.

The present invention also includes within its scope N-oxides of the compounds of formula (I).

The present invention also includes within its scope any enantiomers, diastereomers, geometric isomers and tautomers of the compounds of formula (I). It is to be understood that all such isomers and mixtures thereof are encompassed within the scope of the invention.

The present invention further provides a compound of formula (I) or a pharmaceutically acceptable salt thereof for use in therapy.

In another aspect, the invention provides the use of a compound of formula (I) as defined above, or a pharmaceutically acceptable salt thereof, for the manufacture of a medicament for treatment or prevention of infection by hepatitis C virus in a human or animal.

A further aspect of the invention provides a pharmaceutical composition comprising a compound of formula (I) as defined above, or a pharmaceutically acceptable salt thereof, in association with a pharmaceutically acceptable carrier. The composition may be in any suitable form, depending on the intended method of administration. It may for example be in the form of a tablet, capsule or liquid for oral administration, or of a solution or suspension for administration parenterally.

The pharmaceutical compositions optionally also include one or more other agents for the treatment of viral infections such as an antiviral agent, or an immunomodulatory agent such as $\alpha$-, $\beta$- or $\gamma$-interferon.

In a further aspect, the invention provides a method of inhibiting hepatitis C virus polymerase and/or of treating or preventing an illness due to hepatitis C virus, the method involving administering to a human or animal (preferably mammalian) subject suffering from the condition a therapeutically or prophylactically effective amount of the pharmaceutical composition described above or of a compound of formula (I) as defined above, or a pharmaceutically acceptable salt thereof. "Effective amount" means an amount sufficient to cause a benefit to the subject or at least to cause a change in the subject's condition.

The dosage rate at which the compound is administered will depend on a variety of factors including the activity of the specific compound employed, the metabolic stability and length of action of that compound, the age of the patient, body weight, general health, sex, diet, mode and time of administration, rate of excretion, drug combination, the severity of the particular condition and the host undergoing therapy. Suitable dosage levels may be of the order of 0.02 to 5 or 10 g per day, with oral dosages two to five times higher. For instance, administration of from 10 to 50 mg of the compound per kg of body weight from one to three times per day may be in order. Appropriate values are selectable by routine testing. The compound may be administered alone or in combination with other treatments, either simultaneously or sequentially. For instance, it may be administered in combination with effective amounts of antiviral agents, immunomodulators, anti-infectives or vaccines known to those of ordinary skill in the art. It may be administered by any suitable route, including orally, intravenously, cutaneously and subcutaneously. It may be administered directly to a suitable site or in a manner in which it targets a particular site, such as a certain type of cell. Suitable targeting methods are already known.

An additional aspect of the invention provides a method of preparation of a pharmaceutical composition, involving admixing at least one compound of formula (I) as defined above, or a pharmaceutically acceptable salt thereof, with one or more pharmaceutically acceptable adjuvants, diluents or carriers and/or with one or more other therapeutically or prophylactically active agents.

The present invention also provides a process for the preparation of compounds of formula (I).

According to a general process (a), compounds of formula (I) where Y is $NR^{14}$ may be prepared by internal ring closure of a compound of formula (II):

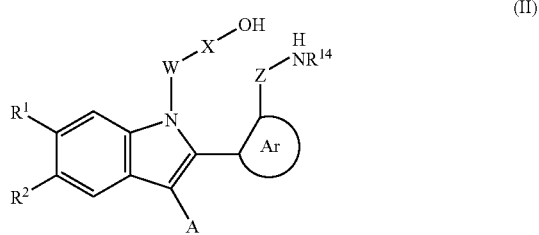

wherein $R^1$, $R^2$, A, Ar, W, X and Z are as defined in relation to formula (I). The reaction is conveniently performed in the presence of a coupling reagent, such as HATU or TBTU, and a base, such as diisopropylethylamine or triethylamine, in a solvent. Suitable solvents include dichloromethane and DMF.

According to a general process (b), compounds of formula (I) may be prepared by internal ring closure of a compound of formula (III):

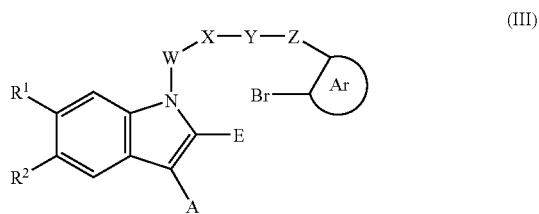

wherein $R^1$, $R^2$, A, Ar, W, X, Y and Z are as defined in relation to formula (I) and E is hydrogen or bromine. The reaction is conveniently performed in the presence of a Pd(0) catalyst, such as $PdCl_2(dppf)$, a dioxoborolane, such as 4,4,4',4',5,5,5',5'-octamethyl-2,2'-bi-1,3,2-dioxaborolane, and a base, such as potassium acetate, in a suitable solvent, such as DMF, under a nitrogen atmosphere.

According to a general process (c), compounds of formula (I) may be prepared by internal ring closure of a compound of formula (IV):

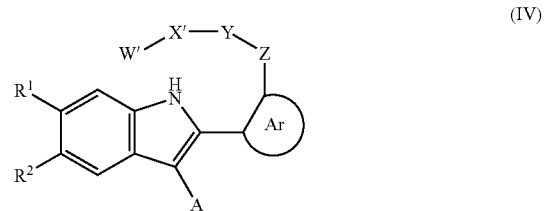

wherein $R^1$, $R^2$, A, Ar, Y and Z are as defined in relation to formula (I) and X' is X as defined in relation to formula (I) or is converted to X during or after the cyclisation reaction, and W' is W as defined in relation to formula (I) or converted to W during or after the cyclisation reaction. W' and X' may be suitable activated precursors of groups W and X respectively which can be converted into W and X during the ring closure or after it using methods described in the accompanying Schemes and Examples or known to the person skilled in the art. For example, W' may be $CH_2$-halogen or W' and X' together may be an epoxide or aziridine group. When W' is $CH_2$-halogen, such as $CH_2$—Br, the reaction is conveniently performed in the presence of a base, such as sodium hydroxide, in a suitable solvent, such as DMF. When W' and X' are an epoxide group, the reaction is conveniently performed in the presence of a base, such as sodium hydroxide, in a suitable solvent, such as DMF.

Compounds of formulae (II), (III) and (IV) are either known in the art or may be prepared by conventional methodology well known to one of ordinary skill in the art using, for instance, procedures described in the accompanying Schemes and Examples, or by alternative procedures which will be readily apparent.

Further details of suitable procedures will be found in the accompanying Schemes and Examples. For instance, compounds of formula (I) can be converted into other compounds of formula (I) using synthetic methodology well known in the art.

Thus, for instance, the compound of formula (I) where $R^1$ is $CO_2CH_3$ may be converted into the compound of formula (I) where $R^1$ is $CO_2H$ by conversion of the ester to the carboxylic acid, for example, by treatment with $BBr_3$ in a suitable solvent, such as dichloromethane, or with NaOH in a suitable solvent, such as dioxane, THF and/or methanol.

In addition, the compound of formula (I) where X is C=O may be converted into the compound of formula (I) where X is $CH_2$ by reduction of the oxo group with, for instance, a borane reagent, such as $BH_3.Me_2S$, in a suitable solvent, such as THF.

General Synthetic Schemes

In general, five synthetic schemes may be used to obtain the compounds of formula (I).

Method A

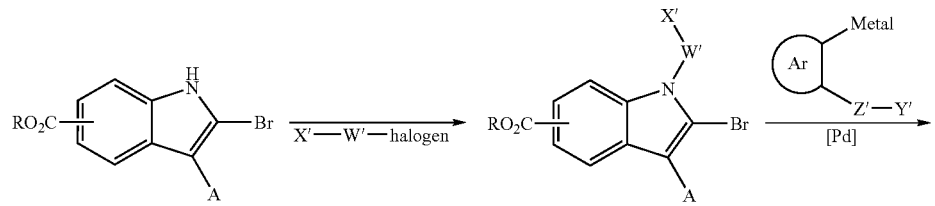

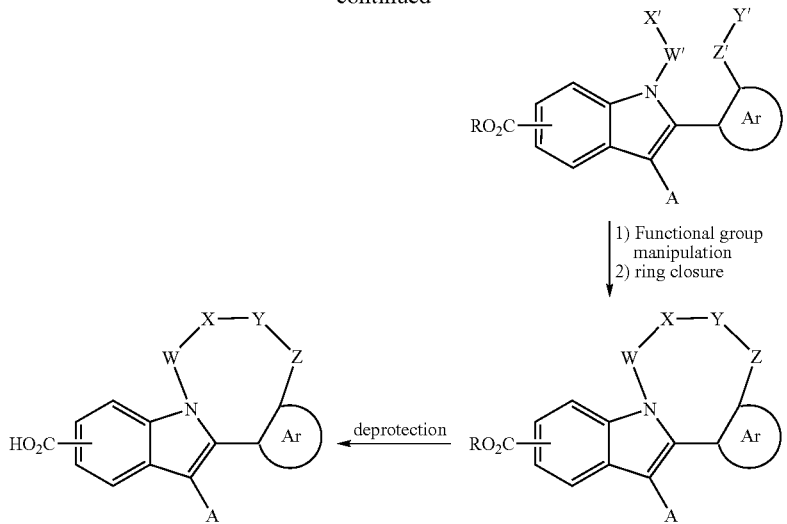

2-bromoindole intermediate (prepared as described in published International patent application WO2004/087714) was functionalized on the indole nitrogen to introduce precursor functionality W'/X' to either or both of the elements —CH$_2$—/X of the tether. Pd-mediated cross-coupling methodology (eg, Suzuki, Stille etc) then brought in the C2 aromatic bearing pre-cursor functionality Z'/Y' to either or both of the elements Z/Y of the tether. Functional group manipulation followed by ring closure afforded the tetracyclic system. Ester deprotection then yielded the target indole carboxylic acids, with the C2 aromatic tethered to the indole nitrogen.

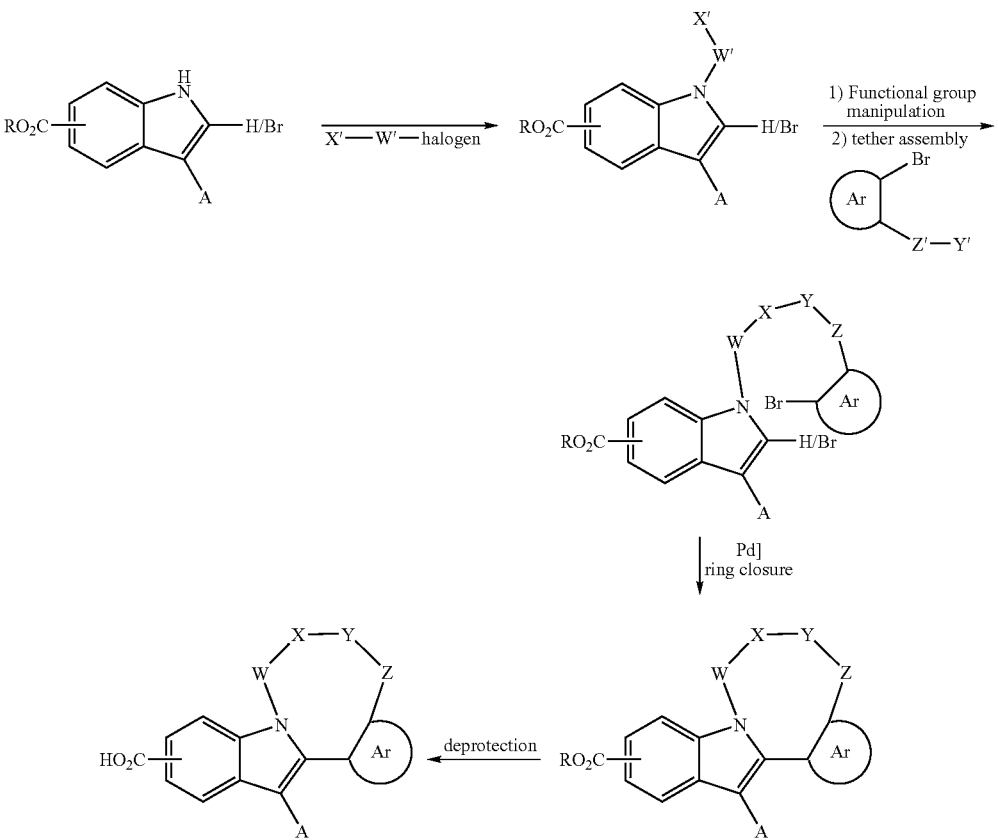

Following tether assembly out to the appropriate 2-haloaromatic, Pd-mediated ring closure afforded the fused tetracyclic system. Ester deprotection then yielded the target indole carboxylic acids, with the C2 aromatic tethered to the indole nitrogen.

Fused tetracyclic intermediates arising from Methods A-C underwent manipulation of the functionality in the tether prior to ester deprotection to yield the target C2-tethered indole carboxylic acids.

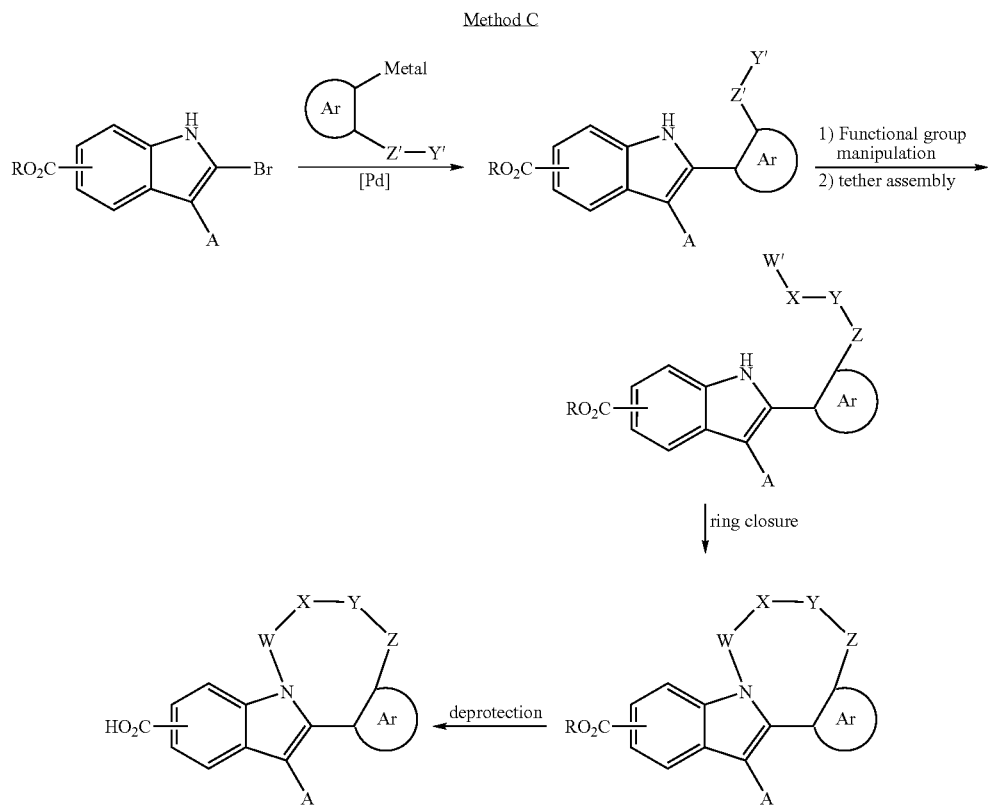

The C2 aromatic was introduced at the outset via Pd-mediated cross-coupling methodology (Suzuki, Stille etc). The tether was then built up, with cyclisation onto the indole nitrogen finally closing the ring. Ester deprotection then yielded the target indole carboxylic acids, with the C2 aromatic tethered to the indole nitrogen.

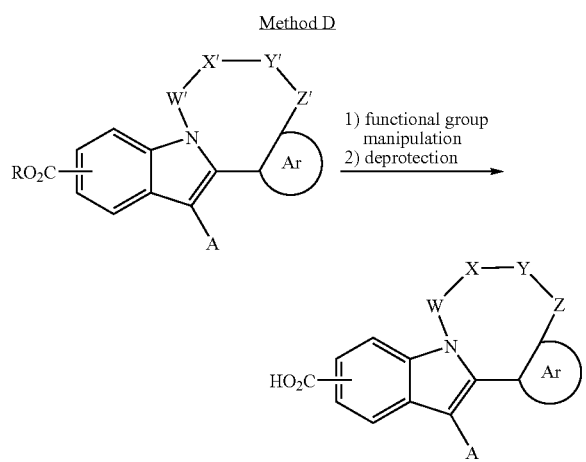

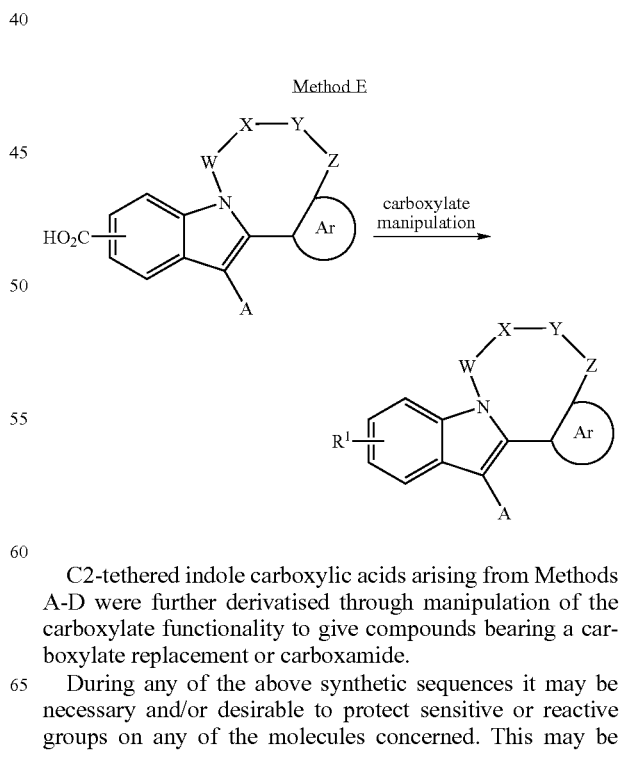

C2-tethered indole carboxylic acids arising from Methods A-D were further derivatised through manipulation of the carboxylate functionality to give compounds bearing a carboxylate replacement or carboxamide.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 3rd edition, 1999. The protecting groups may be removed at a convenient subsequent stage using methods known from the art.

The following Examples are illustrative of this invention.

The compounds of the invention were tested for inhibitory activity against the HCV RNA dependent RNA polymerase (NS5B) in an enzyme inhibition assay (example i)) and in a cell based sub-genomic replication assay (example ii)). The compounds have IC50's below 5 μM in the enzyme assay and several examples have EC50's below 2 μM in the cell based assay.

Compound names in the examples were generated using software from ACDLabs (version 6.0).

i) In-vitro HCV NS5B Enzyme Inhibition Assay

WO 96/37619 describes the production of recombinant HCV RdRp from insect cells infected with recombinant baculovirus encoding the enzyme. The purified enzyme was shown to possess in vitro RNA polymerase activity using RNA as template. The reference describes a polymerisation assay using poly(A) and oligo(U) as a primer or an heteropolymeric template. Incorporation of tritiated UTP or NTPs is quantified by measuring acid-insoluble radioactivity. This assay has been employed to screen the various compounds described above as inhibitors of HCV RdRp.

Incorporation of radioactive UMP was measured as follows. The standard reaction (50 μl) was carried out in a buffer containing 20 mM tris/HCl pH 7.5, 5 mM $MgCl_2$, 1 mM DTT, 50 mM NaCl, 0.03% N-octylglucoside, 1 μCi [$^3$H]-UTP (40 Ci/mmol, NEN), 10 μM UTP and 10 μg/ml poly(A) or 5 μM NTPs and 5 μg/ml heteropolymeric template. $OLIGO(U)_{12}$ (1 μg/ml, GENSET) was added as a primer in the assay working on POLY(A) template. The final NS5B enzyme concentration was 5 nM. The order of assembly was: 1) compound, 2) enzyme, 3) template/primer, 4) NTP. After 1 h incubation at 22° C. the reaction was stopped by adding 50 μl of 20% TCA and applying samples to DE81 filters. The filters were washed thoroughly with 5% TCA containing 1M $Na_2HPO_4$/$NaH_2PO_4$, pH 7.0, rinsed with water and then ethanol, air dried, and the filter-bound radioactivity was measured in the scintillation counter. Carrying out this reaction in the presence of various concentrations of each compound set out above allowed determination of $IC_{50}$ values by utilising the formula:

$$\% \text{ Residual activity} = 100/(1+[I]/IC_{50})^S$$

where [I] is the inhibitor concentration and "s" is the slope of the inhibition curve.

ii) Cell Based HCV Replication Assay

Cell clones that stably maintain subgenomic HCV replicon were obtained by transfecting Huh-7 cells with an RNA replicon identical to $I_{377}$neo/NS3-3'/wt described by Lohmann et al. (1999) (EMBL-genbank No. AJ242652), followed by selection with neomycin sulfate (G418). Viral replication was monitored by measuring the expression of the NS3 protein by an ELISA assay performed directly on cells grown in 96 wells microtiter plates (Cell-ELISA) using the anti-NS3 monoclonal antibody 10E5/24 (as described in published International patent application WO02/59321). Cells were seeded into 96 well plates at a density of $10^4$ cells per well in a final volume of 0.1 ml of DMEM/10% FCS. Two hours after plating, 50 μl of DMEM/10% FCS containing a 3× concentration of inhibitor were added, cells were incubated for 96 hours and then fixed for 10' with ice-cold isopropanol. Each condition was tested in duplicate and average absorbance values were used for calculations. The cells were washed twice with PBS, blocked with 5% non-fat dry milk in PBS+ 0.1% Triton X100+0.02% SDS (PBSTS) and then incubated o/n at 4° C. with the 10E5/24 mab diluted in Milk/PBSTS. After washing 5 times with PBSTS, the cells were incubated for 3 hours at room temperature with Fc specific anti-mouse IgG conjugated to alkaline phosphatase (Sigma), diluted in Milk/PBSTS. After washing again as above, the reaction was developed with p-Nitrophenyl phosphate disodium substrate (Sigma) and the absorbance at 405/620 nm read at intervals. For calculations, we used data sets where samples incubated without inhibitors had absorbance values comprised between 1 and 1.5. The inhibitor concentration that reduced by 50% the expression of NS3 ($IC_{50}$) was calculated by fitting the data to the Hill equation, $$\text{Fraction inhibition} = 1 - (A_i - b)/(A_0 - b) = [I]^n/([I]^n + IC_{50})$$

where:

$A_i$=absorbance value of HBI10 cells supplemented with the indicated inhibitor concentration.

$A_0$=absorbance value of HBI10 cells incubated without inhibitor.

b=absorbance value of Huh-7 cells plated at the same density in the same microtiter plates and incubated without inhibitor.

n=Hill coefficient.

iii) General Procedures

All solvents were obtained from commercial sources (FLUKA, PURISS.) and were used without further purification. With the exception of routine deprotection and coupling steps, reactions were carried out under an atmosphere of nitrogen in oven dried (110° C.) glassware. Organic extracts were dried over sodium sulfate, and were concentrated (after filtration of the drying agent) on rotary evaporators operating under reduced pressure. Flash chromatography was carried out on silica gel following published procedure (W. C. Still et al., J. Org. Chem. 1978, 43, 2923) or on commercial flash chromatography systems (Biotage Corporation and JONES FLASHMASTER II) utilising pre-packed columns.

Reagents were usually obtained directly from commercial suppliers (and used as supplied) but a limited number of compounds from in-house corporate collections were utilised. In the latter case the reagents are readily accessible using routine synthetic steps that are either reported in the scientific literature or are known to those skilled in the art.

$^1$H NMR spectra were recorded on BRUKER AM series spectrometers operating at (reported) frequencies between 300 and 600 MHz. Chemical shifts (δ) for signals corresponding to non-exchangeable protons (and exchangeable protons where visible) are recorded in parts per million (ppm) relative to tetramethylsilane and are measured using the residual solvent peak as reference. Signals are tabulated in the order: multiplicity (s, singlet; d, doublet; t, triplet; q, quartet; m, multiplet; b, broad, and combinations thereof); coupling constant(s) in hertz (Hz); number of protons. Mass spectral (MS) data were obtained on a PERKIN ELMER API 100, or Waters MICROMASS ZQ, operating in negative (ES$^-$) or positive (ES$^+$) ionization mode and results are reported as the ratio of mass over charge (m/z) for the parent ion only. Preparative scale HPLC separations were carried out on a Waters DELTA PREP 4000 separation module, equipped with a Waters 486 absorption detector or on a GILSON preparative system. In all cases compounds were eluted with linear gradients of water and MeCN both containing 0.1% TFA using flow rates between 15 and 40 mL/min.

The following abbreviations are used in the examples, the schemes and the tables: Ac: acetyl; Ar: aryl; cat.: catalytic; dioxan(e): 1,4-dioxane; dppf: (1,1'-bisdiphenylphosphino) ferrocene; 1,2-DCE: 1,2-dichloroethane; DCM: dichloromethane; DIPEA: diisopropylethyl amine; DMAP: N,N-dimethylpyridin-4-amine; DME: dimethoxyethane; DMF: dimethylformamide; DMSO: dimethylsulfoxide; DMP: Dess-Martin Periodinane; EDAC.HCl: 1-ethyl-(3-dimethylaminopropyl)carbodiimide HCl salt; eq.: equivalent(s); Et$_3$N: triethylamine; EtOAc: ethyl acetate; Et$_2$O: diethyl ether; EtOH: ethanol; h: hour(s); Et$_3$SiH: triethylsilane; HOAc: acetic acid; HATU: O-(7-azabenzotriazol-1-yl)-N,N,N',N'-tetramethyluronium hexafluorophophate; Me: methyl; MeCN: acetonitrile; MeOH: methanol; min: minutes; MS: mass spectrum; NBS: N-bromo succinimide; PE: petroleum ether; Ph: phenyl; quant.: quantitative; RP-HPLC: reversed phase high-pressure liquid chromatography; RT: room temperature; sec: second(s); SFC: Super-critical fluid chromatography; s.s.: saturated solution; TBTU: O-benzotriazol-1-yl-N,N,N',N'-tetramethyluronium tetrafluoroborate; TFA: trifluoroacetic acid; THF: tetrahydrofuran; THP: terhahydropyranyl; TMS: trimethylsilyl.

Reagents: Zhan catalyst I ([1,3-bis(2,4,6-trimethylphenyl)-4,5-dihydro-imidazol-2-ylidene]-[4-chloro-1-isopropxy-benzylidine]ruthenium-dichloride: commercially available from ZannanPharma Ltd.; methyl (aminosulfonyl) acetate was prepared in analogous fashion to related esters of aminosulfonyl acetic acid: eg, *Tetrahedron Lett.* 1989, 30 (22), 2869; *Bull. Soc. Chim. France* 1975, 3, 807.

EXAMPLE 1

14-cyclohexyl-6-[2-(dimethylamino)ethyl]-7-oxo-5,6,7,8 tetrahydroindolo[2,1-a][2,5]benzodiazocine-11-carboxylic acid Step 1: methyl 2-bromo-1-(2-tert-butoxy-2-oxoethyl)-3-cyclohexyl-1H-indole-6-carboxylate NaH (1.4 eq, 60% dispersion in mineral oil) was added to a solution of methyl 2-bromo-3-cyclohexyl-1H-indole-6-carboxylate (prepared as described in published International Patent application WO 2004/065367, from commercially available methyl indole-6-carboxylate) in DMF (0.2 M) and the solution stirred at RT for 1 h. Then tert-butyl bromoacetate (1.1 eq) was added and the mixture stirred at RT for 40 min. The solvent was removed in vacuo and the residue taken up in EtOAc. The organic phase was washed with H$_2$O (twice) and then brine. The organic phase was dried over Na$_2$SO$_4$, filtered and the solvent evaporated in vacuo to afford the title compound as a brownish solid (90%); MS (ES$^+$) m/z 450 (M+H)$^+$, m/z 452 (M+H)$^+$ Step 2: methyl 1-(2-tert-butoxy-2-oxoethyl)-3-cyclohexyl-2-(2-formylphenyl)-1H-indole-6-carboxylate To a solution of methyl 2-bromo-1-(2-tert-butoxy-2-oxoethyl)-3-cyclohexyl-1H-indole-6-carboxylate in 1,4-dioxane (0.15 M) was added Na$_2$CO$_3$ (6 eq, 2 M solution), (2-formylphenyl)boronic acid (1.5 eq) and bis(triphenylphosphine)palladium(II) dichloride (0.2 eq) and the mixture heated at reflux for 45 min. The reaction mixture was allowed to cool and filtered. The filtrate was diluted with EtOAc and the organic phase washed with H$_2$O, brine and dried over Na$_2$SO$_4$ before being filtered and concentrated in vacuo. The crude material was purified by flash chromatography (1:9 EtOAc/PE) to afford the title compound as a yellow solid (53%); MS (ES$^+$) m/z 476 (M+H)$^+$ Step 3: methyl 1-(2-tert-butoxy-2-oxoethyl)-3-cyclohexyl-2-[2-({[2-(dimethylamino)ethyl]amino}methyl)phenyl]-1H-indole-6-carboxylate To a solution of methyl 1-(2-tert-butoxy-2-oxoethyl)-3-cyclohexyl-2-(2-formylphenyl)-1H-indole-6-carboxylate in THF (0.2 M), N,N-dimethylethane-1,2-diamine (10 eq) was added and the pH adjusted to pH 6 with acetic acid. The solution was stirred at RT for 1 h, then the THF was removed in vacuo and the residue taken up in MeOH to give a 0.2 M solution. NaBH$_3$CN (2 eq) was added and the mixture stirred at RT overnight. The reaction mixture was diluted with EtOAc and the organic phase washed with a saturated aqueous solution of NaHCO$_3$, H$_2$O and then brine. The organic phase was dried over Na$_2$SO$_4$, filtered and concentrated in vacuo to give the title compound (95%); MS (ES$^+$) m/z 548 (M+H)$^+$ Step 4: [3-cyclohexyl-2-[2-({[2-(dimethylamino)ethyl]amino}methyl)phenyl]-6-(methoxycarbonyl)-1H-indol-1-yl]acetic acid To a solution of methyl 1-(2-tert-butoxy-2-oxoethyl)-3-cyclohexyl-2-[2-({[2-(dimethylamino)ethyl]amino}methyl)phenyl]-1H-indole-6-carboxylate in DCM/H$_2$O (2:1; 0.15 M), a stoichiometric excess of TFA was added dropwise and the solution was stirred at RT overnight. The volatiles were removed in vacuo, the residue taken up in Et$_2$O, scratched and concentrated in vacuo again (2×) to drive off residual TFA. The crude was used in the next step without further purification; MS (ES$^+$) m/z. 492 (M+H)$^+$ Step 5: methyl 14-cyclohexyl-6-[2-(dimethylamino)ethyl]-7-oxo-5,6,7,8-tetrahydroindolo[2,1-a][2,5]benzodiazocine-11-carboxylate To a solution of [3-cyclohexyl-2-[2-({[2-(dimethylamino)ethyl]amino}methyl)phenyl]-6-(methoxycarbonyl)-1H-indol-1-yl]acetic acid in DCM (0.08 M), DIPEA (3.5 eq) and HATU (2.5 eq) were added and the mixture stirred at RT overnight. The solution was diluted with DCM and HCl (1N) and the 2 phases separated. The aqueous phase was extracted with DCM (2×). The combined organic phases were then washed with a saturated aqueous solution of NaHCO$_3$ and brine before being dried over Na$_2$SO$_4$, filtered and concentrated in vacuo. The crude was then used in the next step without further purification; MS (ES$^+$) m/z 474 (M+H)$^+$ Step 6: 14-cyclohexyl-6-[2-(dimethylamino)ethyl]-7-oxo-5,6,7,8-tetrahydroindolo[2,1-a][2.5]benzodiazocine-11-carboxylic acid To a solution of methyl 14-cyclohexyl-6-[2-(dimethylamino)ethyl]-7-oxo-5,6,7,8-tetrahydroindolo[2,1-a][2,5]benzodiazocine-11-carboxylate in DCM (0.02 M) was added dropwise a solution of BBr$_3$ in DCM (1 M). The solution was stirred at RT for 30 min. Volatiles were removed in vacuo. The crude was then purified by automated RP-MS-HPLC (stationary phase: column Waters XTERRA prep. C18, 5 um, 19×100 mm. Mobile phase: MeCN/H$_2$O buffered with 0.1% TFA). Fractions containing the pure compound were combined and freeze dried to afford the title compound as a white powder (20%).

¹H NMR (400 MHz, DMSO-d₆, 300 K) δ 1.17-1.1.23 (m, 1H), 1.24-1.40 (m, 2H), 1.56-1.59 (m, 1H), 1.65-1.79 (m, 2H), 1.82-2.0 (m, 4H), 2.70-2.85 (m, 3H), 2.85 (s, 6H), 3.68-3.78 (m, 1H), 3.90-4.06 (m, 2H), 4.23 (d, J 17.2, 1H), 4.30 (d, J 14.8, 1H), 4.80 (d, J 17.2, 1H), 7.51-7.55 (m, 1H), 7.60-7.67 (m, 2H), 7.72 (d, J 8.4, 1H), 7.77-7.82 (m, 1H), 7.91-7.96 (m, 2H), 9.29 (br s, 1H), 12.78 (br s, 1H); MS (ES⁺) m/z 460 (M+H)⁺

EXAMPLE 2

14-cyclohexyl-6-(2-morpholin-4-ylethyl)-7-oxo-5,6,7,8-tetrahydroindolo[2,1-a][2,5]benzodiazocine-11-carboxylic acid Step 1: methyl 1-(2-tert-butoxy-2-oxoethyl)-3-cyclohexyl-2-(2-{[(2-morpholin-4-ylethyl)amino]methyl}phenyl)-1H-indole-6-carboxylate The title compound was obtained following the same procedure described in Example 1, Step 3 for the synthesis of methyl 1-(2-tert-butoxy-2-oxoethyl)-3-cyclohexyl-2-[2-({[2-(dimethylamino)ethyl]amino}methyl)phenyl]-1H-indole-6-carboxylate, using 2-morpholin-4-ylethyl amine instead of N,N-dimethylethane-1,2-diamine. The title compound was obtained in a 92% yield; MS (ES⁺) m/z 590 (M+H)⁺

Step 2: [3-cyclohexyl-6-(methoxycarbonyl)-2-(2-{[(2-morpholin-4-ylethyl)amino]methyl}phenyl)-1H-indol-1-yl]acetic acid The title compound was prepared using the same procedure described for [3-cyclohexyl-2-[2-({[2-(dimethylamino)ethyl]-amino}methyl)phenyl]-6-(methoxycarbonyl)-1H-indol-1-yl]acetic acid in Example 1, Step 4. The crude was used in the next step without further purification; MS (ES⁺) m/z 534 (M+H)⁺

Step 3: methyl 14-cyclohexyl-6-(2-morpholin-4-ylethyl)-7-oxo-5,6,7,8-tetrahydroindolo[2,1-a][2,5]benzodiazocine-11-carboxylate The title compound was prepared using the same procedure described for methyl 14-cyclohexyl-6-[2-(dimethylamino)ethyl]-7-oxo-5,6,7,8-tetrahydroindolo[2,1-a][2,5]benzodiazocine-11-carboxylate in Example 1, Step 5. The crude was used in the next step without further purification; MS (ES⁺) m/z 516 (M+H)⁺

Step 4: methyl 14-cyclohexyl-6-(2-morpholin-4-ylethyl)-5,6,7,8-tetrahydroindolo[2,1-a][2,5]benzodiazocine-11-carboxylate To a solution of methyl 14-cyclohexyl-6-(2-morpholin-4-ylethyl)-7-oxo-5,6,7,8-tetrahydroindolo[2,1-a][2,5]benzodiazocine-11-carboxylate in THF (0.15 M), 20 eq of BH₃Me₂S (2 M solution in THF) was added dropwise and the solution stirred at RT for 2 h. MeOH was added carefully to the mixture until effervescence ceased, then the volatiles were removed in vacuo. The crude residue was not isolated and directly used in the next step; MS (ES⁺) m/z 502 (M+H)⁺.

Step 5: 14-cyclohexyl-6-(2-morpholin-4-ylethyl)-5,6,7,8-tetrahydroindolo[2,1-a][2,5]benzodiazocine-11-carboxylic acid The crude methyl 14-cyclohexyl-6-(2-morpholin-4-ylethyl)-5,6,7,8-tetrahydroindolo[2,1-a][2,5]benzodiazocine-11-carboxylate was dissolved in THF/MeOH (1:1) and to that solution an excess of NaOH (1N) was added. The solution was stirred at RT overnight. The solvent was evaporated in vacuo. The crude was then purified by automated RP-MS-HPLC (stationary phase: column Waters XTERRA prep. C18, 5 um, 19×100 mm. Mobile phase: MeCN/H₂O buffered with 0.1% TFA). Fractions containing the pure compound were combined and freeze dried to afford the title compound as a white powder (20%).

¹H NMR (400 MHz, DMSO-d₆+TFA, 300 K) δ 1.0-1.20 (m, 1H), 1.21-1.40 (m, 2H), 1.45-1.60 (m, 1H), 1.60-1.75 (m, 2H), 1.75-1.85 (m, 1H), 1.85-2.0 (m, 3H), 2.63-2.67 (m, 1H), 3.33 (bs, 4H), 3.48-3.51 (m, 1H), 3.52-3.80 (m, 7H), 3.84 (bs, 4H), 4.42 (d, J 13.6, 1H), 4.84 (dd, J 16.2, 4.6, 1H), 7.48-7.51 (m, 1H), 7.61-7.70 (m, 2H), 7.74 (dd, J 8.4, 1.2, 1H), 7.84-7.90 (m, 1H), 7.93 (d, J 8.4, 1H), 8.2 (s, 1H); MS (ES⁺) m/z 488 (M+H)⁺.

EXAMPLE 3

14-cyclohexyl-6-[2-(dimethylamino)ethyl]-3-methoxy-5,6,7,8-tetrahydroindolo[2,1-a][2,5]benzodiazocine-11-carboxylic acid Step 1: methyl 14-cyclohexyl-6-[2-(dimethylamino)ethyl]-3-methoxy-5,6,7,8-tetrahydroindolo[2,1-a][2,5]benzodiazocine-11-carboxylate To a solution of methyl 14-cyclohexyl-6-[2-(dimethylamino)ethyl]-3-methoxy-7-oxo-5,6,7,8-tetrahydroindolo[2,1-a][2,5]benzodiazocine-11-carboxylate (prepared in an analogous fashion to that described in Example 1) in THF (0.06 M), BH₃Me₂S (20 eq, 2 M solution in THF) was dropwise and the solution stirred at RT for 3 h. MeOH was added carefully to the mixture until effervescence ceased, then the volatiles were removed in vacuo. The crude residue was not isolated and directly used in the next step; MS (ES⁺) m/z 490 (M+H)⁺.

Step 2: 14-cyclohexyl-6-[2-(dimethylamino)ethyl]-3-methoxy-5,6,7,8-tetrahydroindolo[2,1-a][2,5]benzodiazocine-11-carboxylic acid The crude methyl 14-cyclohexyl-6-[2-(dimethylamino)ethyl]-3-methoxy-5,6,7,8-tetrahydroindolo[2,1-a][2,5]benzodiazocine-11-carboxylate was dissolved in dioxane (0.06 M) and to that solution 10 eq of an aqueous solution of NaOH (2N) were added. The solution was stirred at 60° C. for 3 h. The solvent was evaporated in vacuo. The crude was then purified by automated RP-MS-HPLC (stationary phase: column Waters XTERRA prep. C18, 5 um, 19×100 mm. Mobile phase: MeCN/H₂O buffered with 0.1% TFA). Fractions containing the pure compound were combined and freeze dried to afford the title compound as a white powder (28%).

¹H NMR (400 MHz, DMSO-d₆+TFA, 300 K) δ 1.08-1.20 (m, 1H), 1.24-1.40 (m, 2H), 1.46-1.55 (m, 1H), 1.63-1.75 (m, 2H), 1.78-2.0 (m, 4H), 2.55-2.67 (m, 1H), 2.84 (s, 6H), 2.88-3.01 (m, 3H), 3.4-3.65 (m, 5H, partially obscured by water peak), 3.75-3.80 (m, 1H), 3.89 (s, 3H), 4.41-4.51 (m, 1H), 7.08 (d, J 8.3, 1H), 7.21 (s, 1H), 7.30 (d, J 8.3, 1H), 7.67 (d, J 8.3, 1H), 7.86 (d, J 8.3, 1H), 8.05 (s, 1H); MS (ES⁺) m/z 476 (M+H)⁺

REFERENCE EXAMPLE 4

14-cyclohexyl-3-methoxy-6-methyl-5,6,7,8-tetrahydroindolo[2,1-a][2,5]benzodiazocine-11-carboxylic acid Step 1: methyl 2-bromo-3-cyclohexyl-1-(1,3-dioxolan-2-ylmethyl)-1H-indole-6-carboxylate NaH (1.5 eq, 60% dispersion in mineral oil) was added to a solution of methyl 2-bromo-3-cyclohexyl-1H-indole-6-carboxylate (prepared as described in published International Patent application WO 2004/065367, from commercially available methyl indole-6-carboxylate) in DMF (0.1 M) and once effervescence had subsided the solution was stirred at RT for a further 30 min. 2-bromomethyl-1,3-dioxolane (4 eq) and catalytic (0.025 eq) KI were then added and the mixture heated at 50° C. for 36 h. The reaction mixture was then allowed to cool to RT, quenched with aqueous HCl (1 N) and extracted with EtOAc. The organics were washed with aqueous HCl (1 N) (3×), water and brine before being dried over $Na_2SO_4$, filtered and the solvent evaporated in vacuo. Purification was by flash chromatography (10% EtOAc/PE) to give a pale yellow solid that was triturated with $Et_2O$/PE) to afford the title compound as a white solid (69%); MS (ES$^+$) m/z 422 (M+H)$^+$, m/z 424 (M+H)$^+$.

Step 2: methyl 3-cyclohexyl-1-(1,3-dioxolan-2-ylmethyl)-2-(2-formyl-4-methoxyphenyl)-1H-indole-6-carboxylate To a solution of methyl 2-bromo-3-cyclohexyl-1-(1,3-dioxolan-2-ylmethyl)-1H-indole-6-carboxylate in dioxane (0.1 M) was added $Na_2CO_3$ (6 eq, 2 M aqueous solution), 4-methoxy-2-formylphenylboronic acid (2 eq) and bis(triphenylphosphine) palladium(II) dichloride (0.2 eq). The mixture was degassed before being heated at reflux for 30 min. RP-HPLC analysis of the reaction mixture showed starting material persisted. The reaction mixture was allowed to cool and an additional 1 eq of 4-methoxy-2-formylphenylboronic acid and 0.1 eq of bis(triphenylphosphine)palladium(II) dichloride introduced. Heating at reflux was then resumed for a further 30 min. The reaction was allowed to cool to RT and partitioned between water and EtOAc. The aqueous fraction was extracted with EtOAc and the combined organics washed with aqueous HCl (1N), water and brine before being dried over $Na_2SO_4$, filtered and concentrated in vacuo. The crude material was purified by flash chromatography (10-20% gradient EtOAc/PE) to afford the title compound as a yellow foam (72%); MS (ES$^+$) m/z 478 (M+H)$^+$ Step 3: methyl 3-cyclohexyl-1-(1,3-dioxolan-2-ylmethyl)-2-{4-methoxy-2-[(methylamino)methyl]phenyl}-1H-indole-6-carboxylate To a solution of methyl 3-cyclohexyl-1-(1,3-dioxolan-2-ylmethyl)-2-(2-formyl-4-methoxyphenyl)-1H-indole-6-carboxylate in THF (0.05 M), methylamine (10 eq, 2 M solution in THF) was added and the pH adjusted to pH 6 with acetic acid. The solution was stirred at RT for 45 min before being concentrated in vacuo. The residue was taken up in MeOH to give a 0.025 M solution. $NaBH_3CN$ (2.4 eq) was added and the mixture stirred at RT for 2 h. The reaction was quenched with saturated aqueous $NaHCO_3$ and extracted (twice) with EtOAc. The combined organics were washed with water and brine before being dried over $Na_2SO_4$, filtered and concentrated in vacuo to give the title compound as a viscous oil (89%); MS (ES$^+$) m/z 493 (M+H)$^+$ Step 4: methyl 3-cyclohexyl-2-{4-methoxy-2-[(methylamino)methyl]phenyl}-1-(2-oxoethyl)-1H-indole-6-carboxylate Aqueous HCl (25 eq, 3 M) was added to a solution of methyl 3-cyclohexyl-1-(1,3-dioxolan-2-ylmethyl)-2-{4-methoxy-2-[(methylamino)methyl]phenyl}-1H-indole-6-carboxylate in THF (0.02 M), and the mixture heated at reflux for 24 h. The volatiles were reduced in vacuo, and the residue partitioned between EtOAc and saturated aqueous $NaHCO_3$ (ensuring that the aqueous phase is basic). The aqueous phase was extracted with EtOAc and the combined organics washed with water and brine, before being dried ($Na_2SO_4$), filtered and concentrated in vacuo to give the title compound in essentially quantitative yield; MS (ES$^+$) m/z 449 (M+H)$^+$.

Step 5: 14-cyclohexyl-3-methoxy-6-methyl-5,6,7,8-tetrahydroindolo[2,1-a][2,5]benzodiazocine-11-carboxylic acid Acetic acid was added dropwise to a stirred solution of methyl 3-cyclohexyl-2-{4-methoxy-2-[(methylamino)methyl]phenyl}-1-(2-oxoethyl)-1H-indole-6-carboxylate in MeOH (0.005 M) at RT, to adjust the pH to pH 6. The mixture was stirred for 10 min prior to introducing 3.2 eq of NaCNBH$_3$. RP-HPLC analysis of the reaction mixture after 1 h confirmed the complete conversion of the aminoaldehyde to the desired cyclic amine. The reaction was diluted with an equal volume of THF and 100 eq of NaOH (2 M aqueous solution) introduced. The reaction mixture was then heated at 60° C. for 3 h before being allowed to cool to RT. The THF/MeOH volume was reduced in vacuo and the residue acidified with aqueous HCl (1 N) before being extracted with EtOAc (4×). The combined organics were washed with brine, dried over $Na_2SO_4$, filtered and concentrated in vacuo to afford the hydrochloride salt of the product as a yellow solid. Purification was by automated RP-MS-HPLC (stationary phase: column Waters XTERRA prep. C18, 5 um, 19×100 mm. Mobile phase: MeCN/H$_2$O buffered with 0.1% TFA). Fractions containing the pure compound were combined and freeze dried to afford the title compound as a white powder (21%).

$^1$H NMR (400 MHz, DMSO-d$_6$, 300 K) δ 1.09-1.21 (m, 1H), 1.28-1.37 (m, 2H), 1.50-1.56 (m, 1H), 1.65-1.75 (m, 2H), 1.82-2.0 (m, 4H), 2.58-2.67 (m, 1H), 3.04 (br s, 3H), 3.3-3.5 (m, 1H, obscured by water peak), 3.63-3.75 (m, 3H), 3.91 (s, 3H), 4.32 (d, J 13.4, 1H), 4.79 (dd, J 16.0, 3.5, 1H), 7.25 (dd, J 8.5, 2.3, 1H), 7.40 (d, J 8.5, 1H), 7.61 (d, J 2.3, 1H), 7.73 (d, J 8.3, 1H), 7.91 (d, J 8.3, 1H), 8.19 (s, 1H), 9.86 (br s, 1H), 12.68 (br s, 1H); MS (ES$^+$) m/z 419 (M+H)$^+$

EXAMPLE 5 methyl({[(14-cyclohexyl-3-methoxy-6-methyl-5,6,7,8-tetrahydroindolo[2,1-a][2,5]benzodiazocin-11-yl)carbonyl]amino}sulfonyl)acetate 1.6 eq of 1-ethyl-(3-dimethylaminopropyl)carbodiimide HCl salt was added to a mixture of 2.7 eq of DMAP, 1.6 eq of methyl(aminosulfonyl)acetate and the hydrochloride salt of 14-cyclohexyl-3-methoxy-6-methyl-5,6,7,8-tetrahydroindolo[2,1-a][2,5]-benzodiazocine-11-carboxylic acid (from Example 4) in DCM (0.02 M). The reaction was stirred at RT overnight before being partitioned between aqueous HCl (1 N) and EtOAc. The organics were washed with saturated aqueous NaHCO$_3$, water and brine before being dried over Na$_2$SO$_4$, filtered and concentrated in vacuo. The crude was then purified by RP-HPLC (stationary phase: column Waters XTERRA prep. C18, 5 um, 30×50 mm. Mobile phase: MeCN/H$_2$O buffered with 0.1% TFA). Fractions containing the pure compound were combined and freeze dried to afford the title compound as a white powder (18%).

$^1$H NMR (400 MHz, DMSO-d$_6$, 300 K) δ 1.09-1.21 (m, 1H), 1.21-1.42 (m, 2H), 1.50-1.58 (m, 1H), 1.65-1.78 (m, 2H), 1.80-2.0 (m, 4H), 2.58-2.67 (m, 1H), 3.06 (br s, 3H), 3.4-3.55 (m, 1H, obscured by water peak), 3.68 (s, 3H), 3.68-3.78 (m, 3H), 3.91 (s, 3H), 4.34 (d, J 13.4, 1H), 4.68-4.77 (m, 3H), 7.26 (dd, J 8.5, 2.5, 1H), 7.41 (d, J 8.5, 1H), 7.62

(d, J 2.5, 1H), 7.72 (d, J 8.5, 1H), 7.95 (d, J 8.5, 1H), 8.25 (s, 1H), 9.89 (br s, 1H), 12.30 (br s, 1H); MS (ES$^+$) m/z 554 (M+H)$^+$

EXAMPLE 6

({[(14-cyclohexyl-3-methoxy-6-methyl-5,6,7,8-tetrahydroindolo[2,1-a][2,5]benzodiazocin-11-yl)carbonyl]amino}sulfonyl)acetic acid To a solution of methyl({[(14-cyclohexyl-3-methoxy-6-methyl-5,6,7,8-tetrahydroindolo[2,1-a][2,5]benzodiazocin-11-yl)carbonyl]amino}sulfonyl)acetate (from example 5) in dioxane (0.04 M) was added an equal volume of water and 4 eq of NaOH (1 N aqueous solution). The reaction was stirred vigorously at RT for 1 h. The reaction was acidified with aqueous HCl (1 N) and reduced in vacuo to remove dioxane. The resultant aqueous slurry was diluted with MeCN and water and freeze dried to leave a white powder. The crude was then purified by automated RP-MS-HPLC (stationary phase: column Waters XTERRA prep. C18, 5 um, 19×100 mm. Mobile phase: MeCN/H$_2$O buffered with 0.1% TFA). Fractions containing the pure compound were combined and freeze dried to afford the title compound as a white powder (72%).
$^1$H NMR (400 MHz, DMSO-d$_6$, 300 K) δ 1.09-1.20 (m, 1H), 1.24-1.41 (m, 2H), 1.52-1.56 (m, 1H), 1.67-1.75 (m, 2H), 1.82-2.0 (m, 4H), 2.59-2.67 (m, 1H), 3.06 (br s, 3H), 3.3-3.55 (m, 1H, obscured by water peak), 3.65-3.78 (m, 3H), 3.91 (s, 3H), 4.33 (d, J 13.2, 1H), 4.58 (d, J 15.0, 1H), 4.62 (d, J 15.0, 1H), 4.65-4.73 (m, 1H), 7.26 (dd, J 8.5, 2.5, 1H), 7.41 (d, J 8.5, 1H), 7.62 (d, J 2.5, 1H), 7.72 (d, 8.5, 1H), 7.94 (d, J 8.5, 1H), 8.26 (s, 1H), 9.90 (br s, 1H), 12.20 (br s, 1H), 13.41 (br s, 1H); MS (ES$^+$) m/z 540 (M+H)$^+$.

EXAMPLE 7

14-cyclohexyl-N-[(dimethylamino)sulfonyl]-3-methoxy-6-methyl-5,6,7,8-tetrahydroindolo[2,1-a][2,5]benzodiazocine-11-carboxamide 1.5 eq of DMAP was added to the trifluoroacetate salt of 14-cyclohexyl-3-methoxy-6-methyl-5,6,7,8-tetrahydroindolo[2,1-a][2,5]benzodiazocine-11-carboxylic acid (from Example 4) in dry DCM (0.1 M). Then 1.5 eq of EDAC.HCl was added and after 5 min of stirring at RT 1.5 eq of N,N-dimethylsulfamide. The reaction mixture was stirred overnight at RT. The solvent was removed in vacuo and the residue directly purified by RP-MS-HPLC (stationary phase: column Waters XTERRA prep. C18, 5 um, 19×100 mm. Mobile phase: MeCN/H$_2$O buffered with 0.1% TFA). Fractions containing the pure compound were combined and freeze dried to afford the title compound as a white powder (38%).
$^1$H NMR (400 MHz, DMSO-d$_6$, 300 K) δ 1.13-1.36 (m, 3H), 1.95-1.47 (m, 7H), 2.66-2.60 (m, 1H), 2.91 (s, 6H), 3.05 (br s, 3H), 3.50-3.63 (m, 1H), 3.64-3.74 (m, 3H), 3.90 (s, 3H), 4.32 (AB system, J 14.0, 1H), 4.69 (AB system, J 14.0, 1H), 7.25 (d, J 8.3, 1H), 7.40 (d, J 8.3, 1H), 7.61 (s, 1H), 7.70 (d, J 7.9, 1H), 7.92 (d, J 7.9, 1H), 8.25 (s, 1H), 9.9 (br s, 1H), 11.6 (br s, 1H); MS (ES$^+$) m/z 525 (M+H)$^+$

EXAMPLE 8

3-chloro-14-cyclohexyl-6-[2-(dimethylamino)ethyl]-7-oxo-5,6,7,8-tetrahydroindolo[2,1-a][2,5]benzodiazocine 11-carboxylic acid Step 1: 1-bromo-2-(bromomethyl)-4-chlorobenzene 1-bromo-2-(bromomethyl)-4-chlorobenzene was prepared according to literature precedent (J. Am. Chem. Soc. 2002, 124 (7), 1354): a suspension of 1-bromo-2-methyl-4-chlorobenzene (1 eq), NBS (1 eq) and benzoyl peroxide (0.004 eq) in CCl$_4$ (0.7 M) was heated at reflux for 4 h. The reaction was then filtered whilst hot and the volatiles reduced in vacuo. PE was added, and the resultant precipitate filtered off and dried in vacuo to afford the title compound (45%).

Step 2: 2-bromo-5-chlorobenzaldehyde 2-bromo-5-chlorobenzaldehyde was prepared according to literature precedent (J. Am. Chem. Soc. 2002, 124 (7), 1354): a mixture of activated powdered 4A molecular sieves (800 mg/mmol substrate), N-methylmorpholine-N-oxide (2 eq) and 2-bromomethyl-5-chlorobenzaldehyde (1 eq) in MeCN (0.16 M) was stirred at 0° C. for 2 h. The reaction was then filtered through a pad of celite and concentrated in vacuo to afford the title compound (92%)

Step 3: N'-(2-bromo-5-chlorobenzyl)-N,N-dimethylethane-1,2-diamine

To a solution of 2-bromo-5-chlorobenzaldehyde (from Step 2, 1 eq) in THF (0.04 M), N,N-dimethylethane-1,2-diamine (1.2 eq) was added and the pH adjusted to pH 5 with acetic acid. The solution was stirred at RT for 1 h, then the THF was removed in vacuo and the residue taken up in MeOH to give a 0.04 M solution. NaBH$_3$CN (2 eq) was added and the mixture stirred at RT for 3 h. The reaction mixture was diluted with EtOAc and the organic phase washed with a saturated aqueous solution of NaHCO$_3$, H$_2$O and then brine. The organic phase was dried over Na$_2$SO$_4$, filtered and concentrated in vacuo to give the title compound (quant.); MS (ES$^+$) m/z 291 (M+H)$^+$.

Step 4: tert-butyl 3-cyclohexyl-1H-indole-6-carboxylate 2 eq of tert-butyl N,N'-diisopropylimidocarbamate (prepared according to literature precedent: Synthesis 1979, 561) were added to a solution of 3-cyclohexyl-1H-indole-6-carboxylic acid (prepared as described in published International patent application WO2004087714) in CH$_2$Cl$_2$ (0.4 M) and the mixture heated at reflux under N$_2$ for 16 h. A further 2.5 eq of tert-butyl N,N'-diisopropylimidocarbamate were then added portionwise over 3 h, with heating being resumed after each addition. The reaction mixture was then filtered whilst hot through a pad of CELITE and the filtrate concentrated in vacuo. The residue was purified by flash chromatography (5% EtOAc/PE) to afford the title compound (58%); MS (ES$^-$) m/z 298 (M−H)$^-$.

Step 5: tert-butyl 2-bromo-3-cyclohexyl-1H-indole-6-carboxylate

N-bromosuccinimide (1.1 eq) was added portionwise over 1 h to tert-butyl 3-cyclohexyl-1H-indole-6-carboxylate in CCl$_4$ (from Step 4, 0.07 M) with vigorous stirring. The reaction was stirred at RT for a further hour following complete addition of NBS. The CCl$_4$ was then removed in vacuo and the residue taken up in EtOAc. The organics were washed with a saturated aqueous solution of sodium thiosulfate (twice), brine, dried over Na$_2$SO$_4$, filtered and concentrated in vacuo. Purification was by flash chromatography (5-20% EtOAc/PE gradient) to yield the title compound (57%); MS (ES$^+$) m/z 380 (M+H)$^+$, 378 (M+H)$^+$.

Step 6: tert-butyl 2-bromo-3-cyclohexyl-1-(2-methoxy-2-oxoethyl)-1H-indole-6-carboxylate NaH (1.4 eq, 60% dispersion in mineral oil) was added to a solution of tert-butyl 2-bromo-3-cyclohexyl-1H-indole-6-carboxylate in DMF (from Step 5, 0.15 M) and the solution stirred at RT for 30 min. Then methyl bromoacetate (1.4 eq) was added and the mixture stirred at RT for 3 h. The solvent was removed in vacuo and the residue taken up in EtOAc. The organic phase was washed twice with aqueous HCl (0.5 N) and then brine. The organic phase was dried over $Na_2SO_4$, filtered and the solvent evaporated in vacuo. The residue was purified by crystallisation (EtOAc/PE) to afford the title compound (80%); MS (ES$^+$) m/z 450 (M+H)$^+$, m/z 452 (M+H)$^+$.

Step 7: [2-bromo-6-(tert-butoxycarbonyl)-3-cyclohexyl-1H-indol-1-yl]acetic acid

A solution of LiOH monohydrate (4 eq) in $H_2O$ (0.05 M) was added to a solution of tert-butyl 2-bromo-3-cyclohexyl-1-(2-methoxy-2-oxoethyl)-1H-indole-6-carboxylate (1 eq) in a mixture THF:$CH_3OH$ (1:1) (from Step 6, 0.05 M). The reaction was heated at 50° C. for 2 h, before being allowed to cool to RT and reducing the volatiles in vacuo. The residue was then acidified with aqueous HCl (1 N) and the resultant precipitate filtered off, washed with water and dried in vacuo to afford the title compound (quant.); MS (ES$^+$) m/z 436 (M+H)$^+$, 438 (M+H)$^+$.

Step 8: tert-butyl-2-bromo-1-(2-{(2-bromo-5-chlorobenzyl)[2-(dimethylamino)ethyl]amino}-2-oxoethyl)-3-cyclohexyl-1H-indole-6-carboxylate To a solution of [2-bromo-6-(tert-butoxycarbonyl)-3-cyclohexyl-1H-indol-1-yl]acetic acid (from Step 7, 1 eq) in DCM (0.07 M), N'-(2-bromo-5-chlorobenzyl)-N,N-dimethylethane-1,2-diamine (from Step 3, 2.1 eq), DIPEA (3 eq) and HATU (2 eq) were added and the mixture stirred at RT overnight. The solution was diluted with DCM and washed with HCl (1 N), a saturated aqueous solution of $NaHCO_3$ and brine, dried ($Na_2SO_4$), filtered and concentrated in vacuo to afford the title compound (56%) that was used in the next step without further purification; MS (ES$^+$) m/z 710 (M+H)$^+$.

Step 9: tert-butyl-3-chloro-14-cyclohexyl-6-[2-(dimethylamino)ethyl]-7-oxo-5,6,7,8-tetrahydroindolo[2,1-a][2,5]benzodiazocine-11-carboxylate To a Smith PROCESS VIAL™ (2-5 ml) charged with a magnetic stirring bar, tert-butyl-2-bromo-1-(2-{(2-bromo-5-chlorobenzyl)[2-(dimethylamino)ethyl]amino}-2-oxoethyl)-3-cyclohexyl-1H-indole-6-carboxylate (from Step 8, 1 eq) in DMF dry (0.02 M), 4,4,4',4',5,5,5',5'-octamethyl-2,2'-bi-1,3,2-dioxaborolane (1.1 eq), $PdCl_2$(dppf) (0.03 eq) and potassium acetate (3 eq) were added. The vial was closed with its cap and filled with $N_2$ and microwaved in a Smith PERSONAL SYNTHESIZER at 150° C. for 6 min. The solution was then diluted with EtOAc, washed with $H_2O$ and brine, dried over $Na_2SO_4$, filtered and concentrated in vacuo to afford the crude that was filtered through a plug of silica (EtOAc:PE:$Et_3N$) (5:5:0.1%) and used in the next step without further purification; MS (ES$^+$) m/z 550 (M+H)$^+$.

Step 10: 3-chloro-14-cyclohexyl-6-[2-(dimethylamino)ethyl]-7-oxo-5,6,7,8-tetrahydroindolo[2,1-a][2,5]benzodiazocine-11-carboxylic acid A solution of tert-butyl-3-chloro-14-cyclohexyl-6-[2-(dimethylamino)ethyl]-7-oxo-5,6,7,8-tetrahydroindolo[2,1-a][2,5]benzodiazocine-11-carboxylate (from Step 9, 1 eq) in a mixture of TFA:$H_2O$:$Et_3SiH$ (95:3:2) (0.03 M) was stirred at RT for 1 h. Volatiles were removed in vacuo and the residue purified by RP-HPLC to afford the title compound; MS (ES$^+$) m/z 494 (M+H)$^+$.

EXAMPLE 9

N'-(11-carboxy-14-cyclohexyl-7,8-dihydro-6H-indolo[1,2-e][1,5]benzoxazocin-7-yl)-N,N-dimethylethane-1,2-diaminium bis(trifluoroacetate)

Step 1: methyl 3-cyclohexyl-2-(2-hydroxyphenyl)-1H-indole-6-carboxylate

To a solution of methyl 2-bromo-3-cyclohexyl-1H-indole-6-carboxylate (prepared as described in International patent application WO2004087714, from commercially available methyl indole-6-carboxylate) in a mixture of DME and EtOH (5:2, v/v, 0.2 M) were added 2 eq of $Na_2CO_3$ (2 M aqueous solution), 1.3 eq of (2-hydroxyphenyl)boronic acid and 0.1 eq of tetrakis(triphenylphosphine)palladium(0). The mixture was degassed thoroughly with a stream of dry $N_2$ and then heated to 100° C. overnight. The reaction mixture was allowed to cool, diluted with some EtOAc and filtered over a plug of celite. The filtrate was diluted with EtOAc and the organic phase washed with water, brine and dried over $Na_2SO_4$ before being filtered and concentrated in vacuo. The crude material was purified by flash chromatography on silica gel (1:7 EtOAc/PE, then 1:3) to afford the title compound as a light yellow solid (60%); MS (ES$^+$) n/z 350 (M+H)$^+$.

Step 2: methyl 3-cyclohexyl-2-{2-[(2S)-oxiran-2-ylmethoxy]phenyl}-1H-indole-6-carboxylate To a solution of the foregoing product from Step 1 in DMF (0.04 M) were added cesium fluoride (3 eq) and (S)-glycidyl 3-nitrobenzenesulfonate (1.1 eq). The resulting mixture was stirred at RT overnight, then diluted with EtOAc and washed with water and brine. Drying over $Na_2SO_4$, filtration and concentration in vacuo gave the crude product, which was purified by flash chromatography on silica gel (1:5 EtOAc/PE) to afford the title compound as a colourless foam (74%); MS (ES$^+$) m/z 406 (M+H)$^+$; $[\alpha]_D^{20}$=+22 (c=0.5, $CHCl_3$).

Step 3: methyl (7S)-14-cyclohexyl-7-hydroxy-7,8-dihydro-6H-indolo[1,2-e][1,5]benzoxazocine-11-carboxylate A solution of the foregoing product from Step 2 in DMF (0.05 M) was cooled to 0° C. with the help of an ice-bath and solid NaH (1.2 eq, 60% dispersion in mineral oil) was added portionwise. The reaction was allowed to reach RT and stirred for 3 h. The reaction mixture was diluted with EtOAc and washed with HCl (1 N), water and brine. Drying ($Na_2SO_4$), filtration and concentration in vacuo gave the crude product, which was purified by flash chromatography on silica gel (1:4 EtOAc/PE) to afford the title compound, as colourless foam (55%, mixture of diastereomers, 2:1); MS (ES$^+$) m/z 406 (M+H)$^+$; $[\alpha]_D^{20}$=−28 (c=0.5, $CHCl_3$).

Step 4: methyl 14-cyclohexyl-7-oxo-7,8-dihydro-6H-indolo[1,2-e][1,5]benzoxazocine-11-carboxylate To a solution of methyl (7S)-14-cyclohexyl-7-hydroxy-7,8-dihydro-6H-indolo[1,2-e][1,5]benzoxazocine-11-carboxylate (from Step 3) in DCM (0.1 M) was added Dess-Martin periodinane (DMP, 1.2 eq), and the mixture was stirred for 1 h at RT. At this point another 0.6 eq of DMP were added and the reaction left overnight. The reaction mixture was diluted with EtOAc and washed with an aqueous solution of a 1:1 mixture containing sodium thiosulfate and $NaHCO_3$ (both saturated solutions), then with water and brine. Drying over $Na_2SO_4$, filtration and concentration in vacuo gave the crude product, which was used without further purification (90%); MS (ES$^+$) m/z 404 (M+H)$^+$.

Step 5: methyl 14-cyclohexyl-7-{[2-(dimethylamino)ethyl]amino}-7,8-dihydro-6H-indolo[1,2-e][1,5]benzoxazocine-11-carboxylate To a solution of methyl 14-cyclohexyl-7-oxo-7,8-dihydro-6H-indolo[1,2-e][1,5]benzoxazocine-11-carboxylate (from Step 4) in 1,2-dichloroethane (0.08 M), were added 1.0 eq of N,N-dimethylethane-1,2-diamine and 1.5 eq acetic acid, followed by 1.5 eq. of solid sodium triacetoxyborohydride. NaOH (20 eq, 1 N) was added after 2 h, and after stirring for 5 min the mixture was taken into EtOAc and washed with water and brine. Drying over sodium sulfate and concentration in vacuo gave the crude product, which was used without further purification; MS (ES$^+$) m/z 476 (M+H)$^+$.

Step 6: N'-(11-carboxy-14-cyclohexyl-7,8-dihydro-6H-indolo[1,2-e][1,5]benzoxazocin-7-yl)-N,N-dimethylethane-1,2-diaminium bis(trifluoroacetate)

To a solution of the foregoing crude product (from Step 5) in THF/MeOH (0.05 M, 1:1, v/v) was added KOH (8 eq, 1N) and the mixture was stirred at 50° C. The reaction mixture was brought to pH 2 by the dropwise addition of HCl (1 N), then diluted with MeCN and purified by RP-HPLC (stationary phase: column Waters XTERRA prep. C18, 5 um, 19×100 mm. Mobile phase: MeCN/$H_2O$ buffered with 0.1% TFA). Fractions containing the pure compound were combined and freeze dried to afford the title compound as a white powder (60% over two steps).
$^1$H NMR (400 MHz, DMSO-d$_6$, 300 K, 2 diastereomers 7:1*) δ 1.09-1.22 (m, 1H), 1.25-1.46 (m, 2H), 1.50-1.58 (m, 1H), 1.65-1.78 (m, 2H), 1.82-1.88 (m, 1H), 1.89-2.07 (m, 3H), 2.64-2.75 (m, 1H), 2.79*, 2.82 (s, 6H), 2.98-3.10 (m, 1H), 3.10-3.90 (m, 5H, together with water peak and probably the 3 exchangeable protons), 3.96-4.02 (m, 1H), 4.18, 4.32* (dd, J 3.0, 12.6, 1H), 4.74, 4.84* (d, J 11.9, 1H), 7.22-7.28 (m, 2H), 7.30 (dd, J 1.9, 7.9, 1H), 7.52 (dt, J 1.9, 8.5, 1H), 7.64*, 7.70 (dd, J 1.0, 8.4, 1H), 7.86*, 7.99 (d, J 8.5*, 8.4, 1H), 8.22, 8.35* (s, 1H); MS (ES$^+$) m/z 462 (M+H)$^+$

NO EXAMPLE 10

EXAMPLE 11

N-(11-carboxy-14-cyclohexyl-7,8-dihydro-6H-indolo[1,2-e][1,5]benzoxazocin-7-yl)-N,N',N'-trimethylethane-1,2-diaminium bis(trifluoroacetate)

Step 1: methyl 14-cyclohexyl-7-[[2-(dimethylamino)ethyl](methyl)amino]-7,8-dihydro-6H-indolo[1,2-e][1,5]benzoxazocine-11-carboxylate To a solution of methyl 14-cyclohexyl-7-{[2-(dimethylamino)ethyl]amino}-7,8-dihydro-6H-indolo[1,2-e][1,5]benzoxazocine-11-carboxylate (prepared as described in Example 9, Step 5) in DCM (0.1 M), was added formaldehyde (3.0 eq) and acetic acid (5.5 eq), followed by sodium cyanoborohydride (3 eq). NaOH (20 eq, 1 N) was added after 2 h, and after stirring for 5 min the mixture was taken into EtOAc and washed with water and brine. Drying over sodium sulfate and concentration in vacuo gave the crude product, which was used without further purification; MS (ES$^+$) m/z 490 (M+H)$^+$.

Step 2: N-(11-carboxy-14-cyclohexyl-7,8-dihydro-6H-indolo[1,2-e][1,5]benzoxazocin-7-yl)-N,N',N'-trimethylethane-1,2-diaminium bis(trifluoroacetate)

To a solution of the foregoing product (from step 1) in dioxane/water (0.06 M, 2:1, v/v) were added 5 eq. of potassium hydroxide and the mixture was stirred at 80° C. The reaction mixture was brought to pH 2 by the drop wise addition of hydrochloric acid (1 N), then diluted with MeCN and purified by RP-HPLC (stationary phase: column Waters SYMMETRY prep. C18, 7 um, 19×150 mm. Mobile phase: MeCN/$H_2O$ buffered with 0.1% TFA). Fractions containing the pure compound were combined and freeze dried to afford the title compound as a white powder (45% over three steps).
$^1$H NMR (400 MHz, DMSO, 300 K, 2 diastereomers 94:6) δ1.09-1.25 (m, 1H), 1.26-1.43 (m, 2H), 1.54 (d, J 12.2, 1H), 1.62-1.78 (m, 2H), 1.79-2.06 (m, 4H), 2.39 (s, 3H), 2.61 (s, 0.36H), 2.65-2.77 (m, 1H), 2.85 (s, 5.64H), 2.94 (dt, J 5.5, 13.6, 1H), 3.04-3.15 (m, 2H), 3.18 (dt, J 5.6, 13.0, 1H), 3.23-3.34 (m, 1H), 3.74-3.80 (m, 0.06H partially overlapped with the signal at 3.85 ppm), 3.85 (dd, J10.2, 14.4, 0.94 H), 4.07 (dd, J 9.0, 12.1, 0.94H), 4.11-4.17 (m, 0.06H partially overlapped with signal at 4.07 ppm), 4.31 (dd, J 4.3, 12.1, 0.94H), 4.64 (d, J 14.4, 0.94H), 4.75 (d, J 13.1, 0.06H), 4.79-4.87 (m, 0.06H), 7.24-7.37 (m, 3H), 7.50-7.59 (m, 1H), 7.63-7.66 (m, 0.06 partially overlapped with signal at 7.69), 7.69 (dd, J 0.8, 8.3, 0.94H), 7.82-7.85 (m, 0.06H partially overlapped with dd at 7.87 ppm), 7.87 (d, J 8.3, 0.94H), 8.15 (s, 0.94H), 8.32 (s, 0.06H). MS (ES$^+$) m/z 476 (M+H)$^+$.

EXAMPLE 12

N'-[(7R)-11-carboxy-14-cyclohexyl-7,8-dihydro-6H-indolo[1,2-e][1,5]benzoxazocin-7-yl]-N,N,N'-trimethylethane-1,2-diaminium bis(trifluoroacetate)

Step 1: methyl (7S)-14-cyclohexyl-7-{[(4-methylphenyl)sulfonyl]oxy}7,8-dihydro-6H-indolo[1,2-e][1,5]benzoxazocine-11-carboxylate To a solution of methyl (7S)-14-cyclohexyl-7-hydroxy-7,8-dihydro-6H-indolo[1,2-e][1,5]benzoxazocine-11-carboxylate (prepared as described in Example 9, Step 3) in pyridine (0.08M) tosyl chloride (2.5 eq.) was added and the reaction was stirred at RT overnight. The reaction mixture was diluted with EtOAc and washed with HCl (1 N), $NaHCO_3$ (saturated solutions) and brine. Drying over $Na_2SO_4$, filtration and concentration in vacuo gave the crude product, which was purified by flash chromatography (1:9 EtOAc/PE) to afford the title compound as pale yellow oil (94%); MS (ES$^+$) m/z 560 (M+H)$^+$.

Step 2: methyl (7R)-7-azido-14-cyclohexyl-7,8-dihydro-6H-indolo[1,2-e][1,5]benzoxazocine-11-carboxylate To a solution of the foregoing product from step 1 in dry THF (0.06 M) azidotrimethylsilane (3.5 eq.) and tetrabutylammonium triphenyldifluorosilicate (3.5 eq.) were added. The reaction was stirred for 20 h at 65° C. then 1 more eq. of azidotrimethylsilane was added and the mixture stirred at 65° C. for 36 h. The volatiles were evaporated in vacuo and the crude dissolved in EtOAc was washed with hydrochloric acid (1 N), sodium hydrogen carbonate (saturated solutions) and brine. Drying over $Na_2SO_4$, filtration and concentration in vacuo gave the crude product, which was purified by flash chromatography on silica gel (5:95 EtOAc/PE) to afford the title compound as white foam (84%); MS (ES$^+$) m/z 431 (M+H)$^+$.

Step 3: methyl (7R)-7-amino-14-cyclohexyl-7,8-dihydro-6H-indolo[1,2-e][1,5]benzoxazocine-11-carboxylate A solution of the foregoing product from Step 2 in MeOH (0.1 M) containing palladium on charcoal (10%, w/w) was stirred under hydrogen at atmospheric pressure for 4 h. The catalyst was filtered off and the solution was concentrated to dryness under reduced pressure to afford the title compound (92%) MS (ES$^+$) m/z 405 (M+H)$^+$. MS (ES$^+$) m/z 405 (M+H)$^+$; %; $[\alpha]_D^{20}$=+46.4 (c=1, CHCl$_3$).

Step 4: methyl (7R)-7-({2-[(tert-butoxycarbonyl)amino]ethyl}amino)-14-cyclohexyl-7,8-dihydro-6H-indolo[1,2-e][1,5]benzoxazocine-11-carboxylate To a solution of the foregoing product from Step 3 in dry trimethyl orthoformate (0.35 M) tert-butyl N-(2-oxoethyl)carbamate (1.05 eq.) was added and the mixture was stirred at RT overnight. The solution was concentrated to dryness under reduced pressure and the crude dissolved in dry MeOH (0.25 M) was treated with HOAc eq.) and sodium cyanoborohydride (1.5 eq.). The mixture was stirred at RT for 1 h. NaOH (20 eq, 1 N) was added, and after stirring for 5 min the mixture was taken into EtOAc and washed with water and brine. Drying over sodium sulfate and concentration in vacuo gave the crude product, which was purified by flash chromatography (1:4 EtOAc+0.1% NEt$_3$/PE+0.1% NEt$_3$, then 6/4) to afford the title compound as white foam (46%); MS (ES$^+$) m/z 548 (M+H)$^+$.

Step 5: methyl (7R)-13-cyclohexyl-7-[[2-(dimethylamino)ethyl](methyl)amino]-6,7,8,8a-tetrahydrobenzo[b]indeno[2,1-d]oxocine-10-carboxylate The foregoing product from Step 4 was dissolved (0.08 M) in a mixture 3/1 DCM/TFA and the mixture was stirred at RT. The solution was concentrated to dryness under reduced pressure. To the crude product dissolved in DCM (0.2 M) 6 eq. of sodium acetate, 6 eq. of formaldehyde and 6 eq. of sodium cyanoborohydride were added. NaOH (20 eq, 1 N) was added after 1 h, and after stirring for 5 min the mixture was taken into EtOAc and washed with brine. Drying over sodium sulfate and concentration in vacuo gave the crude product, which was used without any further purification; MS (ES$^+$) m/z 490 (M+H)$^+$.

Step 6: N'-[(7R)-11-carboxy-14-cyclohexyl-7,8-dihydro-6H-indolo[1,2-e][1,5]benzoxazocin-7-yl]-N,N,N'-trimethylethane-1,2-diaminium bis(trifluoroacetate)

To a solution of the crude product (from Step 5) in dioxane/water (0.06 M, 2:1, v/v) was added 5 eq. of potassium hydroxide and the mixture was stirred at 80° C. The reaction mixture was brought to pH 2 by the dropwise addition of hydrochloric acid (1 N), then diluted with MeCN and purified by RP-HPLC (stationary phase: column Waters SYMMETRY prep. C18, 7 um, 19×300 mm. Mobile phase: MeCN/H$_2$O buffered with 0.1% TFA). Fractions containing the pure compound were combined and freeze dried to afford the title compound as a white powder (41% over two steps). The $^1$H NMR and MS spectra of the title compound are the same reported for the racemate (see example 10 step 2). e.e.>96%; $[\alpha]_D^{20}$=+36.8 (c=0.5, CHCl$_3$).

EXAMPLE 13

N'-[(7S)-11-carboxy-14-cyclohexyl-7,8-dihydro-6H-indolo[1,2-e][1,5]benzoxazocin-7-yl]-N,N,N'-trimethylethane-1,2-diaminium bis(trifluoroacetate)

The title compound was obtained with the same procedure described for its enantiomer (7R) (see Example 12) using R)-glycidyl 3-nitrobenzenesulfonate instead of (S)-glycidyl 3-nitrobenzenesulfonate for Example 9, Step 2, giving methyl 3-cyclohexyl-2-{2-[(2R)-oxiran-2-ylmethoxy]phenyl}-1H-indole-6-carboxylate: $[\alpha]_D^{20}$=−19.8 (c=0.5, CHCl$_3$) and after cyclization methyl (7R)-14-cyclohexyl-7-hydroxy-7,8-dihydro-6H-indolo[1,2-e][1,5]benzoxazocine-11-carboxylate: $[\alpha]_D^{20}$=+29.9 (c=0.54, CHCl$_3$), which was converted to the title compound as described in Example 12. The $^1$H NMR and MS spectra of the title compound are the same reported for the racemate (see example 11): e.e.>99%; $[\alpha]_D^{20}$=−40 (c=0.1, CHCl$_3$).

EXAMPLE 14

(±)1-(11-carboxy-14-cyclohexyl-7,8-dihydro-6H-indolo[1,2-e][1,5]benzoxazocin-7-yl)-4-methylpiperazinediium bis(trifluoroacetate)

Step 1: methyl 14-cyclohexyl-7-(4-methylpiperazin-1-yl)-7,8-dihydro-6H-indolo[1,2-e][1,5]benzoxazocine-11-carboxylate To a solution of methyl 14-cyclohexyl-7-oxo-7,8-dihydro-6H-indolo[1,2-e][1,5]benzoxazocine-11-carboxylate (prepared as described in Example 9, Step 4) in DCM (0.04 M), were added 3.0 eq of 1-methylpiperazine and 4.5 eq acetic acid, followed by 1.5 eq. of solid sodium triacetoxyborohydride. NaOH (20 eq, 1 N) was added after 2 h, and after stirring for 5 min the mixture was taken into EtOAc and washed with water and brine. Drying over sodium sulfate and concentration in vacuo gave the crude product, which was used without any further purification; MS (ES$^+$) m/z 488 (M+H)$^+$.

Step 2: 1-(11-carboxy-14-cyclohexyl-7,8-dihydro-6H-indolo[1,2-e][1.5]benzoxazocin-7-yl)-4-methylpiperazinediium bis(trifluoroacetate)

The foregoing methyl 14-cyclohexyl-7-(4-methylpiperazin-1-yl)-7,8-dihydro-6H-indolo[1,2-e][1,5]benzoxazocine-11-carboxylate (from step 1) was hydrolyzed to the corresponding acid and purified using the same conditions employed in Example 11, Step 2. The title compound was obtained as a white powder (10% over two steps).
$^1$H NMR (400 MHz, pyridine-d$_5$, 300 K, 2 diastereomers 7:3) δ0.96-1.12 (m, 1H), 1.20-1.43 (m, 2H), 1.55-1.75 (m, 3H), 1.77-1.91 (m, 1H), 2.00-2.23 (m, 3H), 2.28-2.43 (m, 4H), 2.51-2.87 (m, 6H), 2.88-3.07 (m, 3H), 3.69 (d, J 14.5, 0.3H), 3.92 (dd, J 10.6, 14.4, 0.7H), 3.97-4.02 (m, 0.3H), 4.11 (dd, J 7.8, 12.4, 0.7H), 4.27 (dd, J 4.1, 12.4, 0.7H), 4.60-4.67 (m, 0.3H), 4.70 (d, J 14.5, 0.7H), 4.73-4.77 (m, 0.3H), 7.25-7.37 (m, 2H), 7.45-7.53 (m, 2H), 8.09 (d, J 8.6, 0.3H), 8.15 (d, J 8.3, 0.7H), 8.39 (d, J 8.7, 0.3H), 8.48 (d, J 8.3, 0.7H), 8.71 (s, 0.7H together with pyridine peak), 8.94 (s, 0.3H). MS (ES$^+$) m/z 474 (M+H)$^+$.

EXAMPLE 15

(+)1-(11-carboxy-14-cyclohexyl-7,8-dihydro-6H-indolo[1,2-e][1,5]benzoxazocin-7-yl)-4-methylpiperazinediium bis(trifluoroacetate) and (−)1-(11-carboxy-14-cyclohexyl-7,8-dihydro-6H-indolo[1,2-e][1, 5]benzoxazocin-7-yl)-4-methylpiperazinediium bis (trifluoroacetate)

The title compounds were obtained by resolution of the racemate (synthesized as described in example 14) with chiral HPLC (stationary phase: column, CHIRALPAK AD, amilose carbamate, 10 μm, 20×250 mm. Mobile phase: n-hexane/97% EtOH, 3% MeOH buffered with 0.2% TFA).

First enantiomer eluted: (−)1-(11-carboxy-14-cyclohexyl-7,8-dihydro-6H-indolo[1,2-e][1,5]benzoxazocin-7-yl)-4-methylpiperazinediium bis(trifluoroacetate); $^1$H NMR and MS spectra as for the racemate (see example 14 step 2).). e.e.>99%; $[\alpha]_D^{20}$=−62 (c=0.1, CHCl$_3$).

Second enantiomer eluted: (+)1-(11-carboxy-14-cyclohexyl-7,8-dihydro-6H-indolo[1,2-e][1,5]benzoxazocin-7-yl)-4-methylpiperazinediium bis(trifluoroacetate); $^1$H NMR and MS spectra as for the racemate (see example 14 step 2). e.e.>99%; $[\alpha]_D^{20}$=+62 (c=0.1, CHCl$_3$).

EXAMPLE 16

(±)-1-{2-[(11-carboxy-14-cyclohexyl-7,8-dihydro-6H-indolo[1,2-e][1,5]benzoxazocin-7-yl)(methyl) ammonio]ethyl}pyrrolidinium bis(trifluoroacetate)

Step 1: methyl 14-cyclohexyl-7-[(2-pyrrolidin-1-ylethyl)amino]-7,8-dihydro-6H-indolo[1,2-e][1,5] benzoxazocine-11-carboxylate To a solution of methyl 14-cyclohexyl-7-oxo-7,8-dihydro-6H-indolo[1,2-e][1,5]benzoxazocine-11-carboxylate (prepared as described in Example 9, Step 4) in 1,2-dichloroethane (0.11 M), was added 1.3 eq of (2-pyrrolidin-1-ylethyl) amine and 1.5 eq of HOAc, followed by 1.5 eq. of solid sodium triacetoxyborohydride. Sat. aq. NaHCO$_3$ and CH$_2$Cl$_2$ were added after 2 h. The organic phase was separated, washed with brine, dried over Na$_2$SO$_4$, filtered and concentrated in vacuo giving the crude product, which was used without further purification; MS (ES$^+$) m/z 502 (M+H)$^+$.

Step 2: methyl 14-cyclohexyl-7-[methyl(2-pyrrolidin-1-ylethyl)amino]-7,8-dihydro-6H-indolo[1,2-e] [1,5]benzoxazocine-11-carboxylate To a solution of the foregoing crude product (from Step 2) in MeOH (0.06 M), were added 3.5 eq of formaldehyde (37% w/w in water) and 1.2 eq of HOAc, followed by 1.7 eq. of sodium cyanoborohydride. The reaction mixture was concentrated in vacuo and sat. aq. NaHCO$_3$ and CH$_2$Cl$_2$ were added after 1.5 h. The organic phase was separated, dried over Na$_2$SO$_4$, filtered and concentrated in vacuo giving the crude product, which was used without further purification; MS (ES$^+$) m/z 516 (M+H)$^+$.

Step 3: (±)-1-{2-[(11-carboxy-14-cyclohexyl-7,8-dihydro-6H-indolo[1,2-e][1,5]benzoxazocin-7-yl) (methyl)ammonio]ethyl}pyrrolidinium bis(trifluoroacetate)

To a solution of the foregoing crude product (from Step 3) in THF/MeOH (0.01 M, 1:1, v/v) was added KOH (7 eq, 1N) and the mixture was stirred at 60° C. After 14 h, KOH (5 eq, 1N) was added and the mixture was stirred at 60° C. for further 4 h. The reaction mixture was concentrated in vacuo, redissolved with DMSO and purified by RP-HPLC (stationary phase: column Waters XTERRA prep. C18, 5 um, 19×100 mm. Mobile phase: MeCN/H$_2$O buffered with 0.1% TFA). Fractions containing the pure compound were combined and freeze dried to afford the title compound as a white powder (54%).

$^1$H NMR (400 MHz, DMSO-d$_6$, 300 K) δ 1.10-1.42 (m, 3H), 1.45-1.56 (m, 1H), 1.63-1.77 (m, 2H), 1.80-1.88 (m, 1H), 1.88-2.05 (m, 7H), 2.37 (s, 3H), 2.61-2.74 (m, 1H), 2.83-2.95 (m, 1H), 3.00-3.45 (m, 8H), 3.83 (dd, J 10.2, 14.6, 1H), 4.07 (t, J 11.0, 1H), 4.35 (dd, J 4.3, 11.9, 1H), 4.67 (d, J 14.7, 1H), 7.27-7.35 (m, 3H), 7.55 (t, J 7.1, 1H), 7.68 (d, J 8.3, 1H), 7.88 (d, J 8.6, 1H), 8.17 (s, 1H), 9.27 (brs, 2H, NH), 12.57 (brs, 1H, OH); MS (ES$^+$) m/z 504 (M+H)$^+$.

EXAMPLE 17

(+)- and (−)-1-{2-[(11-carboxy-14-cyclohexyl-7,8-dihydro-6H-indolo[1,2-e][1,5]benzoxazocin-7-yl) (methyl)ammonio]ethyl}pyrrolidinium bis(trifluoroacetate)

The title compounds were obtained by resolution of (±)-1-{2-[(11-carboxy-14-cyclohexyl-7,8-dihydro-6H-indolo[1,2-e][1,5]benzoxazocin-7-yl)(methyl)ammonio]-ethyl}pyrrolidinium bis(trifluoroacetate) by HPLC (stationary phase: column CHIRALPAK AD, 20×250 mm. Mobile phase: n-hexane/isopropylalcohol buffered with 0.2% TFA).

First enantiomer eluted: $[\alpha]_D^{20}$=−31.8 (c=0.41, CHCl$_3$); $^1$H NMR and MS as for (±)-1-{2-[(11-carboxy-14-cyclohexyl-7,8-dihydro-6H-indolo[1,2-e][1,5]benzoxazocin-7-yl)(methyl)ammonio]ethyl}pyrrolidinium bis(trifluoroacetate).

Second enantiomer eluted: $[\alpha]_D^{20}$=+31.6 (c=0.40, CHCl$_3$); $^1$H NMR and MS as for (±)-1-{2-[(11-carboxy-14-cyclohexyl-7,8-dihydro-6H-indolo[1,2-e][1,5]benzoxazocin-7-yl)(methyl)ammonio]ethyl}pyrrolidinium bis(trifluoroacetate).

EXAMPLE 18

14-cyclohexyl-6-(N,N-dimethylglycyl)-3-fluoro-5,6, 7,8-tetrahydroindolo[2,1-a][2,5]benzodiazocine-11-carboxylic acid

Step 1: methyl 2-(2-{[(tert-butoxycarbonyl)amino] methyl}-4-fluorophenyl)-3-cyclohexyl-1H-indole-6-carboxylate To a solution of methyl 2-bromo-3-cyclohexyl-1H-indole-6-carboxylate (prepared as described in published International patent application WO2004/087714, from commercially available methyl indole-6-carboxylate) in dioxane (0.07 M) was added 0.2 eq of bis(triphenylphosphine)palladium(II) dichloride at RT under a nitrogen atmosphere. Then aqueous Na$_2$CO$_3$ (2 M solution, 2 eq.) and [2-(N-tert-butoxycarbonyl-amino-methyl)-4-fluorophenyl]-boronic acid (2 eq.) were added and the reaction flask immersed in a preheated oil bath at 100° C. for 2 h. The reaction mixture was allowed to cool and filtered. The filtrate was diluted with DCM and the organic phase washed with H$_2$O, brine and dried over Na$_2$SO$_4$ before being filtered and concentrated in vacuo. The crude material was purified by flash chromatography (1:9 EtOAc/PE) to afford the title compound as a solid (87%); MS (ES$^+$) m/z 481 (M+H)$^+$.

Step 2: methyl 2-(2-tert-butoxycarbonyl)amino]methyl}-4-fluorophenyl)-3-cyclohexyl-1-(2-methoxy-2-oxoethyl)-1H-indole-6-carboxylate Methyl bromoacetate (4 eq) was added to a mixture of methyl 2-(2-{[(tert-butoxycarbonyl)amino]methyl}-4-fluorophenyl)-3-cyclohexyl-1H-indole-6-carboxylate (1 eq., from Step 1) and K$_2$CO$_3$ (6 eq) in dry DMSO (0.2 M). The mixture was stirred at 60° C. for 48 h. At this time the reaction was allowed to cool to RT, diluted with EtOAc. The organic phase was washed with H$_2$O (twice), 1 N HCl and then brine. The organic phase was dried over Na$_2$SO$_4$, filtered and the solvent evaporated in vacuo. The residue was purified by flash chromatography (8 EtOAc/PE); to afford the title compound (68%); MS (ES$^+$) m/z 553 (M+H)$^+$.

Step 3: methyl 2-[2-(aminomethyl)-4-fluorophenyl]-3-cyclohexyl-1-(2-methoxy-2-oxoethyl)-1H-indole-6-carboxylate To methyl 2-(2-tert-butoxycarbonyl)amino]methyl}-4-fluorophenyl)-3-cyclohexyl-1-(2-methoxy-2-oxoethyl)-1H-indole-6-carboxylate (from Step 2), a DCM/TFA solution (1:1; 0.05 M) was added at 0° C. and the solution was stirred at RT for 30 min. The volatiles were removed in vacuo, and the residue diluted with EtOAc. The organic phase was washed with saturated aqueous NaHCO$_3$ (2×), then brine. The organic phase was dried (Na$_2$SO$_4$), filtered and the solvent evaporated in vacuo to afford the title compound (quant.); MS (ES$^+$) m/z 453 (M+H)$^+$.

Step 4: methyl 14-cyclohexyl-3-fluoro-7-oxo-5,6,7,8-tetrahydroindolo[2,1-a][2,5]benzodiazocine-11-carboxylate To a solution of methyl 2-[2-(aminomethyl)-4-fluorophenyl]-3-cyclohexyl-1-(2-methoxy-2-oxoethyl)-1H-indole-6-carboxylate (1 eq., from Step 3) in dry MeOH (0.05 M), 10% in weight of sodium methoxide was added and the mixture stirred at RT overnight. The volume of the solution was reduced in vacuo, before diluting with EtOAc. The organic phase was washed with HCl 1 N and brine, before being dried over Na$_2$SO$_4$, filtered and the solvent evaporated in vacuo to afford the title compound. The crude was used in the next step without further purification (83%); MS (ES$^+$) m/z 421 (M+H)$^+$.

Step 5: methyl 14-cyclohexyl-3-fluoro-5,6,7,8-tetrahydroindolo[2,1-a][2,5]benzodiazocine-11-carboxylate To a solution of methyl 14-cyclohexyl-3-fluoro-7-oxo-5,6,7,8-tetrahydroindolo[2,1-a][2,5]benzodiazocine-11-carboxylate (from Step 4) in THF (0.02 M), BH$_3$.THF (5 eq, 1 M solution in THF) was added and the solution stirred at RT for 2 h. MeOH (0.02 M) and a 1.25 M solution HCl in MeOH (0.24 M) were added carefully and left overnight to stir at RT before reducing the volume of the volatiles in vacuo and diluting with EtOAc. The organic phase was washed with aqueous NaHCO$_3$ solution and brine, before being dried over Na$_2$SO$_4$, filtered and the solvent evaporated in vacuo to afford the title compound. The crude was used in the next step without further purification (quant); MS (ES$^+$) m/z 407 (M+H)$^+$.

Step 6: methyl 14-cyclohexyl-6-(N,N-dimethylglycyl)-3-fluoro-5,6,7,8-tetrahydroindolo[2,1-a][2.5]benzodiazocine-11-carboxylate To a solution of methyl 14-cyclohexyl-3-fluoro-5,6,7,8-tetrahydroindolo[2,1-a][2,5]benzodiazocine-11-carboxylate (from Step 5) in DCM (0.15 M), DIPEA (4 eq.), dimethylglycine (3 eq.) and HATU (2 eq.) were added and the mixture stirred at RT overnight. The solution was diluted with DCM and HCl (1N) and the 2 phases separated. The aqueous phase was extracted with DCM (twice). The combined organic phases were then washed with a saturated aqueous solution of NaHCO$_3$ and brine before being dried (Na$_2$SO$_4$), filtered and concentrated in vacuo. The crude was used in the next step without further purification; MS (ES$^+$) m/z 492 (M+H)$^+$.

Step 7: 14-cyclohexyl-6-(N,N-dimethylglycyl)-3-fluoro-5,6,7,8-tetrahydroindolo[2,1-a][2.5]benzodiazocine-11-carboxylic acid To a solution of methyl 14-cyclohexyl-6-(N,N-dimethylglycyl)-3-fluoro-5,6,7,8-tetrahydroindolo[2,1-a][2,5]benzodiazocine-11-carboxylate from (Step 6) in DCM (0.15 M) was added dropwise to a solution of BBr$_3$ in DCM (1 M, 5 eq.). The solution was stirred at RT for 1 h. Some drops of saturated aqueous NaHCO$_3$ were added before volatiles were removed in vacuo. The crude was then purified by automated RP-MS-HPLC (stationary phase: column Waters XTERRA prep. C18, 5 μm, 19×100 mm. Mobile phase: MeCN/H$_2$O buffered with 0.1% TFA). Fractions containing the pure compound were combined and freeze dried to afford the title compound as a white powder (28%).
$^1$H NMR (400 MHz, DMSO-d$_6$, 300 K) δ 1.12-1.1.32 (m, 3H), 1.51-1.54 (m, 1H), 1.66-1.72 (m, 2H), 1.81-1.96 (m, 4H), 2.51-2.53 (m, 1H), 2.77 (s, 6H), 3.32-3.39 (m, 2H), 3.65 (dd, J 15.6, 10.0, 1H), 3.92 (dd, J 14.8, 4.0, 1H), 4.13 (d, J 16.0, 1H), 4.34 (d, J 16.0, 1H), 4.74 (d, J 15.6, 4.0, 1H), 5.11 (d, J 14.4, 1H), 7.34-7.40 (m, 1H), 7.46 (dd, J 8.4, 6.0, 1H), 7.60 (dd, J 9.8, 2.7, 1H), 7.71 (d, J 8.4, 1.2, 1H), 7.91 (d, J 8.4, 1H), 8.17 (d, J 1.2, 1H), 9.6 (br s, 1H), 12.7 (br s, 1H); MS (ES$^+$) m/z 478 (M+H)$^+$.

EXAMPLE 19

14-cyclohexyl-6-[2-(dimethylamino)ethyl]-3-fluoro-5,6,7,8-tetrahydroindolo[2,1-a][2,5]benzodiazocine-11-carboxylic acid Step 1: methyl 14-cyclohexyl-6-[2-(dimethylamino)ethyl]-3-fluoro-5,6,7,8-tetrahydroindolo[2,1-a][2.5]benzodiazocine-11-carboxylate To a solution of methyl 14-cyclohexyl-6-(N,N-dimethylglycyl)-3-fluoro-5,6,7,8-tetrahydroindolo[2,1-a][2,5]benzodiazocine-11-carboxylate, obtained as described in Example 18, Step 6, in THF (0.02 M), BH$_3$.THF (5 eq, 1 M solution in THF) was added and the solution stirred at RT for 2 h. MeOH (0.02 M) and a 1.25 M solution HCl in MeOH (0.24 M) were added carefully and left overnight to stir at RT before reducing the volume of the solution in vacuo. The residue was diluted with EtOAc. The organic phase was washed with saturated aqueous NaHCO$_3$ and brine. The organic phase was dried over Na$_2$SO$_4$, filtered and the solvent evaporated in vacuo to afford the title compound. The crude was used in the next step without further purification (quant); MS (ES$^+$) m/z 478 (M+H)$^+$.

Step 2: 14-cyclohexyl-6-[2-(dimethylamino)ethyl]-3-fluoro-5,6,7,8-tetrahydroindolo[2,1-a][2,5]benzodiazocine-11-carboxylic acid The crude methyl 14-cyclohexyl-6-[2-(dimethylamino)ethyl]-3-fluoro-5,6,7,8-tetrahydroindolo[2,1-a][2,5]benzodiazocine-11-carboxylate (from Step 1) was dissolved in a solution THF: MeOH (1:1) (0.02 M) and to that solution 7 eq of an aqueous solution of NaOH (1N) were added. The solution was stirred at 60° C. for 3 h. The solvent was evaporated in vacuo. The crude was then purified by automated RP-MS-HPLC (stationary phase: column Waters XTERRA prep. C18, 5 um, 19×100 mm. Mobile phase: MeCN/H$_2$O buffered with 0.1% TFA). Fractions containing the pure compound were combined and freeze dried to afford the title compound as a white powder (12%).
$^1$H NMR (400 MHz, DMSO-d$_6$+TFA, 300 K) δ 1.08-1.35 (m, 4H), 1.55-1.67 (m, 1H), 1.69-1.77 (m, 2H), 1.81-1.84 (m, 1H), 1.90-1.94 (m, 2H), 2.50-2.57 (m, 1H), 2.86 (s, 6H), 3.30-3.37 (m, 1H), 3.56-3.75 (m, 7H), 4.27-4.31 (m, 1H), 4.76-4.81 (m, 1H), 7.51-7.52 (m, 2H), 7.73 (dd, J 8.4, 1.2, 1H), 7.78-7.81 (m, 1H), 7.92 (d, J 8.4, 1H), 8.17 (d, J 1.2, 1H); MS (ES$^+$) m/z 464 (M+H)$^+$.

EXAMPLE 20

14-cyclohexyl-6-[2-(dimethylamino)ethyl]-5,6,7,8-tetrahydroindolo[2,1-a][2,5]benzodiazocine-11-carboxylic acid Step 1: Methyl 2-bromo-3-cyclohexyl-1-(2,2-dimethoxyethyl)-1H-indole-6-carboxylate To a stirred solution of methyl 2-bromo-3-cyclohexyl-1H-indole-6-carboxylate (prepared as described in published International patent application WO2004/087714) (0.2 M, 1 eq.) in DMF at RT was added NaH (60% dispersion in mineral oil, 1.75 eq). After 1 h, KI (8 mol %) and bromoacetaldehyde dimethyl acetal (2.5 eq) were added and the reaction heated at 80° C. for 17 h. After cooling to RT, the reaction was quenched by addition of aqueous HCl (1N) and extracted into EtOAc (×3). The combined organics were washed with HCl (1N), H$_2$O and brine before being dried (Na$_2$SO$_4$), filtered and concentrated in vacuo. Purification by flash column chromatography (Biotage, 5-10% EtOAc/PE gradient) gave the title compound as a white solid (79%); MS (ES$^+$) m/z 446 (M+H)$^+$, 448 (M+H)$^+$.

Step 2: Methyl 3-cyclohexyl-1-(2,2-dimethoxyethyl)-2-(2-formylphenyl)-1H-indole-6-carboxylate A solution of methyl 2-bromo-3-cyclohexyl-1-(2,2-dimethoxyethyl)-1H-indole-6-carboxylate (0.16 M, 1 eq, from Step 1) in dioxane and Na$_2$CO$_3$ (6 eq of a 2M solution) was degassed by sonication for 10 min. 2-Formylphenylboronic acid (1.5 eq) and bis(triphenylphosphine) palladium(II) dichloride (20 mol %) were added and the reaction placed in a pre-heated oil bath at 108° C. for 20 min. After cooling to RT, the reaction was partitioned between H$_2$O and EtOAc (×3). The combined organics were washed with HCl (1N), H$_2$O, and brine before being dried over Na$_2$SO$_4$, filtered and concentrated in vacuo. Purification by flash column chromatography (Biotage, 10% EtOAc/PE) gave the title compound as a pale yellow solid (85%); MS (ES$^+$) m/z 472 (M+Na)$^+$, 450 (M+H)$^+$.

Step 3: Methyl 3-cyclohexyl-1-(2,2-dimethoxyethyl)-2-[2-({[2-(dimethylamino)ethyl]amino}methyl)phenyl]-1H-indole-6-carboxylate To a stirred solution of methyl 3-cyclohexyl-1-(2,2-dimethoxyethyl)-2-(2-formylphenyl)-1H-indole-6-carboxylate (0.16 M, 1 eq, from Step 2) and 2-dimethylaminoethylamine (2 eq) in THF was added glacial acetic acid to adjust the pH of the reaction to ca. pH 4. The reaction was stirred for 1 h after which the THF was removed under reduced pressure and the residue redissolved in MeOH. NaBH$_4$ (8 eq) was added portionwise until complete conversion was observed by LC-MS analysis. The reaction was quenched by addition of sat. aq. NaHCO$_3$ and extracted into EtOAc (×3). The combined organics were washed with H$_2$O and brine before being dried (Na$_2$SO$_4$), filtered and concentrated in vacuo. The title compound was obtained as a pale yellow oil and taken on without further purification (quantitative); MS (ES$^+$) m/z 522 (M+H)$^+$.

Step 4: Methyl 14-cyclohexyl-6-[2-(dimethylamino)ethyl]-5,6,7,8-tetrahydroindolo[2,1-a][2,5]benzodiazocine-11-carboxylate To a stirred solution of methyl 3-cyclohexyl-1-(2,2-dimethoxyethyl)-2-[2-({[2-(dimethylamino)ethyl]amino}methyl)phenyl]-1H-indole-6-carboxylate (0.16 M, 1 eq, from Step 3) in THF was added an equal volume of aqueous 1N HCl. The reaction was heated at 60° C. for 2.5 h and after cooling to RT was quenched by addition of NaOH (2N) and extracted into EtOAc (×3). The combined organic extracts were washed with brine before being dried over Na$_2$SO$_4$, filtered and concentrated in vacuo. The residue was re-dissolved in MeOH and acidified to pH 4 with glacial acetic acid. After stirring for 45 min, NaBH$_4$ (8 eq) was added portionwise until cyclisation was complete as evidenced by LC-MS analysis. The reaction was quenched by addition of sat. aq. NaHCO$_3$ and extracted into EtOAc (×3). The combined organic extracts were washed with brine before being dried (Na$_2$SO$_4$), filtered and concentrated in vacuo. The title compound was obtained as a pale yellow oil and taken on without further purification (quant.); MS (ES$^+$) m/z 460 (M+H)$^+$.

Step 5: 14-cyclohexyl-6-[2-(dimethylamino)ethyl]-5,6,7,8-tetrahydroindolo[2,1-a][2,5]benzo diazocine-11-carboxylic acid A solution of methyl 14-cyclohexyl-6-[2-(dimethylamino)ethyl]-5,6,7,8-tetrahydroindolo[2,1-a][2,5]benzodiazocine-11-carboxylate (0.16 M, 1 eq, from Step 4) in MeOH and 1N NaOH (4 eq) was heated to 80° C. for 6 h. After cooling to RT, the MeOH was removed under reduced pressure and the resulting aqueous solution acidified with aqueous 3N HCl until pH 1-2 resulting in formation of a pale yellow precipitate. This was filtered off and dried on the filter overnight to afford the crude hydrochloride salt of the product as a yellow solid. Purification was by RP-HPLC (stationary phase: column Waters XTERRA prep. MS C18, 5 μm, 30×100 mm. Mobile phase: MeCN/H$_2$O buffered with 0.1% TFA). Fractions containing the pure compound were combined and freeze dried (2×) in the presence of 3N aqueous HCl to afford the bis-HCl salt of the title compound as a white powder (65% over steps 3, 4 and 5).
$^1$H NMR (400 MHz, d$_6$-DMSO+TFA, 300 K) δ 1.12-1.15 (m, 1H), 1.31-1.36 (m, 2H), 1.53-1.56 (m, 1H), 1.67-1.72 (m, 2H), 1.82-1.84 (m, 1H), 1.90-1.99 (m, 3H), 2.62-2.69 (m, 1H), 2.87 (s, 6H), 3.45-3.50 (m, 1H), 3.62-3.82 (m, 7H), 4.52 (d, J 13.6, 1H), 4.84 (dd, J 16.6, 4.6, 1H), 7.47-7.49 (m, 1H), 7.63-7.68 (m, 2H), 7.74 (d, J 8.4, 1H), 7.93-7.95 (m, 2H), 8.2 (s, 1H); MS (ES$^+$) m/z 446 (M+H)$^+$.

EXAMPLE 21

14-cyclohexyl-3-methoxy-6-methyl-5,6,7,8-tetrahydroindolo[2,1-a][2,5]benzodiazocine-11-carboxylic acid Step 1: methyl 2-[4-chloro-2(ethoxycarbonyl)phenyl-3-cyclohexyl-1H-indole-6-carboxylate To a solution of methyl 2-bromo-3-cyclohexyl-1H-indole-6-carboxylate in dioxane (prepared as described in published International patent application WO2004/087714), (0.07 M) was added bis(triphenylphosphine)palladium(II) dichloride (0.2 eq) at RT under a nitrogen atmosphere. Then 4-chloro-2-ethoxycarbonyl-phenyl-boronic acid (2 eq) and Na$_2$CO$_3$ (2 M solution, 2 eq.) were added and the reaction flask immersed in a preheated oil bath at 100° C. for 2 h. The reaction mixture was allowed to cool and filtered. The filtrate was diluted with DCM and the organic phase washed with H$_2$O, brine and dried over Na$_2$SO$_4$ before being filtered and concentrated in vacuo. The crude material was purified by flash chromatography (1:9 EtOAc/PE) to afford the title compound as a solid (62%); MS (ES$^+$) m/z 440 (M+H)$^+$.

Step 2: methyl 2-[4-chloro-2(hydroxymethyl)phenyl-3-cyclohexyl-1H-indole-6-carboxylate To a solution of methyl 2-[4-chloro-2(ethoxycarbonyl)phenyl-3-cyclohexyl-1H-indole-6-carboxylate (from Step 1) in THF (0.36 M), BH$_3$.THF (1 M solution in THF, 2 eq) was added and the solution allowed to stir at reflux for 1.5 h. The solution was diluted with EtOAc. The organic phase was washed with saturated aqueous NaHCO$_3$ and brine. The organic phase was dried over Na$_2$SO$_4$, filtered and the solvent evaporated in vacuo. The crude material was purified by flash chromatography (1:9 to 2:8 EtOAc/PE gradient) to afford the title compound as a solid (68%); MS (ES$^+$) m/z 398 (M+H)$^+$.

Step 3: methyl 2-[4-chloro-2-(hydroxymethyl)phenyl-3-cyclohexyl-1-(2-methoxy-2-oxoethyl)-1H-indole-6-carboxylate Methyl bromoacetate (2 eq) was added to a mixture of methyl 2-[4-chloro-2-(hydroxymethyl)phenyl-3-cyclohexyl-1H-indole-6-carboxylate (from Step 2) and potassium carbonate (3 eq) in dry DMSO (0.2 M). The mixture was stirred at 60° C. overnight. At this time the reaction was allowed to cool to RT, diluted with EtOAc. The organic phase was washed with H$_2$O (twice), 1 N HCl and then brine. The organic phase was dried over Na$_2$SO$_4$, filtered and the solvent evaporated in vacuo. The residue was purified by flash chromatography (SiO$_2$; 15:85 EtOAc/PE) to afford the title compound (46%); MS (ES$^+$) m/z 470 (M+H)$^+$.

Step 4: methyl 2-(4-chloro-2-formylphenyl)-3-cyclohexyl-1-(2-methoxy-2-oxoethyl)-1H-indole-6-carboxylate A solution of methyl 2-[4-chloro-2(hydroxymethyl)phenyl-3-cyclohexyl-1-(2-methoxy-2-oxoethyl)-1H-indole-6-carboxylate (from Step 3) in dry DCM (0.03M) was added dropwise to a solution of DMP (1.2 eq) in dry DCM (0.07 M) at 0° C. The mixture was allowed to reach RT in 2 h and then diluted with DCM. The organic phase was washed with an aqueous solution Na$_2$S$_2$O$_3$.5H$_2$O: NaHCO$_3$ (1:1) (5×) then brine. The organic phase was dried (Na$_2$SO$_4$), filtered and the solvent evaporated in vacuo to give the title compound (quant); MS (ES$^+$) m/z 468 (M+H)$^+$.

Step 5: methyl 2[4-chloro-2-({[2-(dimethylamino)ethyl]amino}methyl)phenyl)-3-cyclohexyl-1-(2-methoxy-2-oxoethyl)-1H-indole-6-carboxylate To a solution of methyl 2-(4-chloro-2-formylphenyl)-3-cyclohexyl-1-(2-methoxy-2-oxoethyl)-1H-indole-6-carboxylate (from Step 4) in THF (0.04 M), 2-dimethylaminoethylamine (1.5 eq) was added and the pH adjusted to pH 5 with acetic acid. The solution was stirred at RT for 1.5 h before being concentrated in vacuo. The residue was taken up in MeOH to give a 0.04 M solution. NaBH$_3$CN (1 eq) was added and the mixture stirred at RT overnight. The reaction was quenched with saturated aqueous NaHCO$_3$ and extracted (2×) with EtOAc. The combined organics were washed with water and brine before being dried (Na$_2$SO$_4$), filtered and concentrated in vacuo to give the title compound. The crude was used in the next step without further purification (quant); MS (ES$^+$) m/z 540 (M+H)$^+$.

Step 6: methyl 3-chloro-14-cyclohexyl-6-[2-(dimethylamino)ethyl]-7-oxo-5,6,7,8-tetrahydroindolo[2,1-a][2,5]benzodiazocine-11-carboxylate To a solution of methyl 2-[4-chloro-2-({[2-(dimethylamino)ethyl]amino}methyl)phenyl-3-cyclohexyl-1-(2-methoxy-2-oxoethyl)-1H-indole-6-carboxylate (from Step 5) in dry MeOH (0.05 M), 10% in weight of MeONa was added and the mixture stirred at RT overnight. The volume of the solution was reduced in vacuo before being diluted with EtOAc. The organic phase was washed with HCl 1 N, brine. The organic phase was dried over Na$_2$SO$_4$, filtered and the solvent evaporated in vacuo to afford the title compound. The crude was then used in the next step without any further purification (quant); MS (ES$^+$) m/z 508 (M+H)$^+$.

Step 7: methyl 3-chloro-14-cyclohexyl-6-[2-(dimethylamino)ethyl]-5,6,7,8-tetrahydroindolo[2,1-a][2,5]benzodiazocine-11-carboxylate To a solution of methyl 3-chloro-14-cyclohexyl-6-[2-(dimethylamino)ethyl]-7-oxo-5,6,7,8-tetrahydroindolo[2,1-a][2,5]benzodiazocine-11-carboxylate (from Step 6) in THF (0.02 M), BH$_3$.THF (1 M solution in THF, 5 eq) was added and the solution allowed to stir at RT for 2 h. MeOH (0.02 M) and a 1.25 M solution HCl in MeOH (0.24 M) were added carefully and stirred overnight at RT before being heated at 60° C. for 3 h. The volatiles were then removed in vacuo. The volume of the solution was reduced in vacuo before diluting with EtOAc. The organic phase was washed with saturated aqueous NaHCO$_3$ and brine. The organic phase was dried over Na$_2$SO$_4$, filtered and the solvent evaporated in vacuo to afford the title compound. The crude was then used in the next step without any further purification (quant); MS (ES$^+$) 494 (M+H)$^+$.

Step 8: 3-chloro-14-cyclohexyl-6-[2-(dimethylamino)ethyl]-5,6,7,8-tetrahydroindolo[2,1-a][2,5]benzodiazocine-11-carboxylic acid Methyl 3-chloro-14-cyclohexyl-6-[2-(dimethylamino)ethyl]-5,6,7,8-tetrahydroindolo[2,1-a][2,5]benzodiazocine-11-carboxylate (from Step 7) was dissolved in a solution THF: MeOH (1:1) (0.02 M) and to that solution 7 eq of an aqueous solution of NaOH (1N) were added. The solution was stirred at 60° C. for 3 h. The solvent was evaporated in vacuo. The crude was then purified by automated RP-MS-HPLC (stationary phase: column Waters XTERRA prep. C18, 5 um, 19×100 mm. Mobile phase: MeCN/H$_2$O buffered with 0.1% TFA). Fractions containing the pure compound were combined and freeze dried to afford the title compound as a white powder (21%).

$^1$H NMR (400 MHz, DMSO-d$_6$+TFA, 330 K) δ 1.14-1.34 (m, 3H), 1.52-1.55 (m, 1H), 1.67-1.73 (m, 2H), 1.82-1.84 (m, 1H), 1.90-1.97 (m, 3H), 2.54-2.65 (m, 1H), 2.87 (s, 6H), 3.34-3.38 (m, 1H), 3.55-3.76 (m, 7H), 4.32 (d, J 13.6, 1H), 4.80 (dd, J 16.6, 3.8, 1H), 7.49 (d, J 8.0, 1H), 7.71-7.75 (m, 2H), 7.93 (d, J 8.4, 1H), 8.04 (s, 1H), 8.17 (s, 1H); MS (ES$^+$) m/z 480 (M+H)$^+$.

NO EXAMPLE 22

EXAMPLE 23

2-{[(7S)-11-carboxy-14-cyclohexyl-7,8-dihydro-6H-indolo[1,2-e][1,5]benzoxazocin-7-yl]oxy}-N,N-dimethylethanaminium trifluoroacetate Step 1: 2-{[(7S)-11-carboxy-14-cyclohexyl-7,8-dihydro-6H-indolo[1,2-e][1,5]benzoxazocin-7-yl] oxy}-N,N-dimethylethanaminium trifluoroacetate To a suspension of methyl (7S)-14-cyclohexyl-7-hydroxy-7,8-dihydro-6H-indolo[1,2-e][1,5]benzoxazocine-11-carboxylate (obtained as described in Example 9, Steps 1-3) in toluene (0.05 M), were added 10 eq of 30% w/w aq. NaOH followed by 0.25 eq of tetrabutylammonium bromide. After stirring for 30 min, 2 eq of 2-chloro-N,N-dimethylethanaminium chloride were added and the reaction mixture was stirred at 60° C. for 16 h. 1 further eq of 2-chloro-N,N-dimethylethanaminium chloride was added and the reaction mixture was stirred at 80° C. for 4 further h. The reaction mixture was concentration in vacuo, redissolved with DMSO and purified by RP-HPLC (stationary phase: column Waters XTERRA prep. C18, 5 um, 19×100 mm. Mobile phase: MeCN/H$_2$O buffered with 0.1% TFA). Fractions containing the pure compound were combined and freeze dried to afford the title compound as a white powder (47%).

$^1$H NMR (400 MHz, DMSO-d$_6$, 300 K, two diastereomers 1:1) δ 1.08-1.23 (m, 1H), 1.24-1.44 (m, 2H), 1.49-1.61 (m, 1H), 1.64-1.77 (m, 2H), 1.80-1.88 (m, 1H), 1.89-2.07 (m, 3H), 2.56 (s, 1.5 H), 2.63-2.73 (m, 1H), 2.78 (s, 1.5H), 3.07 (m, 1H), 3.27 (m, 1H), 3.68 (dd, J 10.7, 14.5, 0.5H), 3.75-3.97 (m, 3H), 3.98-4.14 (m, 1.5H), 4.24 (dd, J 4.2, 13.2, 0.5H), 4.77 (dd, J 2.7, 14.6, 0.5H), 4.93 (dd, J 3.1, 15.6, 0.5H), 7.16-7.34 (m, 3H), 7.49 (d, J 6.8, 0.5H), 7.50 (d, J 6.8, 0.5H), 7.62 (d, J 8.1, 0.5H), 7.69 (d, J 8.3, 0.5H), 7.82 (d, J 8.6, 0.5H), 7.89 (d, J 8.3, 0.5H), 8.20 (s, 0.5H), 8.21 (s, 0.5H); MS (ES$^+$) m/z 463 (M+H)$^+$; [α]$_D^{20}$=-41.2 (c=0.31, CH$_3$OH).

EXAMPLE 24

2-{[(7R)-11-carboxy-14-cyclohexyl-7,8-dihydro-6H-indolo[1,2-e][1,5]benzoxazocin-7-yl]oxy}-N,N-dimethylethanaminium trifluoroacetate The title compound was obtained in an analogous manner as reported for the enantiomer in the previous example employing (R)-glycidyl 3-nitrobenzenesulfonate instead of the (S)-glycidyl 3-nitrobenzenesulfonate in Example 9, Step 2, giving methyl 3-cyclohexyl-2-{2-[(2R)-oxiran-2-ylmethoxy]phenyl}-1H-indole-6-carboxylate: [α]$_D^{20}$=-19.8 (c=0.5, CHCl$_3$); and after cyclization methyl (7R)-14-cyclohexyl-7-hydroxy-7,8-dihydro-6H-indolo[1,2-e][1,5]benzox- azocine-11-carboxylate: [α]$_D^{20}$=+29.9 (c=0.54, CHCl$_3$). The latter was converted to the title compound as described in example 23: [α]$_D^{20}$=+41.9 (c=0.32, CH$_3$OH); $^1$H NMR and MS as for 2-{[(7S)-11-carboxy-14-cyclohexyl-7,8-dihydro-6H-indolo[1,2-e][1,5]benzoxazocin-7-yl]oxy}-N,N-dimethylethanaminium trifluoroacetate.

EXAMPLE 25

1-(2-{[(7S)-11-carboxy-14-cyclohexyl-7,8-dihydro-6H-indolo[1,2-e][1,5]benzoxazocin-7-yl]oxy}ethyl) pyrrolidinium trifluoroacetate To a suspension of methyl (7S)-14-cyclohexyl-7-hydroxy-7,8-dihydro-6H-indolo[1,2-e][1,5]benzoxazocine-11-carboxylate (prepared as described in Example 9, Steps 1-3) in toluene (0.05 M), were added 15 eq of 40% w/w aq. NaOH followed by 0.25 eq of tetrabutylammonium bromide. After stirring for 30 min, 3 eq of 1-(2-chloroethyl)pyrrolidinium chloride were added and the reaction mixture was stirred at 70° C. for 18 h. The reaction mixture was concentration in vacuo, redissolved with DMSO and purified by RP-HPLC (stationary phase: column Waters XTERRA prep. C18, 5 um, 19×100 mm. Mobile phase: MeCN/H$_2$O buffered with 0.1% TFA). Fractions containing the pure compound were combined and freeze dried to afford the title compound as a white powder (65%).

$^1$H NMR (400 MHz, DMSO-d$_6$, 300 K, two diastereomers 1:1) δ 1.10-1.23 (m, 1H), 1.25-1.42 (m, 2H), 1.49-1.59 (m, 1H), 1.64-2.07 (m, 10H), 2.62-2.75 (m, 1.5H), 2.90 (m, 0.5H), 3.04-3.48 (m, 2.5H), 3.61 (m, 0.5H), 3.71 (dd, J 10.5, 14.5, 0.5H), 3.76-3.97 (m, 3.5H), 3.98-4.18 (m, 1.5H), 4.29 (dd, J 4.4, 13.2, 0.5H), 4.78 (dd, J 3.0, 14.4, 0.5H), 4.95 (dd, J 3.7, 15.6, 0.5H), 7.19-7.32 (m, 3H), 7.46-7.54 (m, 1H), 7.62 (dd, J 1.2, 8.4, 0.5H), 7.70 (dd, J 1.1, 8.3, 0.5H), 7.83 (d, J 8.6, 0.5H), 7.89 (d, J 8.3, 0.5H), 8.20 (s, 0.5H), 8.22 (s, 0.5H), 9.39 (brs, 0.5H, NH), 9.49 (brs, 0.5H, NH), 12.60 (brs, 1H, OH); MS (ES$^+$) m/z 489 (M+H)$^+$.

EXAMPLE 26

(2Z)-(11-carboxy-14-cyclohexyl-6H-indolo[1,2-e][1,5]benzoxazocin-7(8H)-ylidene)-N,N-dimethylethanaminium trifluoroacetate and (2E)-(11-carboxy-14-cyclohexyl-6H-indolo[1,2-e][1,5]benzoxazocin-7(8H)-ylidene)-N,N-dimethylethanaminium trifluoroacetate Step 1: (2Z)-2-[14-cyclohexyl-11-(methoxycarbonyl)-6H-indolo[1,2-e][1,5]benzoxazocin-7(8H)-ylidene]-N,N-dimethylethanaminium trifluoroacetate and (2E)-2-[14-cyclohexyl-11-(methoxycarbonyl)-6H-indolo[1,2-e][1,5]benzoxazocin-7(8H)-ylidene]-N,N-dimethylethanaminium trifluoroacetate To a suspension of 1.5 eq of [2-(dimethylamino)ethyl](triphenyl)phosphonium bromide in THF (0.12 M) cooled at −78° C., was added n-BuLi (1.6 eq, 1.6 M in hexanes). After stirring for 30 min at 0° C., the reaction mixture was cooled to −20° C. and methyl 14-cyclohexyl-7-oxo-7,8-dihydro-6H-indolo[1,2-e][1,5]benzoxazocine-11-carboxylate (obtained as described in Example 9, Steps 1-4) in THF (0.18 M) was added. The reaction mixture was warmed to RT within 3 h followed by addition of ice and CH$_2$Cl$_2$. The organic phase was dried (Na$_2$SO$_4$) before being filtered, concentrated in vacuo, redissolved with DMSO and purified by RP-HPLC (stationary phase: column Waters XTERRA prep. C18, 5 um, 19×100 mm. Mobile phase: MeCN/H$_2$O buffered with 0.1% TFA). Fractions containing the pure compound were combined and freeze dried to afford the title compound as a white powder (28%); MS (ES$^+$) m/z 459 (M+H)$^+$.

Step 2: (2Z)-(11-carboxy-14-cyclohexyl-6H-indolo[1,2-e][1,5]benzoxazocin-7(8H)-ylidene)-N,N-dimethylethanaminium trifluoroacetate and (2E)-(11-carboxy-14-cyclohexyl-6H-indolo[1,2-e][1,5]benzoxazocin-7(8H)-ylidene)-N,N-dimethylethanaminium trifluoroacetate To a solution of the foregoing product (from Step 1) in THF/MeOH (0.01 M, 1:1, v/v) was added KOH (5 eq, 1N) and the mixture was stirred at 60° C. After 16 h, KOH (5 eq, 1N) was added and the mixture was stirred at 60° C. for further 8 h. The reaction mixture was concentrated in vacuo, redissolved with DMSO and purified by RP-HPLC (stationary phase: column Waters XTERRA prep. C18, 5 um, 19×100 mm. Mobile phase: MeCN/$H_2O$ buffered with 0.1% TFA). Fractions containing the pure compound were combined and freeze dried to afford the title compound as a white powder (73%).

$^1$H NMR (600 MHz, DMSO-$d_6$, 300K, Z:E 7:3) δ 1.10-1.21 (m, 1H), 1.25-1.40 (m, 2H), 1.48-1.59 (m, 1H), 1.64-1.75 (m, 2H), 1.80-1.86 (m, 1H), 1.88-1.99 (m, 3H), 2.59-2.74 (m, 1H), 2.73 (s, 2.1H), 2.78 (s, 0.9H), 3.78 (dd, J 7.5, 13.9, 0.7H), 3.90 (dd, J 7.1, 13.6, 0.7H), 4.16 (m, 0.6H), 4.24 (d, J 13.2, 0.3H), 4.33 (d, J 15.2, 1H), 4.42 (d, J 13.4, 0.3H), 4.59 (d, J 14.5, 0.7H), 5.06 (d, J 14.7, 0.7H), 5.13 (d, J 15.4, 0.7H), 5.57 (d, J 16.5, 0.3H), 5.71 (t, J 7.2, 0.3H), 6.09 (t, J 7.4, 0.7H), 7.14 (d, J 7.7, 0.3H), 7.19 (t, J 7.5, 0.3H), 7.25-7.40 (m, 2.4H), 7.46 (t, J 8.4, 0.3H), 7.57 (t, J 7.5, 0.7H), 7.66 (dd, J 1.1, 8.4, 0.7H), 7.68 (d, J 8.6, 0.3H), 7.86 (d, J 8.3, 0.7H), 7.88 (d, J 7.7, 0.3H), 8.20 (s, 0.3H), 8.22 (s, 0.7H); MS (ES$^+$) m/z 445 (M+H)$^+$.

NO EXAMPLE 27

EXAMPLE 28

N-(11-carboxy-14-cyclohexyl-3-fluoro-7,8-dihydro-6H-indolo[1,2-e][1,5]benzoxazocin-7-yl)-N,N',N'-trimethylethane-1,2-diaminium bis(trifluoroacetate)

Step 1: methyl 3-cyclohexyl-2-(4-fluoro-2-hydroxyphenyl)-1H-indole-6-carboxylate To a solution of methyl 2-bromo-3-cyclohexyl-1H-indole-6-carboxylate (prepared as described in WO2004087714 from commercially available methyl indole-6-carboxylate) in a mixture of DME and EtOH (5:2, v/v, 0.2 M) were added 2.6 eq. of $Na_2CO_3$ (2 M aqueous solution), 1.3 eq. of 4-fluoro-2-hydroxy-phenylboronic acid and 0.1 eq. of tetrakis(triphenylphosphine)palladium(0). The mixture was degassed thoroughly with a stream of argon and then heated to 100° C. overnight. The reaction mixture was allowed to cool to RT, diluted with EtOAc and washed with 1N hydrochloric acid and with brine, dried over $Na_2SO_4$ and concentrated in vacuo. The crude material was purified by flash chromatography (1:5 EtOAc/PE) to afford the title compound as a beige solid (61%); MS (ES$^+$) m/z 368 (M+H)$^+$.

Step 2: methyl 3-cyclohexyl-2-{4-fluoro-2-[(2S)-oxiran-2-ylmethoxy]phenyl}-1H-indole-6-carboxylate To a solution of the foregoing product (from Step 1) in DMF (0.05 M) was added cesium fluoride (3 eq.) and (S)-glycidyl 3-nitrobenzenesulfonate (1.1 eq.). The resulting mixture was stirred at RT overnight then diluted with EtOAc and washed with water and brine. Drying over $Na_2SO_4$, filtration and concentration i. vac. gave the crude product, which was purified by flash chromatography (1:5 EtOAc/PE) to afford the title compound as colourless foam (70%); MS (ES$^+$) m/z 424 (M+H)$^+$.

Step 3: methyl (7S)-14-cyclohexyl-3-fluoro-7-hydroxy-7,8-dihydro-6H-indolo[1,2-e][1,5]benzoxazocine-11-carboxylate A solution of the foregoing product (from Step 2) in dry DMF (0.05 M) was cooled to 0° C. and a 1M solution of sodium bis(trimethylsilyl)amide in THF (1.1 eq.) was added dropwise. The reaction was allowed to reach RT and stirred for 3 h. The reaction mixture was diluted with EtOAc and washed with hydrochloric acid (1 N), water and brine. Drying over $Na_2SO_4$, filtration and concentration i. vac. gave the crude product, which was purified by flash chromatography (1:4 EtOAc/PE) to afford the title compound as colourless foam (50%, mixture of diastereomers, 2:1); MS (ES$^+$) m/z 424 (M+H)$^+$.

Step 4: methyl 14-cyclohexyl-3-fluoro-7-oxo-7,8-dihydro-6H-indolo[1,2-e][1,5]benzoxazocine-11-carboxylate To a solution of the foregoing alcohol (from Step 3) in DCM (0.06 M) was added DMP (1.5 eq.), and the mixture was stirred overnight at RT. The reaction mixture was diluted with EtOAc and washed with a 1:1 (v/v) mixture of sodium thiosulfate and sodium hydrogen carbonate (both saturated aqueous solutions), then with brine. Drying over $Na_2SO_4$, filtration and concentration i. vac. gave the crude product, which was used without further purification (92%); MS (ES$^+$) m/z 422 (M+H)$^+$.

Step 5: methyl 14-cyclohexyl-7-{[2-(dimethylamino)ethyl]amino}-3-fluoro-7,8-dihydro-6H-indolo[1,2-e][1,5]benzoxazocine-11-carboxylate To a solution of foregoing crude ketone (from Step 4) in DCE (0.06 M) was added N,N-dimethylethane-1,2-diamine (1.0 eq) and HOAc (1.5 eq.), followed by solid sodium triacetoxyborohydride (1.5 eq). NaOH (20 eq., 1 N) was added after 16 h, and after stirring for 5 min the mixture was taken into EtOAc and washed with water and brine. Drying over $Na_2SO_4$ and concentration i. vac. gave the crude product, which was used without further purification; MS (ES$^+$) m/z 494 (M+H)$^+$.

Step 6: methyl 14-cyclohexyl-7-[[2-(dimethylamino)ethyl](methyl)amino]-3-fluoro-7,8-dihydro-6H-indolo[1,2-e][1,5]benzoxazocine-11-carboxylate To a solution of crude methyl 14-cyclohexyl-7-{[2-(dimethylamino)ethyl]amino}-3-fluoro-7,8-dihydro-6H-indolo[1,2-e][1,5]benzoxazocine-11-carboxylate (from Step 5) in DCM (0.05 M) was added formaldehyde (3.0 eq) and HOAc (5.5 eq), followed by sodium cyanoborohydride (3 eq). NaOH (20 eq, 1 N) was added after 2 h, and after stirring for 5 min the mixture was taken into EtOAc and washed with water and brine. Drying over $Na_2SO_4$ and concentration i. vac. gave the crude product which was used without further purification; MS (ES$^+$) m/z 508 (M+H)$^+$.

Step 7: N-(11-carboxy-14-cyclohexyl-7,8-dihydro-6H-indolo[1,2-e][1,5]benzoxazocin-7-yl)-N,N',N'-trimethylethane-1,2-diaminium bis(trifluoroacetate)

To a solution of the foregoing product (from Step 6) in dioxane (0.08 M) were added 3 eq. of 1M aqueous KOH solution and the mixture was stirred at 60° C. for 4 h. The reaction mixture was brought to pH 2 by the dropwise addition of hydrochloric acid (1 N), then diluted with MeCN and purified by RP-HPLC (stationary phase: column Waters SYMMETRY prep. C18, 7 um, 19×150 mm. Mobile phase: MeCN/$H_2O$ buffered with 0.1% TFA). The product fractions were lyophilised to afford the title compound as its bis-trifluoroacetate salt (white powder, 40% over three steps).

$^1$H NMR (400 MHz, DMSO, 300 K, 2 diastereomers 96:4, only the data for the major atropoisomer are reported) δ1.09-1.21 (m, 1H), 1.23-1.40 (m, 2H), 1.50 (d, J 11.4, 1H), 1.68-1.75 (m, 2H), 1.85-2.08 (m, 4H), 2.37 (s, 3H), 2.60-2.66 (m, 1H), 2.82 (s, 6H), 2.89-2.99 (m, 1H), 3.06-3.18 (m, 3H), 3.25-3.29 (m, 1H), 3.85 (dd, J 10.1, 14.6, 1H), 4.11 (dd, J 9.0, 12.1, 1H), 4.26 (dd, J 4.3, 12.1, 1H), 4.66 (d, J 14.6, 1H), 7.14-7.22 (m, 2H), 7.36 (t, J 6.9, 1H), 7.69 (dd, J 0.8, 8.3, 1H), 7.87 (d, J 8.3, 1H), 8.15 (s, 1H), 8.94 (brs, 1H), 12.60 (brs, 1H); MS (ES$^+$) m/z 494 (M+H)$^+$.

EXAMPLE 29

(7R)-14-cyclohexyl-7-[[2-(dimethylamino)ethyl](methyl)amino]-3-fluoro-7,8-dihydro-6H-indolo[1,2-e][1,5]benzoxazocine-11-carboxylic acid The racemic mixture (obtained as described in Example 28) was subjected to chiral SFC separation (Pcol=100 bar, Tcol=35° C.; stationary phase: CHIRALPAK AD-H, 10×250 mm; mobile phase modifier: MeOH+0.2% diethylamine) to obtain the title compound as the first eluting peak; single enantiomer in >99% ee. NMR and MS as reported for the racemic mixture in example 1. The second peak was (7S)-14-cyclohexyl-7-[[2-(dimethylamino)ethyl](methyl)amino]-3-fluoro-7,8-dihydro-6H-indolo[1,2-e][1,5]benzoxazocine-11-carboxylic acid (97% ee).

EXAMPLE 30

1-(2-{[(7S)-11-carboxy-14-cyclohexyl-3-fluoro-7,8-dihydro-6H-indolo[1,2-e][1,5]benzoxazocin-7-yl]oxy}ethyl)pyrrolidinium trifluoroacetate To a suspension of methyl (7S)-14-cyclohexyl-3-fluoro-7-hydroxy-7,8-dihydro-6H-indolo[1,2-e][1,5]benzoxazocine-11-carboxylate (prepared as described in Example 28, Steps 1-3) in toluene (0.05 M), were added 15 eq. of 40% w/w aq. NaOH followed by 0.25 eq. of tetrabutylammonium bromide. After stirring for 30 min, 3 eq. of 1-(2-chloroethyl)pyrrolidinium chloride were added and the reaction mixture was stirred at 70° C. for 18 h. The reaction mixture was concentrated in vacuo, redissolved with DMSO and purified by RP-HPLC (stationary phase: column Waters XTERRA prep. C18, 5 um, 19×100 mm. Mobile phase: MeCN/H$_2$O buffered with 0.1% TFA). The product fractions were lyophilised to afford the title compound as a white powder (30%).

$^1$H NMR (400 MHz, DMSO-d$_6$, 300 K, two diastereomers 1:1) δ 1.16-1.22 (m, 1H), 1.29-1.44 (m, 2H), 1.53-1.56 (m, 1H), 1.68-2.03 (m, 10H), 2.63-2.73 (m, 1.5H), 2.85-2.94 (m, 0.5H), 3.07-3.39 (m, 3.5H), 3.61-3.69 (m, 0.5H), 3.72 (dd, J 10.5, 14.5, 0.5H), 3.79-4.01 (m, 5.5H), 4.10-4.21 (m, 1H), 4.78 (dd, J 3.0, 14.4, 0.5H), 4.95 (dd, J 3.7, 15.6, 0.5H), 7.05-7.12 (m, 2H), 7.28-7.32 (m, 1H), 7.62 (dd, J 1.2, 8.4, 0.5H), 7.70 (dd, J 1.1, 8.3, 0.5H), 7.83 (d, J 8.6, 0.5H), 7.89 (d, J 8.3, 0.5H), 8.21 (s, 1H), 9.45 (brs, 0.5H, NH), 9.55 (brs, 0.5H, NH), 12.70 (brs, 1H, OH); MS (ES$^+$) m/z 507 (M+H)$^+$.

EXAMPLE 31

(11-carboxy-14-cyclohexyl-7,8-dihydro-6H-indolo[1,2-e][1,5]benzoxazocin-7-yl)-N,N-dimethylmethanaminium trifluoroacetate Step 1: methyl 14-cyclohexyl-7-methylene-7,8-dihydro-6H-indolo[1,2-e][1,5]benzoxazocine-11-carboxylate To a solution of methyl 3-cyclohexyl-2-(2-hydroxyphenyl)-1H-indole-6-carboxylate (prepared as described in example 9, step 1) in dry DMF (0.06 M) was added NaH (2.5 eq., 60% suspension in mineral oil). After 30 min, 3-chloro-2-(chloromethyl)prop-1-ene (1.2 eq.) was added dropwise via syringe and the solution stirred at RT for 60 min. The reaction mixture was diluted with EtOAc and washed with 1N aqueous HCl and with brine, dried (Na$_2$SO$_4$) and evaporated. The crude residue was purified by flash chromatography (10:1 PE/EtOAc), affording the pure methyl 14-cyclohexyl-7-methylene-7,8-dihydro-6H-indolo[1,2-e][1,5]benzoxazocine-11-carboxylate (70%) as light yellow foam; MS (ES$^+$) m/z 402 (M+H)$^+$.

Step 2: methyl 14-cyclohexyl-7-(hydroxymethyl)-7,8-dihydro-6H-indolo[1,2-e][1,5]benzoxazocine-11-carboxylate Borane-dimethylsulfide complex (2M solution in THF, 1.6 eq) was added to a solution of methyl 14-cyclohexyl-7-methylene-7,8-dihydro-6H-indolo[1,2-e][1,5]benzoxazocine-11-carboxylate (from Step 1) in dry THF (0.12 M) at 0° C. The solution was stirred for 16 h at RT. The reaction mixture was cooled to 0° C. and treated dropwise with 3N NaOH (3 eq.) followed by 35% (v/v) H$_2$O$_2$ solution and the resulting mixture was stirred for 2 h at RT. The mixture was diluted with EtOAc, washed with aqueous saturated NaHCO$_3$-solution and with brine, dried (Na$_2$SO$_4$). Evaporation afforded a crude residue which was purified by flash chromatography (4:1 PE/EtOAc). Methyl 14-cyclohexyl-7-(hydroxymethyl)-7,8-dihydro-6H-indolo[1,2-e][1,5]benzoxazocine-11-carboxylate (50%) was obtained as colorless solid; MS (ES$^+$) m/z 402 (M+H)$^+$.

Step 3: methyl 14-cyclohexyl-7-formyl-7,8-dihydro-6H-indolo[1,2-e][1,5]benzoxazocine-11-carboxylate A solution of methyl 14-cyclohexyl-7-(hydroxymethyl)-7,8-dihydro-6H-indolo[1,2-e][1,5]benzoxazocine-11-carboxylate (from step 2) in dry DCM (0.1 M) was treated with DMP (1.2 eq.) and the resulting solution was stirred for 2 h at RT. The reaction mixture was diluted with EtOAc and washed with a 1:1 (v/v) mixture of sodium thiosulfate and NaHCO$_3$ (both aqueous saturated solutions), then with brine. Drying over Na$_2$SO$_4$, filtration and concentration i. vac. gave the crude methyl 14-cyclohexyl-7-formyl-7,8-dihydro-6H-indolo[1,2-e][1,5]benzoxazocine-11-carboxylate, which without further purification.

Step 4: 14-cyclohexyl-7-[(dimethylamino)methyl]-7,8-dihydro-6H-indolo[1,2-e][1,5]benzoxazocine-11-carboxylic acid The foregoing aldehyde (from Step 3) was reductively aminated using dimethylamine and sodium triacetoxy sodiumborohydride and the ester from the resulting product hydrolyzed as described in Example 9, Step 6. Purification of the crude product by RP-HPLC (stationary phase: column Waters SYMMETRY prep. C18, 7 um, 19×150 mm. Mobile phase: MeCN/H$_2$O buffered with 0.1% TFA) gave the product fractions after lyophilization as its trifluoroacetate salt (white powder, 10%).

$^1$H NMR (400 MHz, DMSO-d$_6$, 300 K, 2 diastereomers 7:1, only data for the major isomer are reported) δ1.21-1.45

(m, 3H), 1.50-1.61 (m, 1H), 1.62-1.78 (m, 2H), 1.79-1.89 (m, 1H), 1.90-2.08 (m, 3H), 2.64-2.73 (m, 1H), 2.76-2.83 (m, 1H), 2.89 (s, 6H), 3.18-3.35 (m, 2H, partially obscured by water), 3.66 (dd, J 11.3, 15.0, 1H), 3.91 (dd, J 5.2, 12.7, 1H), 4.03 (dd, J 2.2, 12.7, 1H), 4.70 (dd, J 3.5, 15.0, 1H), 7.15-7.23 (m, 2H), 7.27 (dd, J 1.5, 7.5, 1H), 7.50 (dt, J 1.5, 7.8, 1H), 7.70 (dd, J 1.1, 8.4, 1H), 7.90 (d, J 8.4, 1H), 8.25 (s, 1H), 9.61 (bs, 1H), 12.62 (bs, 1H); (ES$^+$) m/z 433 (M+H)$^+$.

EXAMPLE 32

Preparation of 13-cyclohexyl-5-[2-(dimethylamino)ethyl]-4,5,6,7-tetrahydrothieno[2',3':6,7][1,4]diazocino[1,8-a]indole-10-carboxylic acid Step 1: Methyl 1-(2-tert-butoxy-2-oxoethyl)-3-cyclohexyl-2-(2-formyl-3-thienyl)-1H-indole-6-carboxylate Methyl 2-bromo-1-(2-tert-butoxy-2-oxoethyl)-3-cyclohexyl-1H-indole-6-carboxylate (prepared as described in Example 1, Step 1) and (2-formyl-3-thienyl) boronic acid (1.5 eq) were dissolved in dioxane (0.07 M) and 2M aqueous Na$_2$CO$_3$ (6 eq) was added. The solution was degassed by bubbling argon, Pd(PPh$_3$)$_2$Cl$_2$ (0.2 eq) was added, and the reaction mixture was refluxed for 45 min; after cooling EtOAc was added and the solution washed with water and brine, dried over Na$_2$SO$_4$ and concentrated. The title compound was isolated by chromatography (PE/EtOAc 9:1). Yield (84%); MS (ES$^+$) m/z 504 (M+Na)$^+$.

Step 2: 13-cyclohexyl-5-[2-(dimethylamino)ethyl]-4,5,6,7-tetrahydrothieno[2',3':6,7][1,4]diazocino[1,8-a]indole-10-carboxylic acid A solution of methyl 1-(2-tert-butoxy-2-oxoethyl)-3-cyclohexyl-2-(2-formyl-3-thienyl)-1H-indole-6-carboxylate in THF (0.05 M) was treated with N,N-dimethylethane-1,2-diamine (10 eq) and the pH was adjusted to 6 with AcOH; after stirring for 1 h at RT solvent was removed and the residue dissolved in MeOH (0.05M), then NaCNBH$_3$ (1.5 eq) was added and the mixture was stirred during the weekend. The reaction mixture was diluted with EtOAc and washed with water and brine, dried over Na$_2$SO$_4$ and evaporated affording methyl 1-(2-tert-butoxy-2-oxoethyl)-3-cyclohexyl-2-[2-({[2-(dimethylamino)ethyl]amino}methyl)-3-thienyl]-1H-indole-6-carboxylate.

A 0.03M solution of the latter in DCM/TFA 1:1 was stirred at RT for 4 h, then all volatiles were evaporated; the residue was dissolved in dry DCM (0.1M), i-Pr$_2$EtN (2.4 eq) and HATU (1.2 eq) were added and the mixture was stirred at RT for 2 h. The solution was diluted with EtOAc and washed with water and brine, dried over Na$_2$SO$_4$ and evaporated affording methyl 13-cyclohexyl-5-[2-(dimethylamino)ethyl]-6-oxo-4,5,6,7-tetrahydrothieno[2',3':6,7][1,4]diazocino[1,8-a]indole-10-carboxylate.

A solution of the foregoing crude in dry THF (0.1 M) was treated with BH$_3$Me$_2$S (20 eq, 2M solution in THF) for 2 h at RT; 1.25M HCl in MeOH was added and the mixture was heated at 75° C. for 2.5 h, then volatiles were evaporated to give crude methyl 13-cyclohexyl-5-[2-(dimethylamino) ethyl]4,5,6,7-tetrahydrothieno[2',3':6,7][1,4]diazocino[1,8-a]indole-10-carboxylate. Hydrolysis of the latte performed with 1M aqueous KOH (5 eq) in dioxane (0.1M) at 55° C.; the reaction was complete in 2 h, and the title compound was obtained in 51% yield after RP-HPLC purification and lyophilisation (Conditions: Column: Waters X-TERRA MS C18, 10 micron, 19×150 mm; Gradient: A: H$_2$O+0.1% TFA; B: MeCN+0.1% TFA; 75% A isocratic for 3 min, linear to 20% A in 12 min).
$^1$H NMR (400 MHz, DMSO, 300 K) δ 1.14-1.98 (10H, m), 2.63-2.78 (1H, m), 2.83 (6H, s) 3.23-3.47 (5H, m), 3.59-3.68 (1H, m), 3.78-3.93 (2H, m), 4.46-4.72 (2H, m), 7.20 (1H, d, J 5.0), 7.71 (1H, d, J 8.4), 7.84-7.86 (1H, m), 7.89 (1H, d, J 8.4), 8.14 (1H, s); MS (ES$^+$) m/z 452 (M+H)$^+$.

EXAMPLE 33

Preparation of 13-cyclohexyl-5-[2-(dimethylamino)ethyl]-4,5,6,7-tetrahydrothieno[3',2':6,7][1,4]diazocino[1,8-a]indole-10-carboxylic acid The title compound was prepared following the experimental procedure in Example 32, but using (3-formyl-2-thienyl)boronic acid (1.5 eq) in the coupling step. 45% yield after RP-HPLC purification and lyophilisation (Conditions: Column: Waters X-TERRA MS C18, 10 micron, 19×150 mm; Gradient: A: H$_2$O+0.1% TFA; B: MeCN+0.1% TFA; 75% A isocratic for 3 min, linear to 20% A in 12 min).
$^1$H NMR (400 MHz, DMSO, 300 K) δ 1.21-1.38 (3H, m), 1.60-2.07 (7H, m), 2.81 (6H, s), 2.94-2.99 (1H, m), 3.33-3.67 (6H, m), 3.76-3.86 (2H, m), 4.36-4.40 (1H, m), 4.72-4.77 (1H, m), 7.46 (1H, d, J 5.1), 7.71 (1H, d, J 8.5), 7.87 (1H, d, J 5.1), 7.93 (1H, d, J 8.5), 8.17 (1H, s); MS (ES$^+$) m/z 452 (M+H)$^+$.

EXAMPLE 34

Preparation of 13-cyclohexyl-5-[2-(dimethylamino)ethyl]-4,5,6,7-tetrahydrothieno[3',4':6,7][1,4]diazocino[1,8-a]indole-10-carboxylic acid Step 1: (4-formyl-3-thienyl)boronic acid To a 0.5M solution of B(Oi-Pr)$_3$ (1.2 eq) in toluene/THF 4:1 was added a solution of 2-(4-bromo-3-thienyl)-1,3-dioxolane in toluene/THF 4:1, and the mixture was then cooled to −78° C. BuLi (1.5M in hexanes; 1.2 eq) was then added over 1 h, and the solution kept at this temperature for an additional h, then allowed to warm to −20° C. over 3 h; aq 1N HCl was added and the mixture stirred for an additional h at this temperature. Removal of volatiles gave an aqueous solution that was extracted with DCM; the combined organic phases were then washed with brine, dried over Na$_2$SO$_4$ and concentrated in vacuo. Yield: 95%.
$^1$H NMR (400 MHz, DMSO-d6, 300 K) δ 8.07 (1H, d, J 3.0), 8.55 (2H, b.s), 8.74 (1H, d, J 3.0), 9.98 (1H, s).

Step 2: 13-cyclohexyl-5-[2-(dimethylamino)ethyl]-4,5,6,7-tetrahydrothieno[3',4':6,7][1,4]diazocino[1,8-a]indole-10-carboxylic acid Using the foregoing (4-formyl-3-thienyl)boronic acid the title compound was prepared following the procedures in Example 32. 56% yield after RP-HPLC purification and lyophilisation (Conditions: Column: Waters X-TERRA MS C18, 10 micron, 19×150 mm; Gradient: A: H$_2$O+0.1% TFA;

B: MeCN+0.1% TFA; 75% A isocratic for 3 min, linear to 20% A in 12 min). $^1$H NMR (400 MHz, DMSO, 300 K) δ 1.14-1.38 (3H, m), 1.54-2.06 (7H, m), 2.71-2.78 (1H, m), 2.87 (6H, s), 3.56-3.86 (8H, m), 4.51 (1H, d, J 14.2), 4.74-4.82 (1H, m), 7.72 (1H, d, J 8.5), 7.81 (1H, d, J 2.9), 7.91 (1H, d, J 8.14 (1H, s) 8.17 (1H, d, J 2.9); MS (ES$^+$) m/z 452 (M+H)$^+$.

NO EXAMPLES 35 TO 40

EXAMPLE 41

Preparation of 14-cyclohexyl-5-(2-pyrrolidin-1-ylethoxy)-5,6,7,8-tetrahydroindolo[2,1-a][2]benzazocine-11-carboxylic acid Step 1: Methyl 3-cyclohexyl-2-(2-vinylphenyl)-1H-indole-6-carboxylate Methyl 2-bromo-3-cyclohexyl-1H-indole-6-carboxylate (prepared as described in WO 2004065367) and (2-vinylphenyl)boronic acid (1.5 eq) were dissolved in dioxane (0.07 M) and 2M aqueous Na$_2$CO$_3$ (6 eq) was added. The solution was degassed by bubbling argon, Pd(PPh$_3$)$_2$Cl$_2$ (0.2 eq) was added, and the reaction mixture was refluxed for 1 h; after cooling, EtOAc was added, and the solution washed with water and brine, dried over Na$_2$SO$_4$ and concentrated in vacuo. The title compound was isolated by chromatography (PE/EtOAc 9:1) in 91% yield; MS (ES$^+$) m/z 360 (M+H)$^+$.

Step 2: Methyl 1-but-3-en-1-yl-3-cyclohexyl-2-(2-vinylphenyl)-1H-indole-6-carboxylate To a 0.3M solution of methyl 3-cyclohexyl-2-(2-vinylphenyl)-1H-indole-6-carboxylate in dry DMF, 60% NaH (1.5 eq) in mineral oil was added at 0° C.; after stirring for 45 min at RT, 4-bromobut-1-ene (1.5 eq) was added and the suspension was stirred for 5 h at 40° C. and then 1 day at RT (NaH and 4-bromobut-1-ene were added several times). The mixture was diluted with EtOAc, washed with 1N HCl, water and brine, dried (Na$_2$SO$_4$) and concentrated in vacuo to give, after chromatography (PE/EtOAc 95:5), the title compound (60%) along with recovered starting material (40%); MS (ES$^+$) m/z 414 (M+H)$^+$.

Step 3: Methyl 14-cyclohexyl-7,8-dihydroindolo[2,1-a][2]benzazocine-11-carboxylate Methyl 1-but-3-en-1-yl-3-cyclohexyl-2-(2-vinylphenyl)-1H-indole-6-carboxylate was dissolved in DCM (0.02M) and treated with Zhan catalyst 1 (0.3 eq) at 35° C. for 1 h. After evaporation of solvent in vacuo the residue was purified by chromatography (PE/EtOAc 9:1) to afford the title compound (68%); MS (ES$^+$) m/z 386 (M+H)$^+$.

Step 4: 14-Cyclohexyl-5-(2-pyrrolidin-1-ylethoxy)-5,6,7,8-tetrahydroindolo[2,1-a][2]benzazocine-11-carboxylic acid BH$_3$Me$_2$S (1.6 eq, 2M solution in THF) was added to a 0.2M solution of methyl 14-cyclohexyl-7,8-dihydroindolo[2,1-a][2]benzazocine-11-carboxylate in THF, and the mixture was stirred for 2 h at RT. 3M aq NaOH (3 eq) and 35% H$_2$O$_2$ (3 eq) were added at 0° C., and stirring was continued overnight at RT. After dilution with sat NaHCO$_3$ the aq. phase was extracted with EtOAc, the organic phase was washed with water and brine, dried over Na$_2$SO$_4$ and concentrated in vacuo to give mainly methyl 14-cyclohexyl-5-hydroxy-5,6,7,8-tetrahydroindolo[2,1-a][2]benzazocine-11-carboxylate (with traces of its regioisomer methyl 14-cyclohexyl-6-hydroxy-5,6,7,8-tetrahydroindolo[2,1-a][2]benzazocine-11-carboxylate).

The foregoing crude was dissolved in toluene, 40% aq NaOH (15 eq) and tetrabutyl ammonium bromide (0.25 eq) were added, and the mixture was stirred for 30 min; 1-(2-chloroethyl)pyrrolidine hydrochloride (3 eq) was then added and the resulting mixture heated for 1 day at 70° C.; evaporation to dryness gave a residue from which the title compound was isolated by RP-HPLC (overall yield 10%) (Conditions: Column: Waters X-TERRA MS C18, 10 micron, 19×150 mm; Gradient: A: H$_2$O+0.1% TFA; B: MeCN+0.1% TFA; 75% A isocratic for 3 min, linear to 20% A in 12 min).
$^1$H NMR (400 MHz, DMSO, 300 K) δ 1.16-3.48 (28H, m), 3.78 (1H, d, J 9.0), 4.40-4.45 (1H, m), 7.38 (1H, d, J 7.4), 7.47-7.50 (1H, m), 7.62-7.71 (3H, m), 7.85 (1H, d, J 8.3), 8.07 (1H, s), 9.31 (1H, b.s) 12.59 (1H, b.s); MS (ES$^+$) m/z 487 (M+H)$^+$.

EXAMPLE 42

Preparation of 14-cyclohexyl-6-(2-pyrrolidin-1ylethoxy)-5,6,7,8-tetrahydroindolo[2,1-a][2]benzazocine-11-carboxylic acid Step 1: Methyl 14-cyclohexyl-5,6-dihydroxy-5,6,7,8-tetrahydroindolo[2,1-a][2]benzazocine-11-carboxylate A solution (0.11 M) of methyl 14-cyclohexyl-7,8-dihydroindolo[2,1-a][2]benzazocine-11-carboxylate (prepared as in Example 41, Step 3) in acetone/THF/H$_2$O (1/1/1) was treated with N-methylmorpholine-N-oxide (1.2 eq), followed by OsO$_4$ (4% wt in H$_2$O, 0.1 eq) and left stirring at RT overnight. The clear solution was then treated with 10% wt Na$_2$SO$_3$ and left stirring for 30 min, then diluted with H$_2$O and extracted with EtOAc. The organic phase was washed with brine, dried over Na$_2$SO$_4$ and evaporated i. vac. to give the clean title compound as a creamy solid; MS (ES$^+$) m/z 420 (M+H)$^+$.

Step 2: Methyl 15-cyclohexyl-6-oxo-4b,7a,8,9-tetrahydro[1,3]dioxolo[4,5-e]indolo[2,1-a][2]benzazocine-12-carboxylate A solution (0.05 M) of the foregoing compound in DCM was treated with Et$_3$N (4 eq), and cooled to −50° C. Triphosgene (0.4 eq) was added and the solution was allowed to warm to RT over 30 min. After 2 h at RT, satd. NaHCO$_3$ was added and the solution extracted with EtOAc. The organic phase was washed with H$_2$O, brine, dried over Na$_2$SO$_4$ and evaporated i. vac. to leave title compound; MS (ES$^+$) m/z 446 (M+H)$^+$.

Step: 3 Methyl 14-cyclohexyl-6-hydroxy-5,6,7,8-tetrahydroindolo[2,1-a][2]benzazocine-11-carboxylate A solution (0.02 M) of the foregoing compound in acetone/MeOH (3/1) was treated with Raney-Ni (slurry in water) and the vigorously stirred reaction mixture was hydrogenated at 1 atm H$_2$. After 48 h the solid was filtered and the filtrates evaporated in vacuo to leave the title compound (yield 26%); MS (ES$^+$) m/z 404 (M+H)$^+$.

Step 4: 14-cyclohexyl-6-(2-pyrrolidin-1ylethoxy)-5,6,7,8-tetrahydroindolo[2,1-a][2]benzazocine-11-carboxylate 14-cyclohexyl-6-(2-pyrrolidin-1ylethoxy)-5,6,7,8-tetrahydroindolo[2,1-a][2]benzazocine-11-carboxylate was prepared as described for its benzylic analogue in Example 41, Step 4, starting from methyl 14-cyclohexyl-6-hydroxy-5,6,7,8-tetrahydroindolo[2,1-a][2]benzazocine-11-carboxylate (yield 36%)
$^1$H NMR (400 MHz, DMSO, 300 K) δ 1.16-1.39 (3H, m), 1.43-1.58 (2H, m), 1.64-1.75 (2H, m), 1.82-2.18 (9H, m), 2.18-2.34 (1H, m), 2.57-2.68 (1H, m), 2.99-3.11 (3H, m), 3.12-3.29 (2H, m), 3.50-3.65 (4H, m), 3.73-3.94 (2H, m), 4.26-4.45 (1H, m), 7.31-7.56 (4H, m), 7.66-7.68 (1H, d, J 8.4), 7.86-7.88 (1H, d, J 8.4), 8.08 (1H, s); MS (ES$^+$) m/z 487.4 (M+H)$^+$.

NO EXAMPLE 43

EXAMPLE 44

14-cyclohexyl-3-fluoro-6-[(4-methylpiperazin-1-yl)acetyl]-5,6,7,8-tetrahydroindolo[2,1-a][2,5]benzodiazocine-11-carboxylic acid

Step 1: 14-cyclohexyl-3-fluoro-5,6,7,8-tetrahydroindolo[2,1-a][2,5]benzodiazocine-11-carboxylic acid To a solution of methyl 14-cyclohexyl-3-fluoro-5,6,7,8-tetrahydroindolo[2,1-a][2,5]benzodiazocine-11-carboxylate (prepared as described in Example 18, Step 5) in DCM (0.01 M) was added dropwise 5 eq of a solution of BBr$_3$ in DCM (1 M). The solution was stirred at RT for 30 min. Volatiles were removed in vacuo. The crude was then purified by automated RP-MS-HPLC (stationary phase: column Waters XTERRA prep. C18, 5 μm, 30×100 mm. Mobile phase: MeCN/H$_2$O buffered with 0.1% TFA). Fractions containing the pure compound were combined and freeze dried to afford the title compound as a white powder (20%); MS (ES$^+$) m/z 393 (M+H)$^+$.

Step 2: 14-cyclohexyl-3-fluoro-6-[(4-methylpiperazin-1-yl)acetyl]-5,6,7,8-tetrahydroindolo[2,1-a][2,5]benzodiazocine-11-carboxylic acid To a solution of 3 eq of (4-methylpiperazin-1-yl)acetic acid in DCM (0.2 M), 4 eq of DIPEA and 2 eq of HATU were added and the mixture stirred at RT for 1 h. Then a solution of 1 eq of 11-carboxy-14-cyclohexyl-3-fluoro-5,6,7,8-tetrahydroindolo[2,1-a][2,5]benzodiazocin-6-ium trifluoroacetate in DMF (0.06 M) and 1 eq of DIPEA was added and the mixture stirred at RT overnight. Volatiles were removed in vacuo. The crude was then purified by automated RP-MS-HPLC (stationary phase: column Waters SYMMETRY prep. C18, 7 μm, 19×300 mm. Mobile phase: MeCN/H$_2$O buffered with 0.1% TFA). Fractions containing the pure compound were combined and freeze dried to afford the title compound as a white powder (51%).
$^1$H NMR (400 MHz, DMSO-d$_6$+TFA, 330 K) δ 1.14-1.1.16 (m, 1H), 1.29-1.32 (m, 3H), 1.54-1.57 (m, 1H), 1.67-1.73 (m, 2H), 1.81-1.94 (m, 3H), 2.56-2.59 (m, 1H), 2.87 (s, 3H), 3.28-3.36 (m, 6H), 3.46-3.49 (m, 4H), 3.65 (dd, J 15.2, 9.6, 1H), 4.01-4.05 (m, 1H), 4.12 (d, J 16.0, 1H), 4.27 (d, J 16.0, 1H), 4.73 (dd, J 15.6, 4.0, 1H), 5.14 (d, J 15.6, 1H), 7.30-7.35 (m, 1H), 7.45 (dd, J 8.4, 5.6, 1H), 7.57 (dd, J 9.6, 2.4, 1H), 7.73 (d, J 8.4, 1H), 7.88 (d, J 8.4, 1H), 8.14 (s, 1H); MS (ES$^+$) m/z 533 (M+H)$^+$.

EXAMPLE 45

14-cyclohexyl-6-{[2-(dimethylamino)ethyl]sulfonyl}-3-fluoro-5,6,7,8-tetrahydroindolo[2,1-a][2,5]benzodiazocine-11-carboxylic acid A solution of 1 eq of 11-carboxy-14-cyclohexyl-3-fluoro-5,6,7,8-tetrahydroindolo[2,1-a][2,5]benzodiazocin-6-ium trifluoroacetate (prepared as described in Example 44, Step 1) in DCM (plus some drops of MeCN and DMF) (0.08 M) was added to a solution of 1.1 eq of 2-chloro-ethansulfonyl chloride in DCM (0.08 M) and 2.2 eq of Et$_3$N and the mixture stirred at RT for 5 mins. At which time a solution of dimethylamine 2 M in THF (5 eq) was added and the mixture stirred at RT overnight. Volatiles were removed in vacuo. The crude was then purified by automated RP-MS-HPLC (stationary phase: column Waters SYMMETRY prep. C18, 7 μm, 19×300 mm. Mobile phase: MeCN/H$_2$O buffered with 0.1% TFA). Fractions containing the pure compound were combined and freeze dried to afford the title compound as a white powder (16%).
$^1$H NMR (600 MHz, DMSO-d$_6$+TFA, 300 K) δ 1.09-1.14 (m, 1H), 1.21-1.32 (m, 3H), 1.54-1.56 (m, 1H), 1.66-1.72 (m, 2H), 1.81-1.91 (m, 3H), 2.53-2.56 (s, 1H), 2.80 (s, 6H), 3.29 (dd, J 13.7, 10.4, 1H), 3.37 (d, J 14.8, 1H), 3.43-3.47 (m, 2H), 3.55-3.60 (m, 3H), 4.05 (dd, J 14.3, 4.7, 1H), 4.68 (d, J 14.8, 1H), 4.83 (dd, J 15.8, 4.7, 1H), 7.35-7.40 (m, 2H), 7.48 (dd, J 8.3, 5.5, 1H), 7.72 (d, J 8.4, 1H), 7.88 (d, J 8.4 1H), 8.15 (s, 1H); MS (ES$^+$) m/z 528 (M+H)$^+$.

EXAMPLE 46

14-cyclohexyl-3-fluoro-6-{[(2R)-1-methylpyrrolidin-2-yl]methyl}-5,6,7,8-tetrahydroindolo[2,1-a][2,5]benzodiazocine-11-carboxylic acid

Step 1: methyl 14-cyclohexyl-3-fluoro-6-(1-methyl-D-prolyl)-5,6,7,8-tetrahydroindolo[2,1-a][2,5]benzodiazocine-11-carboxylate To a solution of 1 eq of methyl-14-cyclohexyl-3-fluoro-5,6,7,8-tetrahydroindolo[2,1-a][2,5]benzodiazocin-11-carboxylate (prepared as described in Example 18, Step 5) in DCM (0.06 M), 1.5 eq of 1-methyl-D-proline (prepared according to literature precedent J. Org. Chem. 2003, 68, 2652) in DCM (0.2 M), 1.5 eq of DIPEA and 1.5 eq of TBTU were added and the mixture stirred at RT overnight. Volatiles were removed in vacuo and the crude was used in the next step without further purification; MS (ES$^+$) m/z 518 (M+H)$^+$.

Step 2: methyl 14-cyclohexyl-3-fluoro-6-{[(2R)-1-methylpyrrolidin-2-yl]methyl}-5,6,7,8-tetrahydroindolo[2,1-a][2,5]benzodiazocine-11-carboxylate To a solution of methyl 14-cyclohexyl-3-fluoro-6-(1-methyl-D-prolyl)-5,6,7,8-tetrahydroindolo[2,1-a][2,5]benzodiazocine-11-carboxylate in THF (0.02 M), 3×5 eq of BH$_3$.THF (1 M solution in THF) were added sequentially over a period of 48 h. The solution was allowed to stir at RT and monitored until no starting material was visible by RP-LC-MS. MeOH (0.02 M) and a 1.25 M solution of HCl in MeOH (0.24 M) were added carefully and the mixture heated at reflux for 2 h. The volume of the solution was reduced in vacuo, before diluting with EtOAc. The organic phase was washed with aqueous NaHCO$_3$ solution and brine, before being dried over Na$_2$SO$_4$, filtered and the solvent evaporated in vacuo to afford the title compound. The crude was used in the next step without further purification (quant); MS (ES$^+$) m/z 504 (M+H)$^+$.

Step 3: 14-cyclohexyl-3-fluoro-6-{[(2R)-1-methylpyrrolidin-2-yl]methyl}-5,6,7,8-tetrahydroindolo[2,1-a][2,5]benzodiazocine-11-carboxylic acid Methyl 14-cyclohexyl-3-fluoro-6-{[(2R)-1-methylpyrrolidin-2-yl]methyl}-5,6,7,8-tetrahydroindolo[2,1-a][2,5]benzodiazocine-11-carboxylate was dissolved in a solution of dioxane: H$_2$O 2O (1:1) (0.1 M) and to that solution aqueous KOH (3 eq, 5 N) was added. The solution was stirred at 60° C. for 3 h. The solvent was evaporated in vacuo. The crude was then purified by automated RP-MS-HPLC (stationary phase: column Waters SYMMETRY prep. C18, 7 μm, 19×300 mm. Mobile phase: MeCN/H$_2$O buffered with 0.1% TFA). Fractions containing the pure compound were combined and freeze dried to afford the title compound as a white powder (18%).
$^1$H NMR (400 MHz, DMSO-d$_6$+TFA, 330 K) δ 1.16-1.20 (m, 1H), 1.32-1.34 (m, 2H), 1.55-1.57 (m, 1H), 1.68-2.07 (m, 8H), 2.67-2.8 (m, 1H), 2.92 (s, 3H), 2.99-3.24 (m, 4H), 3.35-3.40 (m, 2H), 3.53-3.74 (m, 4H), 3.80-3.83 (m, 1H), 4.05-4.10 (m, 1H), 4.59-4.66 (m, 1H), 7.36-7.41 (m, 1H), 7.45-7.50 (m, 1H), 7.66-7.68 (m, 1H), 7.72 (d, J 8.4, 1H), 7.88 (d, J 8.4, 1H), 8.13 (s, 1H); MS (ES$^+$) m/z 490 (M+H)$^+$.

EXAMPLE 47

14-cyclohexyl-3-fluoro-6-(1H-imidazol-1-ylacetyl)-5,6,7,8-tetrahydroindolo[2,1-a][2,5]benzodiazocine-11-carboxylic acid Step 1: methyl 14-cyclohexyl-3-fluoro-6-(1H-imidazol-1-ylacetyl)-5,6,7,8-tetrahydroindolo[2,1-a][2,5]benzodiazocine-11-carboxylate To a solution of 1 eq of methyl-14-cyclohexyl-3-fluoro-5,6,7,8-tetrahydroindolo[2,1-a][2,5]benzodiazocin-11-carboxylate (prepared as described in Example 18, Step 5) in DCM (0.06 M), 1.1 eq of imidazo-1-yl acetic acid in DCM (0.05 M), 3 eq of DIPEA and 1.5 eq of TBTU were added and the mixture stirred at RT overnight. Volatiles were removed in vacuo and the crude material was used in the next step without further purification; MS (ES$^+$) m/z 515 (M+H)$^+$.

Step 2: 14-cyclohexyl-3-fluoro-6-(1H-imidazol-1-ylacetyl)-5,6,7,8-tetrahydroindolo[2,1-a][2,5]benzodiazocine-11-carboxylic acid Methyl 14-cyclohexyl-3-fluoro-6-(1H-imidazol-1-ylacetyl)-5,6,7,8-tetrahydroindolo[2,1-a][2,5]benzodiazocine-11-carboxylate was dissolved in a solution of dioxane: H$_2$O (1:1) (0.1 M) and to that solution aqueous KOH (3 eq, 5 N) were added. The solution was stirred at 60° C. for 3 h. The solvent was evaporated in vacuo. The crude was then purified by automated RP-MS-HPLC (stationary phase: column Waters SYMMETRY prep. C18, 7 μm, 19×300 mm. Mobile phase: MeCN/H$_2$O buffered with 0.1% TFA). Fractions containing the pure compound were combined and freeze dried to afford the title compound as a white powder (41%).
$^1$H NMR (400 MHz, DMSO-d$_6$+TFA, 300 K) δ 1.11-1.15 (m, 1H), 1.29-1.31 (m, 2H), 1.50-1.53 (m, 1H), 1.68-1.71 (m, 2H), 1.80-1.93 (m, 4H), 2.53-2.58 (m, 1H), 3.37-3.46 (m, 2H), 3.70 (dd, J 15.6, 10.0, 1H), 4.14-4.17 (m, 1H), 4.78 (dd, J 15.6, 4.0, 1H), 5.06-5.14 (m, 2H), 5.36 (d, J 16.4, 1H), 7.33-7.38 (m, 1H), 7.43-7.52 (m, 3H), 7.64 (s, 1H), 7.72 (d, J 8.6, 1H), 7.92 (d, J 8.6, 1H), 8.21 (s, 1H), 8.80 (s, 1H); MS (ES$^+$) m/z 501 (M+H)$^+$.

EXAMPLE 48

14-cyclohexyl-6-(N,N-dimethylglycyl)-5,6,7,8-tetrahydroindolo[2,1-a][2,5]benzodiazocine-11-carboxylic acid Step 1: methyl 3-cyclohexyl-1-(1,3-dioxolan-2-ylmethyl)-2-{2-[(hydroxyimino)methyl]phenyl}-1H-indole-6-carboxylate To a solution of methyl methyl 3-cyclohexyl-1-(1,3-dioxolan-2-ylmethyl)-2-(2-formylphenyl)-1H-indole-6-carboxylate (prepared in analogous fashion to Example 4, Step 2, using 2-formylphenylboronic acid) in EtOH (0.05 M), were added aqueous solutions of sodium carbonate (2M; 1.3 eq) followed by hydroxylamine hydrochloride (2M; 1.3 eq). The reaction was stirred at RT for 2 h, before the EtOH was reduced in vacuo and the residue partitioned between EtOAc and water. The aqueous fraction was extracted a second time with EtOAc and the combined organics washed with water and then brine before being dried over Na$_2$SO$_4$, filtered and concentrated in vacuo to afford the title compound (95%); MS (ES$^+$) m/z 463 (M+H)$^+$.

Step 2: methyl 2-[2-(aminomethyl)phenyl]-3-cyclohexyl-1-(1,3-dioxolan-2-ylmethyl)-1H-indole-6-carboxylate Platinum (IV) oxide (20 mol %) was added as a slurry in AcOH under N$_2$ to a solution of methyl 3-cyclohexyl-1-(1,3-dioxolan-2-ylmethyl)-2-{2-[(hydroxyimino)methyl]phenyl}-1H-indole-6-carboxylate in AcOH (0.07 M). The atmosphere in the reaction vessel was charged with H$_2$ at 50 psi pressure and the reaction agitated on a Parr apparatus for 48 h. The reaction was then filtered under N$_2$ through a plug of celite, washing well with AcOH, and the filtered solution concentrated in vacuo to afford the title compound (100%); MS (ES$^+$) m/z 449 (M+H)$^+$.

Step 3: methyl 14-cyclohexyl-5,6,7,8-tetrahydroindolo[2,1-a][2,5]benzodiazocine-11-carboxylate 3M aqueous HCl (16 eq) was added to a solution of methyl 2-[2-(aminomethyl)phenyl]-3-cyclohexyl-1-(1,3-dioxolan-2-ylmethyl)-1H-indole-6-carboxylate in THF (0.03 M). The reaction was heated with stirring at reflux for 24 h, before being allowed to cool to RT, basified with aqueous NaOH (2N) and extracted into EtOAc (3 times). The combined organics were washed with water, brine, dried over Na$_2$SO$_4$, filtered and concentrated in vacuo to afford the crude intermediate as a yellow oil. This oil was taken up immediately in MeOH (0.1 M, 1 eq) and the solution acidified to pH 4 with glacial acetic acid. After stirring for 20 min, NaCNBH$_3$ (1.3 eq) was added and the reaction stirred for a further 1 h. The reaction was quenched by addition of sat. aq. NaHCO$_3$ and extracted into EtOAc (×3). The combined organic extracts were washed with brine before being dried over Na$_2$SO$_4$, filtered and concentrated in vacuo. Purification by flash column chromatography (2.5% MeOH/0.5% Et$_3$N/CH$_2$Cl$_2$) gave the title compound as a pale yellow solid (46%); MS (ES$^+$) m/z 389 (M+H)$^+$ Step 4: methyl 14-cyclohexyl-6-(N,N-dimethylgly-cyl)-5,6,7,8-tetrahydroindolo[2,1-a][2,5]benzodiazo-cine-11-carboxylate Procedure carried out in analogous fashion to Example 18, Step 6. The title compound was obtained as a pale yellow oil and taken on without further purification (quantitative); MS (ES$^+$) m/z 475 (M+H)$^+$.

Step 5: 14-cyclohexyl-6-(N,N-dimethylglycyl)-5,6,7,8-tetrahydroindolo[2,1-a][2.5]benzodiazocine-11-carboxylic acid Procedure carried out in analogous fashion to Example 18, Step 7. Purification was by RP-HPLC (stationary phase: column Waters XTERRA prep. MS C18, 5 µm, 19×100 mm. Mobile phase: MeCN/H$_2$O buffered with 0.1% TFA). Fractions containing the pure compound were combined and freeze dried to afford the TFA salt of the title compound as a white powder (27% over steps 4 and 5).

$^1$H NMR (400 MHz, d6-DMSO+TFA, 300 K) δ 1.10-1.12 (m, 1H), 1.24-1.36 (m, 2H), 1.51-1.54 (m, 1H), 1.66-1.72 (m, 2H), 1.82-1.84 (m, 1H), 1.92-1.97 (m, 3H), 2.54-2.59 (m, 1H), 2.77 (s, 6H), 3.30-3.39 (m, 2H obscured by H$_2$O), 3.58-3.64 (m, 1H), 3.92-3.95 (m, 1H), 4.11 (d, J 15.9, 1H), 4.35 (d, J 15.9, 1H), 4.71-4.76 (m, 1H), 5.19 (d, J 14.1, 1H), 7.39-7.42 (m, 1H), 7.48-7.53 (m, 2H), 7.71-7.74 (m, 1H), 7.82-7.84 (m, 1H), 7.92 (d, J 8.6, 1H), 8.2 (s, 1H); MS (ES$^+$) m/z 460 (M+H)$^+$

EXAMPLE 49

14-cyclohexyl-6-[(1-methyl-1H-pyrazol-4-yl)me-thyl]-5,6,7,8-tetrahydroindolo[2,1-a][2,5]benzodia-zocine-11-carboxylic acid Step 1: methyl 14-cyclohexyl-6-[(1-methyl-1H-pyrazol-4-yl)methyl]-5,6,7,8-tetrahydroindolo[2,1-a][2,5]benzodiazocine-11-carboxylate To a solution of methyl 14-cyclohexyl-5,6,7,8-tetrahy-droindolo[2,1-a][2,5]-benzodiazocine-11-carboxylate (prepared as described in Example 48, Step 3) in MeOH (0.06 M), 1-methyl-1H-pyrazole-4-carbaldehyde (3 eq) was added and the pH adjusted to pH 4 with acetic acid. The solution was stirred at RT for 30 mins before addition of NaBH$_3$CN (1.5 eq). The reaction was stirred at RT for 16 h. The reaction was quenched with saturated aqueous NaHCO$_3$ and extracted with EtOAc (×2). The combined organics were washed with brine, dried (Na$_2$SO$_4$), filtered and concentrated in vacuo to give the title compound as a viscous oil (quantitative); MS (ES$^+$) m/z 483 (M+H)$^+$ Step 2: 14-cyclohexyl-6-[(1-methyl-1H-pyrazol-4-yl)methyl]-5,6,7,8-tetrahydroindolo[2,1-a][2,5]benzo-diazocine-11-carboxylic acid BBr$_3$ (5 eq, 1 M sol. in CH$_2$Cl$_2$) was added to a solution of methyl 14-cyclohexyl-6-[(1-methyl-1H-pyrazol-4-yl)me-thyl]-5,6,7,8-tetrahydroindolo[2,1-a][2,5]benzodiazocine-11-carboxylate in CH$_2$Cl$_2$ (0.06 M), and the mixture stirred at RT for 40 mins. The volatiles were removed in vacuo. The crude was then purified by prep RP-HPLC (stationary phase: column Waters XTERRA prep. C18, 5 um, 19×150 mm. Mobile phase: MeCN/H$_2$O buffered with 0.1% TFA). Fractions containing the pure compound were combined and freeze dried to afford the title compound as a white powder in a 7% yield (over two steps).

$^1$H NMR (400 MHz, DMSO-d$_6$+TFA, 300 K) δ 1.11-1.15 (m, 1H), 1.23-1.36 (m, 2H), 1.52-1.54 (m, 1H), 1.66-1.73 (m, 2H), 1.82-1.84 (m, 1H), 1.88-1.98 (m, 3H), 2.62-2.67 (m, 1H), 3.36-3.38 (m, 1H), 3.58-3.75 (m, 3H), 3.88 (s, 3H) 4.43 (s, 2H), 4.49-4.52 (m, 1H), 4.82-4.86 (m, 1H), 7.47-7.51 (m, 2H), 7.64-7.67 (m, 3H), 7.74 (d, J 8.1, 1H), 7.92-7.95 (m, 2H), 8.23 (s, 1H); MS (ES$^+$) m/z 469 (M+H)$^+$

EXAMPLE 50

14-cyclohexyl-6-{2-[methyl(pyridin-3-ylmethyl)amino]ethyl}-5,6,7,8-tetrahydroindolo[2,1-a][2,5]benzodiazocine-11-carboxylic acid Step 1: Tert-butyl N-{2-[3-cyclohexyl-1-(2,2-dimethoxyethyl)-6-(methoxycarbonyl)-1H-indol-2-yl]benzyl}glycinate To a solution of methyl 3-cyclohexyl-1-(2,2-dimethoxy-ethyl)-2-(2-formylphenyl)-1H-indole-6-carboxylate (prepared as described in Example 20, Step 2) in DCE (0.09 M), tert-butyl glycinate hydrochloride salt (1.5 eq) was added followed by NaBH(OAc)$_3$ (3 eq). The solution was stirred at RT for 2 days. The reaction was quenched with aqueous NaHCO$_3$ and extracted with EtOAc (×2). The combined organic phases were washed with brine, dried (Na$_2$SO$_4$), filtered and concentrated in vacuo to give the title compound as a viscous oil (quantitative); MS (ES$^+$) m/z 565 (M+H)$^+$ Step 2: methyl 6-(2-tert-butoxy-2-oxoethyl)-14-cy-clohexyl-5,6,7,8-tetrahydroindolo[2,1-a][2.5]benzo-diazocine-11-carboxylate Dimethoxy acetal deprotection and ring closure to the cyclic amine was performed in directly analogous fashion to previous examples (eg, Example 20, Step 4) to give the title compound; MS (ES$^+$) m/z 503 (M+H)$^+$.

Step 3: [14-cyclohexyl-11-(methoxycarbonyl)-7,8-dihydroindolo[2,1-a][2,5]benzodiazocin-6(5H)-yl]acetic acid To a solution of methyl 6-(2-tert-butoxy-2-oxoethyl)-14-cyclohexyl-5,6,7,8-tetrahydroindolo[2,1-a][2,5]benzodiazo-cine-11-carboxylate in a 1:1 mixture DCM/H$_2$O (0.05 M) was added a large excess (>100 eq) of TFA and the solution heated for 4 h at 45° C. The volatiles were then removed in vacuo and the crude product was used in the next step without further purification; MS (ES$^+$) m/z 447 (M+H)$^+$.

Step 4: methyl 14-cyclohexyl-6-{2-[methyl(pyridin-3-ylmethyl)amino]-2-oxoethyl}-5,6,7,8-tetrahydroin-dolo[2,1-a][2,5]benzodiazocine-11-carboxylate To a solution of [14-cyclohexyl-11-(methoxycarbonyl)-7,8-dihydroindolo[2,1-a][2,5]benzodiazocin-6(5H)-yl]acetic acid in DCM (0.05 M), 3.5 eq of DIPEA, 1.5 eq of HATU and 1.5 eq of N-methyl-1-pyridin-3-ylmethanamine were added and the mixture was stirred overnight at RT. The solution was portioned between DCM and brine. The aqueous phase was re-extracted with DCM (twice) and the combined organics then dried over Na$_2$SO$_4$, filtered and concentrated in vacuo. The crude was used in the next step without further purification; MS (ES$^+$) m/z 551 (M+H)$^+$.

Step 5: methyl 14-cyclohexyl-6-{2-[methyl(pyridin-3-ylmethyl)amino]ethyl}-5,6,7,8-tetrahydroindolo[2,1-a][2.5]benzodiazocine-11-carboxylate To a solution of methyl 14-cyclohexyl-6-{2-[methyl(pyridin-3-ylmethyl)amino]-2-oxoethyl}-5,6,7,8-tetrahydroindolo[2,1-a][2,5]benzodiazocine-11-carboxylate in THF (0.05 M), $BH_3.Me_2S$ (20 eq, 2 M solution in THF) was added. The solution was stirred overnight at RT. The solution was carefully quenched by adding 1.25 N HCl in MeOH until effervescence subsided. Then the volatiles were driven off by boiling the mixture to dryness. The crude residue was used directly in the next step; MS ($ES^+$) m/z 537 $(M+H)^+$.

Step 6: 14-cyclohexyl-6-{2-[methyl(pyridin-3-ylmethyl)amino]ethyl}-5,6,7,8-tetrahydroindolo[2,1-a][2,5]benzodiazocine-11-carboxylic acid To a solution of methyl 14-cyclohexyl-6-{2-[methyl(pyridin-3-ylmethyl)amino]ethyl}-5,6,7,8-tetrahydroindolo[2,1-a][2,5]benzodiazocine-11-carboxylate in a mixture of MeOH:THF (4:1; 0.05 M), 10 eq of 1 N NaOH were added. The solution was heated at 60° C. for 3 h. The volatiles were evaporated in vacuo and the crude was then purified by automated prep RP-HPLC (stationary phase: column Waters XTERRA prep. C18, 5 um, 19×100 mm. Mobile phase: MeCN/$H_2O$ buffered with 0.1% TFA). Fractions containing the pure compound were combined and freeze dried to afford the title compound in 10% yield (three steps).

$^1$H NMR (400 MHz, DMSO-$d_6$+TFA, 300 K) δ1.10-1.20 (m, 1H), 1.25-1.40 (m, 2H), 1.50-1.60 (m, 1H), 1.60-1.70 (m, 2H), 1.80-1.90 (m, 1H), 1.90-2.05 (m, 3H), 2.60-2.65 (m, 1H), 2.67 (s, 3H), 3.40-3.55 (m, 3H), 3.60-3.82 (m, 5H), 4.41 (s, 2H), 4.44-4.50 (m, 1H), 4.80-4.90 (m, 1H), 7.45-7.55 (m, 1H), 7.60-7.70 (m, 2H), 7.74 (d, J 8.4, 1H), 7.79-7.85 (m, 1H), 7.93 (d, J 8.4, 1H), 7.95-8.00 (m, 1H), 8.19 (s, 1H), 8.40-8.50 (m, 1H), 8.85-8.92 (m, 1H), 8.94 (s, 1H); MS ($ES^+$) m/z 523 $(M+H)^+$.

EXAMPLE 51

13-cyclohexyl-5-[2-(dimethylamino)ethyl]-4,5,6,7-tetrahydrofuro[3',2':6,7][1,4]diazocino[1,8-a]indole-10-carboxylic acid Step 1: methyl 1-(2-tert-butoxy-2-oxoethyl)-3-cyclohexyl-2-(3-formyl-2-furyl)-1H-indole-6-carboxylate To a solution of methyl 2-bromo-1-(2-tert-butoxy-2-oxoethyl)-3-cyclohexyl-1H-indole-6-carboxylate (prepared as described in Example 1, Step 1) in dioxane (0.04 M) was added $Na_2CO_3$ (5 eq, 2 M aqueous solution), 3-formylfuran-2-boronic acid (1.4 eq) and bis(triphenylphosphine)palladium(II) dichloride (0.2 eq). The mixture was heated at reflux for 20 mins, at which point the heat was removed and the reaction cooled slightly to allow addition of a further 1 eq of boronic acid. The reaction was then heated for a further 1 h at reflux. Again, the reaction was cooled slightly to allow addition of a further 0.5 eq of boronic acid. After heating for a further 30 mins, the reaction was allowed to cool to RT, filtered and the filtrate diluted with EtOAc. The organic phase was washed with $H_2O$ and dried ($Na_2SO_4$) before being filtered and concentrated in vacuo. The crude was purified by flash chromatography (10-20% EtOAc/PE) to afford the title compound as an oil (38%); MS ($ES^+$) m/z 466 $(M+H)^+$, 488 $(M+Na)^+$.

Step 2: methyl 1-(2-tert-butoxy-2-oxoethyl)-3-cyclohexyl-2-[3-({[2-(dimethylamino)ethyl]amino}methyl)-2-furyl]-1H-indole-6-carboxylate To a solution of methyl 1-(2-tert-butoxy-2-oxoethyl)-3-cyclohexyl-2-(3-formyl-2-furyl)-1H-indole-6-carboxylate in THF (0.08 M), 10 eq of N,N-dimethylethane-1,2-diamine were added and the pH adjusted to pH 6 with acetic acid. The solution was stirred at RT for 1 h before being concentrated in vacuo. The residue was taken up in MeOH to give a 0.08 M solution. 1.5 eq of $NaBH_3CN$ were added and the mixture stirred at RT for 16 h. The reaction was quenched with saturated aqueous $NaHCO_3$ and extracted (twice) with EtOAc. The combined organic phases were washed with brine before being dried over $Na_2SO_4$, filtered and concentrated in vacuo to give the title compound as a viscous oil (quant); MS ($ES^+$) m/z 538 $(M+H)^+$.

Step 3: methyl 13-cyclohexyl-5-[2-(dimethylamino)ethyl]-6-oxo-4,5,6,7-tetrahydrofuro[3',2':6,7][1,4]diazocino[1,8-a]indole-10-carboxylate To a solution of methyl 1-(2-tert-butoxy-2-oxoethyl)-3-cyclohexyl-2-[3-({[2-(dimethyl amino)ethyl]amino}methyl)-2-furyl]-1H-indole-6-carboxylate in $CH_2Cl_2/H_2O$ (1:1) (0.04 M) was added TFA (80 eq). After 16 h a further 80 eq of TFA were added. After a further 8 h, RP-HPLC analysis of the reaction mixture showed complete removal of the $^t$Butyl ester. The volatiles were removed in vacuo adding $Et_2O$ to aid evaporation of residual TFA. The residue was taken up in $CH_2Cl_2$ to give a 0.08 M solution. 3.5 eq of $iPr_2NEt$ and 3.5 eq of HATU were added and the mixture stirred at RT for 16 h. The reaction was quenched with saturated aqueous $NaHCO_3$ and extracted (twice) with EtOAc. The combined organic phases were washed with HCl (1N), aqueous $NaHCO_3$ and brine before being dried over $Na_2SO_4$, filtered and concentrated in vacuo to give the title compound as a viscous oil (quant); MS ($ES^+$) m/z 464 $(M+H)^+$.

Step 4: methyl 13-cyclohexyl-5-[2-(dimethylamino)ethyl]4,5,6,7-tetrahydrofuro[3',2'; 6,7][1,4]diazocino[1,8-a]indole-10-carboxylate To a solution of methyl 13-cyclohexyl-5-[2-(dimethylamino)ethyl]-6-oxo-4,5,6,7-tetra hydrofuro[3',2':6,7][1,4]diazocino[1,8-a]indole-10-carboxylate in THF (0.08 M), 10 eq of $BH_3.Me_2S$ (2 M sol. in THF) were added and the mixture was stirred at RT for 2 h. The solution was carefully quenched by adding 1.25 M HCl in MeOH until effervescence subsided. Then the volatiles were driven off by boiling the mixture to dryness. The crude residue was used directly in the next step; MS ($ES^+$) m/z 450 $(M+H)^+$.

Step 5: 13-cyclohexyl-5-[2-(dimethylamino)ethyl]-4,5,6,7-tetrahydrofuro[3',2':6,7][1,4]diazocino[1,8-a]indole-10-carboxylic acid To a solution of methyl 13-cyclohexyl-5-[2-(dimethylamino)ethyl]-4,5,6,7-tetrahydrofuro[3',2':6,7][1,4]diazocino[1,8-a]indole-10-carboxylate in MeOH (0.07 M), 15 eq 1N NaOH was added. The solution was stirred at 70° C. for 6 h. The reaction was acidified to pH 2 with HCl and the solvent was evaporated in vacuo. The crude was then purified by prep RP-HPLC (stationary phase: column Waters XTERRA prep. C18, 5 um, 19×150 mm. Mobile phase: MeCN/$H_2O$ buffered with 0.1% TFA). Fractions containing the pure compound were combined and freeze dried to afford the title compound as a brown powder in 8% yield (over two steps).

$^1$H NMR (400 MHz, DMSO-d$_6$+TFA, 300 K) δ 1.23-1.37 (m, 3H), 1.65-1.86 (m, 7H), 2.83 (s, 6H), 2.91-2.98 (m, 1H), 3.50-3.59 (m, 4H), 3.69-3.74 (m, 2H), 4.17-4.26 (m, 2H), 4.33-4.52 (m, 2H), 6.89 (s, 1H), 7.72 (d, J 8.4, 1H), 7.87 (d, J 8.4, 1H), 7.95 (s, 1H), 8.20 (s, 1H); MS (ES$^+$) m/z 436 (M+H)$^+$.

EXAMPLE 52

15-cyclohexyl-6-[2-(dimethylamino)ethyl]-7-oxo-6,7,8,9-tetrahydro-5H-indolo[2,1-a][2,6]benzodiazonine-12-carboxylic acid Step 1: 3-[2-bromo-3-cyclohexyl-6-(methoxycarbonyl)-1H-indol-1-yl]propanoic acid NaH (3.5 eq, 60% dispersion in mineral oil) was added to a solution of methyl 2-bromo-3-cyclohexyl-1H-indole-6-carboxylate (prepared as described in WO 2004065367, from commercially available methyl indole-6-carboxylate) in DMF (0.2 M) and the solution allowed to stir at RT for 1 h. Then 3-bromopropanoic acid (1.1 eq) was added and the mixture stirred at RT for 2 h. DMF was concentrated in vacuo and the residue taken up in EtOAc. The organic phase was washed with 1 N HCl and then brine before being dried (Na$_2$SO$_4$), filtered and the solvent evaporated in vacuo. The title compound was used crude in the next step; MS (ES$^+$) m/z 408 (M+H)$^+$, m/z 410 (M+H)$^+$.

Step 2: methyl 2-bromo-3-cyclohexyl-1-(3-methoxy-3-oxopropyl)-1H-indole-6-carboxylate 1.6 eq of (Trimethylsilyl)diazomethane (2 M solution in hexanes) was added dropwise to a solution of 3-[2-bromo-3-cyclohexyl-6-(methoxycarbonyl)-1H-indol-1-yl]propanoic acid in a mixture toluene:MeOH (7:3; 0.2 M) and the solution stirred at RT for 1 h. Excess trimethylsilyl diazomethane was quenched with acetic acid and then the solution was concentrated in vacuo. The crude was purified by flash chromatography (Biotage cartridge Si40S, 1:9 EtOAc/PE) to afford the title compound (63% over two steps); MS (ES$^+$) m/z 422 (M+H)$^+$, m/z 424 (M+H)$^+$.

Step 3: methyl 3-cyclohexyl-2-(2-formylphenyl)-1-(3-methoxy-3-oxopropyl)-1H-indole-6-carboxylate To a solution of methyl 2-bromo-3-cyclohexyl-1-(3-methoxy-3-oxopropyl)-1H-indole-6-carboxylate in dioxane (0.15 M) were added Na$_2$CO$_3$ (6 eq, 2 M aqueous solution), 1.6 eq of (2-formylphenyl)boronic acid and 0.2 eq of bis(triphenylphosphine)-palladium(II) dichloride. The mixture was heated at reflux for 1 h. The reaction mixture was filtered and the filtrate diluted with EtOAc. The organic phase was washed with brine and dried (Na$_2$SO$_4$) before being filtered and concentrated in vacuo. The crude was purified by flash chromatography (Biotage cartridge Si25M, 1:9 EtOAc/PE) to afford the title compound (40%); MS (ES$^+$) m/z 448 (M+H)$^+$.

Step 4: methyl 3-cyclohexyl-2-[2-({[2-(dimethylamino)ethyl]amino}methyl)phenyl]-1-(3-methoxy-3-oxopropyl)-1H-indole-6-carboxylate To a solution of methyl 3-cyclohexyl-2-(2-formylphenyl)-1-(3-methoxy-3-oxopropyl)-1H-indole-6-carboxylate in THF (0.1 M), N,N-dimethylethane-1,2-diamine (10 eq) was added and the pH adjusted to pH=6 with HOAc. The solution was stirred at RT for 1 h, before the THF was concentrated in vacuo and the residue taken up in MeOH. To the methanolic solution (0.1 M) NaBH$_3$CN (2 eq) was added and the mixture stirred at RT overnight. The reaction mixture was diluted with EtOAc. The organic phase was washed with NaHCO$_3$ (s.s.), H$_2$O and brine. The organic phase was dried (Na$_2$SO$_4$), filtered and concentrated in vacuo. The title compound was used as crude in the next step; MS (ES$^+$) m/z 520 (M+H)$^+$.

Step 5: 3-[3-cyclohexyl-2-[2-({[2-(dimethylamino)ethyl]amino}methyl)phenyl]-6-(methoxycarbonyl)-1H-indol-1-yl]propanoic acid Lithium hydroxide monohydrate (1 eq) was added to a solution of methyl 3-cyclohexyl-2-[2-({[2-(dimethylamino)ethyl]amino}methyl)phenyl]-1-(3-methoxy-3-oxopropyl)-1H-indole-6-carboxylate in a mixture THF:H$_2$O (4:1, 0.1 M). The mixture stirred at RT for 1 h. The reaction was quenched with 1 N HCl and the solvent evaporated in vacuo. The residue was washed with the minimum amount of Et$_2$O and the solid residue filtered to obtain the title compound (82%); MS (ES$^+$) m/z 506 (M+H)$^+$.

Step 6: methyl 15-cyclohexyl-6-[2-(dimethylamino)ethyl]-7-oxo-6,7,8,9-tetrahydro-5H-indolo[2,1-a][2,6]benzodiazonine-12-carboxylate To a solution of 3-[3-cyclohexyl-2-[2-({[2-(dimethylamino)ethyl]amino}methyl)phenyl]-6-(methoxycarbonyl)-1H-indol-1-yl]propanoic acid in DCM (0.01 M), 3.5 eq of DIPEA and 1.5 eq of HATU were added and the mixture was stirred at RT for 4 h. The solution was diluted with EtOAc and HCl (1 N), the aqueous phase was re-extracted with EtOAc (twice) and the combined organics then washed with brine, dried over Na$_2$SO$_4$, filtered and concentrated in vacuo. The crude was used in the next step without further purification; MS (ES$^+$) m/z 488 (M+H)$^+$.

Step 7: 15-cyclohexyl-6-[2-(dimethylamino)ethyl]-7-oxo-6,7,8,9-tetrahydro-5H-indolo[2,1-a][2,6]benzodiazonine-12-carboxylic acid To a solution of methyl 15-cyclohexyl-6-[2-(dimethylamino)ethyl]-7-oxo-6,7,8,9-tetrahydro-5H-indolo[2,1-a][2,6]benzodiazonine-12-carboxylate in DCM (0.04 M), 7 eq BBr$_3$ (1 M solution in DCM) were added. The solution stirred at RT for 20 mins. The solvent was evaporated in vacuo. The crude was then purified by automated prep RP-HPLC (stationary phase: column Waters XTERRA prep. C18, 5 um, 19×100 mm. Mobile phase: MeCN/H$_2$O buffered with 0.1% TFA). Fractions containing the pure compound were combined and freeze dried to afford the title compound (15% over three steps).

$^1$H NMR (400 MHz, DMSO-d$_6$+TFA, 300 K) δ 1.10-1.45 (m, 3H), 1.45-1.55 (m, 1H), 1.63-2.1 (m, 6H), 2.30-2.40 (m, 1H partially obscured by DMSO peak), 2.70 (s, 6H), 2.70-2.77 (m, 1H), 2.80-3.00 (m, 1H), 3.00-3.20 (m, 1H), 3.20-3.45 (m, 3H), 4.00-4.20 (m, 1H), 4.30-4.50 (m, 1H), 4.50-4.70 (m, 1H), 5.10-5.20 (m, 1H), 7.26 (d, J 7.2, 1H), 7.45-7.60

(m, 3H), 7.63 (d, J 8.4, 1H), 7.81 (d, J 8.4, 1H), 8.11 (s, 1H), 8.91 (br s, 1H), 12.6 (br s, 1H); MS (ES+) m/z 474 (M+H)+.

NO EXAMPLES 53 TO 66

EXAMPLE 67

14-cyclohexyl-6[2-(dimethylamino)ethyl]-N-(morpholin-4-ylsulfonyl)-5,6,7,8-tetrahydroindolo[2,1-a][2,5]benzodiazocine-11-carboxamide Step 1: morpholine-4-sulfonamide To a solution of morpholine (1 eq) in DME (0.3 M), 5 eq of sulfamide were added and the solution was heated at 100° C. overnight. The volatiles were removed in vacuo, the residue taken up in EtOAc and the organic phase washed with $H_2O$ and then brine. The organic phase was dried over $Na_2SO_4$, filtered and concentrated in vacuo to give the title compound (17%); MS (ES+) m/z 167 (M+H)+

Step 2: 14-cyclohexyl-6[2-(dimethylamino)ethyl]-N-(morpholin-4-ylsulfonyl)-5,6,7,8-tetrahydroindolo[2,1-a][2,5]benzodiazocine-11-carboxamide To 11-carboxy-14-cyclohexyl-6-[2-(dimethylammonio)ethyl]-5,6,7,8-tetrahydroindolo-[2,1-a][2,5]benzodiazocin-6-ium dichloride (1 eq) (prepared from the product described in Example 20, Step 5, by iterative freeze drying in the presence of aqueous HCl) in DCM (0.06 M) was added morpholine-4-sulfonamide (1.5 eq), EDCI (1.5 eq) and DMAP (1.5 eq). The solution was stirred at RT overnight. The solvent was evaporated in vacuo and the crude was purified by automated RP-MS-HPLC (stationary phase: column Waters SYMMETRY prep. C18, 7 μm, 19×300 mm. Mobile phase: MeCN/$H_2O$ buffered with 0.1 TFA). Fractions containing the pure compound were combined and freeze dried to afford the title compound as a white powder (31%).

$^1$H NMR (400 MHz, DMSO-$d_6$+TFA, 330 K) δ 1.11-1.17 (m, 1H), 1.29-1.35 (m, 2H), 1.58-1.67 (m, 1H), 1.70-1.84 (m, 2H), 1.85-1.98 (m, 4H), 2.61-2.67 (m, 1H), 2.88 (s, 6H), 3.35-3.38 (m, 5H), 3.50-3.68 (m, 10H), 3.75-3.82 (m, 1H), 4.33 (d, J 14.0, 1H), 4.71 (dd, J 16.4, 4.4, 1H), 7.48-7.50 (m, 1H), 7.63-7.65 (m, 2H), 7.73 (d, J 8.4, 1H), 7.82-7.84 (m, 1H), 7.92 (d, J 8.4, 1H), 8.21 (s, 1H), 11.59 (brs, 1H); MS (ES+) m/z 594 (M+H)+.

The following tables contain further examples:

TABLE 1

| Example no. | Name | m/z (ES+) |
|---|---|---|
| 101 | 14-cyclohexyl-6-methyl-7-oxo-5,6,7,8-tetrahydroindolo[2,1-a][2,5]benzodiazocine-11-carboxylic acid | 403 |
| 102 | 14-cyclohexyl-3-methoxy-6-methyl-7-oxo-5,6,7,8-tetrahydroindolo[2,1-a][2,5]benzodiazocine-11-carboxylic acid | 433 |
| 103 | 14-cyclohexyl-6-[2-(dimethylamino)ethyl]-3-methoxy-7-oxo-5,6,7,8-tetrahydroindolo[2,1-a][2,5]benzodiazocine-11-carboxylic acid | 490 |
| 104 | 14-cyclohexyl-6-[3-(dimethylamino)propyl]-7-oxo-5,6,7,8-tetrahydroindolo[2,1-a][2,5]benzodiazocine-11-carboxylic acid | 474 |
| 105 | 14-cyclohexyl-7-oxo-6-(2-piperidin-1-ylethyl)-5,6,7,8-tetrahydroindolo[2,1-a][2,5]benzodiazocine-11-carboxylic acid | 500 |

TABLE 1-continued

| Example no. | Name | m/z (ES+) |
|---|---|---|
| 106 | 14-cyclohexyl-6-(2-morpholin-4-ylethyl)-7-oxo-5,6,7,8-tetrahydroindolo[2,1-a][2,5]benzodiazocine-11-carboxylic acid | 502 |
| 107 | 14-cyclohexyl-6-[2-(diethylamino)ethyl]-7-oxo-5,6,7,8-tetrahydroindolo[2,1-a][2,5]benzodiazocine-11-carboxylic acid | 488 |
| 108 | 14-cyclohexyl-6-(1-methylpiperidin-4-yl)-7-oxo-5,6,7,8-tetrahydroindolo[2,1-a][2,5]benzodiazocine-11-carboxylic acid | 486 |
| 109 | 14-cyclohexyl-N-[(dimethylamino)sulfonyl]-7-oxo-6-(2-piperidin-1-ylethyl)-5,6,7,8-tetrahydroindolo[2,1-a][2,5]benzodiazocine-11-carboxamide | 606 |
| 110 | 14-cyclohexyl-6-[2-(dimethylamino)ethyl]-N-[(dimethylamino)sulfonyl]-7-oxo-5,6,7,8-tetrahydroindolo[2,1-a][2,5]benzodiazocine-11-carboxamide | 566 |
| 111 | 14-cyclopentyl-6-[2-(dimethylamino)ethyl]-7-oxo-5,6,7,8-tetrahydroindolo[2,1-a][2,5]benzodiazocine-11-carboxylic acid | 446 |
| 112 | 13-cyclohexyl-5-[2-(dimethylamino)ethyl]]-6-oxo-4,5,6,7-tetrahydrofuro[3',2':6,7][1,4]diazocino[1,8-a]indole-10-carboxylic acid | 450 |
| 113 | 14-cyclohexyl-6-(1-isopropylpyrrolidin-3-yl)- 7-oxo-5,6,7,8-tetrahydroindolo[2,1-a][2,5]benzodiazocine-11-carboxylic acid | 500 |
| 114 | 14-cyclohexyl-6-[(1-ethylpyrrolidin-2-yl)methyl]-7-oxo-5,6,7,8-tetrahydroindolo[2,1-a][2,5]benzodiazocine-11-carboxylic acid | 500 |
| 115 | 14-cyclohexyl-6-(1-methylpyrrolidin-3-yl)-7-oxo-5,6,7,8-tetrahydroindolo[2,1-a][2,5]benzodiazocine-11-carboxylic acid | 472 |

TABLE 2

| Example no. | Name | m/z (ES+) |
|---|---|---|
| 201 | 14-cyclohexyl-5,6,7,8-tetrahydroindolo[2,1-a][2,5]benzodiazocine-11-carboxylic acid | 375 |
| 202 | 6-allyl-14-cyclohexyl-3-methoxy-5,6,7,8-tetrahydroindolo[2,1-a][2,5]benzodiazocine-11-carboxylic acid | 443 |
| 203 | 14-cyclopentyl-6-[2-(dimethylamino)ethyl]-5,6,7,8-tetrahydroindolo[2,1-a][2,5]benzodiazocine-11-carboxylic acid | 432 |
| 204 | 14-cyclohexyl-6-[2-(dimethylamino)ethyl]-5,6,7,8-tetrahydroindolo[2,1-a][2,5]benzodiazocine-11-carboxylic acid | 446 |
| 205 | 13-cyclohexyl-5-methyl-4,5,6,7-tetra-hydro-furo[3',2':6,7][1,4]diazocino[1,8-a]indole-10-carboxylic acid | 379 |
| 206 | N-(benzylsulfonyl)-14-cyclohexyl-6-[2-(dimethylamino)ethyl]-5,6,7,8-tetrahydroindolo[2,1-a][2,5]benzodiazocine-11-carboxamide | 599 |
| 207 | 14-cyclohexyl-6-{2-[methyl(1-methylpyrrolidin-3-yl)amino]ethyl}-5,6,7,8-tetrahydroindolo[2,1-a][2,5]benzodiazocine-11-carboxylic acid | 515 |
| 208 | [blank] | |
| 209 | 14-cyclohexyl-6-[2-(dimethylamino)-2-oxoethyl]-5,6,7,8-tetrahydroindolo[2,1-a][2,5]benzodiazocine-11-carboxylic acid | 460 |
| 210 | 14-cyclohexyl-6-[(1-oxidopyridin-4-yl)methyl]-5,6,7,8-tetrahydroindolo[2,1-a][2,5]benzodiazocine-11-carboxylic acid | 482 |
| 211 | 14-cyclohexyl-6-(cyclopropylmethyl)-5,6,7,8-tetrahydroindolo[2,1-a][2,5]benzodiazocine-11-carboxylic acid | 429 |

TABLE 2-continued

| Example no. | Name | m/z (ES+) |
|---|---|---|
| 212 | 14-cyclohexyl-3-methoxy-6-(2-morpholin-4-ylethyl)-5,6,7,8-tetrahydroindolo[2,1-a][2,5]benzodiazocine-11-carboxylic acid | 518 |
| 213 | 14-cyclohexyl-6-(2,2-dimethoxyethyl)-5,6,7,8-tetrahydroindolo[2,1-a][2,5]benzodiazocine-11-carboxylic acid | 463 |
| 214 | [blank] | |
| 215 | 14-cyclohexyl-6-(cyclopropylmethyl)-3-methoxy-5,6,7,8-tetrahydroindolo[2,1-a][2,5]benzodiazocine-11-carboxylic acid | 459 |
| 216 | 14-cyclohexyl-6-(1-methylpiperidin-4-yl)-5,6,7,8-tetrahydroindolo[2,1-a][2,5]benzodiazocine-11-carboxylic acid | 472 |
| 217 | 3-chloro-14-cyclohexyl-6-methyl-5,6,7,8-tetrahydroindolo[2,1-a][2,5]benzodiazocine-11-carboxylic acid | 423 |
| 218 | 14-cyclohexyl-6-[2-(dimethylamino)ethyl]-N-(ethylsulfonyl)-5,6,7,8-tetrahydroindolo[2,1-a][2,5]benzodiazocine-11-carboxamide | 537 |
| 219 | 14-cyclohexyl-6-[2-(dimethylamino)ethyl]-N-[(dimethylamino)sulfonyl]-5,6,7,8-tetrahydroindolo [2,1-a][2,5]benzodiazocine-11-carboxamide | 552 |
| 220 | 14-cyclohexyl-6-[2-(dimethylamino)ethyl]-3-(pyridin-2-yloxy)-5,6,7,8-tetrahydro-indolo[2,1-a][2,5]benzodiazocine-11-carboxylic acid | 539 |
| 221 | 14-cyclohexyl-6-[2-(dimethylamino)ethyl]-3-(pyridin-3-ylmethoxy)-5,6,7,8-tetrahydroindolo[2,1-a][2,5]benzodiazocine-11-carboxylic acid | 553 |
| 222 | 14-cyclohexyl-6-[2-(dimethylamino)ethyl]-3-(pyrazin-2-yloxy)-5,6,7,8-tetrahydro-indolo[2,1-a][2,5]benzodiazocine-11-carboxylic acid | 540 |
| 223 | 14-cyclohexyl-6-[2-(dimethylamino)ethyl]-3-(pyridin-2-ylmethoxy)-5,6,7,8-tetrahydroindolo[2,1-a][2,5]benzodiazocine-11-carboxylic acid | 553 |
| 224 | 14-cyclohexyl-6-[2-(dimethylamino)ethyl]-3-(pyridin-4-ylmethoxy)-5,6,7,8-tetrahydroindolo[2,1-a][2,5]benzodiazocine-11-carboxylic acid | 553 |
| 225 | 14-cyclohexyl-6-isopropyl-3-(pyridazin-3-ylmethoxy)-5,6,7,8-tetrahydroindolo[2,1-a][2,5]benzodiazocine-11-carboxylic acid | 525 |
| 226 | 14-cyclohexyl-6-ethyl-3-(pyridin-2-ylmethoxy)-5,6,7,8-tetrahydroindolo[2,1-a][2,5]benzodiazocine-11-carboxylic acid | 510 |
| 227 | 14-cyclohexyl-6-isopropyl-3-(pyrimidin-2-ylmethoxy)-5,6,7,8-tetrahydroindolo[2,1-a][2,5]benzodiazocine-11-carboxylic acid | 525 |
| 228 | 14-cyclohexyl-6-cyclopropyl-3-(pyridin-2-ylmethoxy)-5,6,7,8-tetrahydroindolo[2,1-a][2,5]benzodiazocine-11-carboxylic acid | 522 |
| 229 | 14-cyclohexyl-3-[2-(dimethylamino)-2-oxoethoxy]-6-isopropyl-5,6,7,8-tetrahydroindolo[2,1-a][2,5]benzodiazocine-11-carboxylic acid | 518 |
| 230 | 14-cyclohexyl-6-(1-methylpyrrolidin-3-yl)-5,6,7,8-tetrahydroindolo[2,1-a][2,5]benzodiazocine-11-carboxylic acid | 458 |
| 231 | 14-cyclohexyl-6-[(1-ethylpyrrolidin-2-yl)methyl]-5,6,7,8-tetrahydroindolo[2,1-a][2,5]benzodiazocine-11-carboxylic acid | 486 |
| 232 | 14-cyclohexyl-6-[2-(dimethylamino)ethyl]-3-ethoxy-5,6,7,8-tetrahydroindolo[2,1-a][2,5]benzodiazocine-11-carboxylic acid | 490 |
| 233 | 3-(benzyloxy)-14-cyclohexyl-6-[2-(dimethylamino)ethyl]-5,6,7,8-tetrahydroindolo[2,1-a][2,5]benzodiazocine-11-carboxylic acid | 552 |
| 234 | 14-cyclohexyl-6-isopropyl-5,6,7,8-tetrahydroindolo[2,1-a][2,5]benzodiazocine-11-carboxylic acid | 417 |
| 235 | 13-cyclohexyl-5-methyl-4,5,6,7-tetrahydro-thieno[3',2':6,7][1,4]diazocino[1,8-a]indole-10-carboxylic acid | 395 |
| 236 | 13-cyclohexyl-5-(2-morpholin-4-ylethyl)-4,5,6,7-tetrahydrothieno[3',2':6,7][1,4]diazocino[1,8-a]indole-10-carboxylic acid | 440 |
| 237 | 13-cyclohexyl-5-methyl-4,5,6,7-tetrahydro-furo[2',3':6,7][1,4]diazocino[1,8-a]indole-10-carboxylic acid | 379 |
| 238 | 14-cyclohexyl-6-(2-hydroxyethyl)-5,6,7,8-tetrahydroindolo[2,1-a][2,5]benzodiazocine-11-carboxylic acid | 419 |
| 239 | 14-cyclohexyl-6-[2-(dimethylamino)ethyl]-5,6,7,8-tetrahydropyrido-[2',3':6,7][1,4]diazocino[1,8-a]indole-11-carboxylic acid | 447 |

TABLE 3

| Example no. | Name | m/z (ES+) |
|---|---|---|
| 301 | 15-cyclohexyl-6-[2-(dimethylamino)ethyl]-7-oxo-6,7,8,9-tetrahydro-5H-indolo[2,1-a][2,6]benzodiazonine-12-carboxylic acid | 474 |
| 302 | 15-cyclohexyl-8-oxo-6,7,8,9-tetrahydro-5H-indolo[2,1-a][2,5]benzodiazonine-12-carboxylic acid | 403 |

TABLE 4

| Example no. | Name | m/z (ES+) |
|---|---|---|
| 401 | [blank] | |
| 402 | 14-cyclohexyl-5-[(2-pyrrolidin-1-ylethyl)amino]-5,6,7,8-tetrahydroindolo[2,1-a][2]benzazocine-11-carboxylic acid | 486 |
| 403 | 3-chloro-14-cyclohexyl-7-[[2-(dimethylamino)ethyl](methyl)amino]-7,8-dihydro-6H-indolo[1,2-e][1,5]benzoxazocine-11-carboxylic acid | 510 |
| 404 | 14-cyclohexyl-7-{[2-(dimethylamino)ethyl]amino}-3-fluoro-7,8-dihydro-6H-indolo[1,2-e][1,5]benzoxazocine-11-carboxylic acid | 480 |
| 405 | 14-cyclohexyl-7-[[2-(dimethylamino)ethyl](ethyl)amino]-7,8-dihydro-6H-indolo[1,2-e][1,5]benzoxazocine-11-carboxylic acid | 490 |
| 406 | 14-cyclohexyl-7-[[2-(dimethylamino)ethyl](isopropyl)amino]-7,8-dihydro-6H-indolo[1,2-e][1,5]benzoxazocine-11-carboxylic acid | 504 |
| 407 | [blank] | |
| 408 | [blank] | |
| 409 | 14-cyclohexyl-7-[(1-isopropylpyrrolidin-3-yl)(methyl)amino]-7,8-dihydro-6H-indolo[1,2-e][1,5]benzoxazocine-11-carboxylic acid | 516 |
| 410 | 14-cyclohexyl-7-{methyl[2-(methylamino)ethyl]amino}-7,8-dihydro-6H-indolo[1,2-e][1,5]benzoxazocine-11-carboxylic acid | 462 |
| 411 | 14-cyclohexyl-7-{methyl[2-(4-methylpiperazin-1-yl)ethyl]amino}-7,8-dihydro-6H-indolo[1,2-e][1,5]benzoxazocine-11-carboxylic acid | 531 |

TABLE 4-continued

| Example no. | Name | m/z (ES+) |
|---|---|---|
| 412 | 14-cyclohexyl-7-[methyl(2-piperazin-1-ylethyl)amino]-7,8-dihydro-6H-indolo[1,2-e][1,5]benzoxazocine-11-carboxylic acid | 517 |
| 413 | 14-cyclohexyl-7-[2-(4-methylpiperazin-1-yl)ethoxy]-7,8-dihydro-6H-indolo[1,2-e][1,5]benzoxazocine-11-carboxylic acid | 518 |
| 414 | 14-cyclohexyl-7-[(N,N-dimethylglycyl)(methyl)amino]-7,8-dihydro-6H-indolo[1,2-e][1,5]benzoxazocine-11-carboxylic acid | 490 |
| 415 | 14-cyclohexyl-7-[(N,N-dimethyl-glycyl)amino]-7,8-dihydro-6H-indolo[1,2-e][1,5]benzoxazocine-11-carboxylic acid | 476 |
| 416 | 3-chloro-14-cyclohexyl-7-{[2-(dimethylamino)ethyl]amino}-7,8-dihydro-6H-indolo[1,2-e][1,5]benzoxazocine-11-carboxylic acid | 497 |
| 417 | 14-cyclohexyl-7-[4-(2-methoxy-ethyl)piperazin-1-yl]-7,8-dihydro-6H-indolo[1,2-e][1,5]benzoxazocine-11-carboxylic acid | 518 |
| 418 | 14-cyclohexyl-2-fluoro-7-(4-methyl-piperazin-1-yl)-7,8-dihydro-6H-indolo[1,2-e][1,5]benzoxazocine-11-carboxylic acid | 492 |
| 419 | 14-cyclohexyl-7-[(1-methylpiperidin-4-yl)amino]-7,8-dihydro-6H-indolo[1,2-e][1,5]benzoxazocine-11-carboxylic acid | 488 |
| 420 | 14-cyclohexyl-7-{[3-(dimethyl-amino)propyl]amino}-7,8-dihydro-6H-indolo[1,2-e][1,5]benzoxazocine-11-carboxylic acid | 476 |
| 421 | 14-cyclohexyl-7-{[2-(dimethylamino)ethyl]amino}-2-fluoro-7,8-dihydro-6H-indolo[1,2-e][1,5]benzoxazocine-11-carboxylic acid | 480 |
| 422 | 7-[(2-aminoethyl)amino]-14-cyclohexyl-7,8-dihydro-6H-indolo[1,2-e][1,5]benzoxazocine-11-carboxylic acid | 434 |
| 423 | 14-cyclohexyl-7-(dimethylamino)-7,8-dihydro-6H-indolo[1,2-e][1,5]benzoxazocine-11-carboxylic acid | 419 |
| 424 | 14-cyclohexyl-7-(cyclopropylamino)-7,8-dihydro-6H-indolo[1,2-e][1,5]benzoxazocine-11-carboxylic acid | 431 |
| 425 | 14-cyclohexyl-7-(methylamino)-7,8-dihydro-6H-indolo[1,2-e][1,5]benzoxazocine-11-carboxylic acid | 405 |
| 426 | 7-amino-14-cyclohexyl-7,8-dihydro-6H-indolo[1,2-e][1,5]benzoxazocine-11-carboxylic acid | 391 |
| 427 | 14-cyclohexyl-7-(2-morpholin-4-ylethoxy)-7,8-dihydro-6H-indolo[1,2-e][1,5]benzoxazocine-11-carboxylic acid | 505 |
| 428 | 14-cyclohexyl-7-[(2-morpholin-4-ylethyl)amino]-7,8-dihydro-6H-indolo[1,2-e][1,5]benzoxazocine-11-carboxylic acid | 504 |
| 429 | 14-cyclohexyl-7-(2-methoxyethoxy)-7,8-dihydro-6H-indolo[1,2-e][1,5]benzoxazocine-11-carboxylic acid | 450 |
| 430 | 14-cyclohexyl-7-[(2-methoxyethyl)amino]-7,8-dihydro-6H-indolo[1,2-e][1,5]benzoxazocine-11-carboxylic acid | 449 |
| 431 | 14-cyclohexyl-7-[2-(N,N-dimethyl-acetamido)amino]-7,8-dihydro-6H-indolo[1,2-e][1,5]benzoxazocine-11-carboxylic acid | 476 |
| 432 | 14-cyclohexyl-7-(methyl{2-[methyl(phenyl)amino]ethyl}amino)-7,8-dihydro-6H-indolo[1,2-e][1,5]benzoxazocine-11-carboxylic acid | 538 |

TABLE 5

| Example no. | Name | m/z (ES+) |
|---|---|---|
| 501 | 14-cyclohexyl-3-fluoro-6-(1-methyl-L-prolyl)-5,6,7,8-tetrahydroindolo[2,1-a][2,5]benzodiazocine-11-carboxylic acid | 504 |
| 502 | 14-cyclohexyl-3-fluoro-6-(N,N,2-trimethylalanyl)-5,6,7,8-tetrahydroindolo[2,1-a][2,5]benzodiazocine-11-carboxylic acid | 506 |
| 503 | 14-cyclohexyl-3-fluoro-6-(morpholin-4-ylacetyl)-5,6,7,8-tetrahydroindolo[2,1-a][2,5]benzodiazocine-11-carboxylic acid | 520 |
| 504 | 14-cyclohexyl-3-fluoro-6-(1-methyl-D-prolyl)-5,6,7,8-tetrahydroindolo[2,1-a][2,5]benzodiazocine-11-carboxylic acid | 504 |
| 505 | 14-cyclohexyl-6-(N,N-dimethyl-β-alanyl)-3-fluoro-5,6,7,8-tetrahydroindolo[2,1-a][2,5]benzodiazocine-11-carboxylic acid | 492 |
| 506 | 14-cyclohexyl-3-fluoro-6-[(1-methylazetidin-3-yl)carbonyl]-5,6,7,8-tetrahydroindolo[2,1-a][2,5]benzodiazocine-11-carboxylic acid | 490 |
| 507 | 14-cyclohexyl-6-(N,N-dimethylalanyl)-3-fluoro-5,6,7,8-tetrahydroindolo[2,1-a][2,5]benzodiazocine-11-carboxylic acid | 492 |
| 508 | 3-chloro-14-cyclohexyl-6-(N,N-dimethylglycyl)-5,6,7,8-tetrahydroindolo[2,1-a][2,5]benzodiazocine-11-carboxylic acid | 494 |
| 509 | 14-cyclohexyl-6-(N,N-dimethylglycyl)-3-methoxy-5,6,7,8-tetrahydroindolo[2,1-a][2,5]benzodiazocine-11-carboxylic acid | 490 |

The invention claimed is:

1. A compound of formula (Ii) or a pharmaceutically acceptable salt thereof:

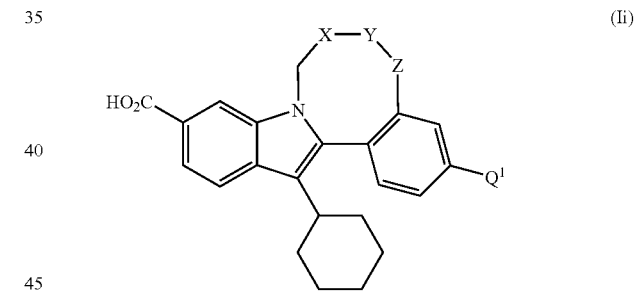

(Ii)

wherein
X is —CHR$^{14}$—;
Y is —CH$_2$—;
Z is O;
Q$^1$ is absent or is halogen, hydroxy, C$_{1-6}$alkyl, C$_{1-6}$alkoxy, (CH$_2$)$_{0-3}$aryl, heteroaryl, CONR$^c$R$^d$, (CH$_2$)$_{0-3}$NR$^c$R$^d$, O(CH$_2$)$_{0-3}$C$_{3-8}$cycloalkyl, O(CH$_2$)$_{1-3}$NR$^c$R$^d$, O(CH$_2$)$_{0-3}$CONR$^c$R$^d$, O(CH$_2$)$_{0-3}$CO$_2$H, O(CH$_2$)$_{0-3}$aryl, O(CH$_2$)$_{0-3}$heteroaryl, OCHR$^e$R$^f$ or O(CH$_2$)$_{0-3}$S(O)$_2$(CH$_2$)$_{0-3}$NR$^c$R$^d$;
R$^{14}$ is NR$^{16}$R$^{17}$;
R$^c$ and R$^d$ are independently selected from hydrogen, C$_{1-6}$alkyl and C(O)C$_{1-6}$alkyl;
or R$^c$ and R$^d$, together with the nitrogen atom to which they are attached, form a heteroaliphatic ring of 4 to 7 ring atoms, optionally containing 1 or 2 more heteroatoms independently selected from O and S and/or 1 or 2 groups independently selected from NH and NC$_{1-4}$alkyl, where said ring is optionally substituted by halogen, hydroxy, C$_{1-4}$alkyl or C$_{1-4}$alkoxy;

$R^e$ and $R^f$ are independently selected from hydrogen, $C_{1-4}$alkyl and $C_{1-4}$alkoxy;

or $R^e$ and $R^f$ are linked by a heteroatom selected from N, O and S to form a heteroaliphatic ring of 4 to 7 ring atoms, where said ring is optionally substituted by halogen, hydroxy, $C_{1-4}$alkyl or $C_{1-4}$alkoxy;

$R^{16}$ and $R^{17}$ are independently selected from hydrogen, $C_{1-6}$alkyl, and $(CH_2)_{0-4}NR^{18}R^{19}$, $(CH_2)_{0-3}Het$, $(CH_2)_{0-3}$heteroaryl, $(CH_2)_{0-3}C(O)(CH_2)_{0-3}NR^{18}R^{19}$ or $(CH_2)_{0-3}C_{3-8}$cycloalkyl, optionally substituted by $C_{1-6}$alkyl, $(CH_2)_{0-3}OH$ or $(CH_2)_{0-3}C_{1-6}$alkoxy;

or $R^{16}$ and $R^{17}$, together with the nitrogen atom to which they are attached, form a heteroaliphatic ring of 4 to 7 ring atoms, which ring may optionally contain 1 or 2 more heteroatoms selected from O and S and/or 1 or 2 groups independently selected from $S(O)$, $S(O)_2$, NH, $NC_{1-4}$alkyl and $N(CH_2)_{0-3}C_{1-4}$alkoxy, and which ring is optionally substituted by halogen, hydroxy, $C_{1-4}$alkyl or $C_{1-4}$alkoxy;

$R^{18}$ and $R^{19}$ are independently selected from hydrogen, and $C_{1-6}$alkyl and heteroaryl;

or $R^{18}$ and $R^{19}$, together with the nitrogen atom to which they are attached, form a heteroaliphatic ring of 4 to 7 ring atoms, which ring may optionally contain 1 or 2 more heteroatoms selected from O and S and/or 1 or 2 groups selected from $S(O)$, $S(O)_2$, NH and $NC_{1-4}$alkyl, and which ring is optionally substituted by halogen, hydroxy, $C_{1-4}$alkyl or $C_{1-4}$alkoxy.

2. The compound as claimed in claim 1, wherein $NR^{16}R^{17}$ is selected from the group consisting of:

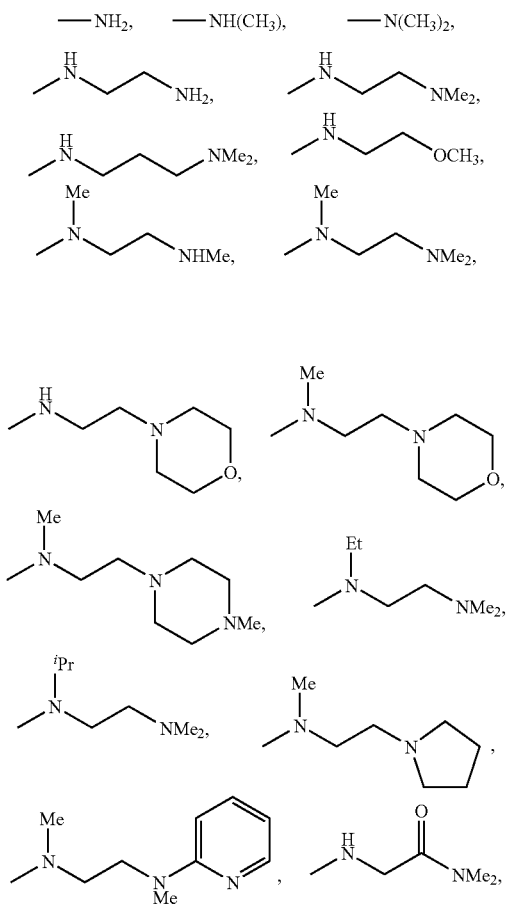

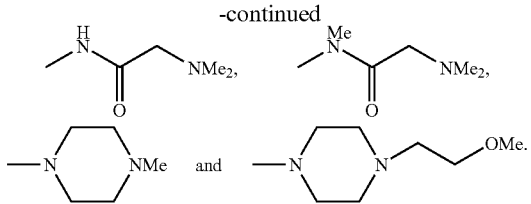

3. The compound as claimed in claim 2, wherein $Q^1$ is absent or is fluorine, chlorine, hydroxy, methoxy, ethoxy, i-propoxy, $OCH_2C(O)N(CH_3)_2$, benzyloxy, O-pyridinyl, $OCH_2$pyridinyl, $OCH_2$pyridazinyl, $OCH_2$pyrimidinyl or O-pyrazinyl.

4. The compound as claimed in claim 2, wherein $Q^1$ is absent or is halogen, hydroxy, $C_{1-6}$alkoxy, $O(CH_2)_{0-3}C(O)(CH_2)_{0-3}N(C_{1-4}$alkyl$)_2$, $O(CH_2)_{0-3}$aryl or $O(CH_2)_{0-3}$heteroaryl.

5. A compound of formula (Ia):

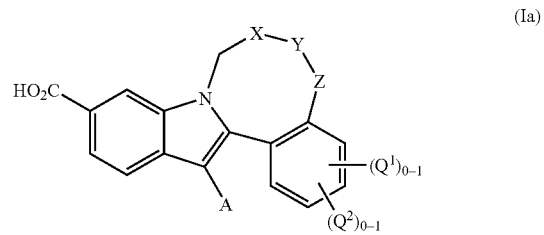

(Ia)

wherein

A is cyclohexyl, optionally substituted by halogen, hydroxy, $C_{1-4}$alkyl or $C_{1-4}$alkoxy;

$Q^1$ is halogen, hydroxy, $C_{1-6}$alkyl or $C_{1-6}$alkoxy;

$Q^2$ is absent;

X is C=O or $—CR^{14}R^{15}—$;

Y is $—CR^{14a}R^{15a}—$;

Z is O;

$R^{14}$, $R^{14a}$, $R^{15}$ and $R^{15a}$ are each independently selected from hydrogen, hydroxy, $C_{1-6}$alkyl, $C_{2-6}$alkenyl, $C_{1-6}$alkoxy, $C(O)C_{1-6}$alkyl, Het, $(CH_2)_{0-3}NR^{16}R^{17}$, $C(O)(CH_2)_{0-3}NR^{16}R^{17}$ and $NHC(O)(CH_2)_{0-3}NR^{16}R^{17}$;

$R^{16}$ and $R^{17}$ are independently selected from hydrogen, $C_{1-6}$alkyl and $(CH_2)_{0-4}NR^{18}R^{19}$;

or $R^{16}$, $R^{17}$ and the nitrogen atom to which they are attached form a heteroaliphatic ring of 4 to 7 ring atoms, which ring may optionally contain 1 or 2 more heteroatoms selected from O or S or a group $S(O)$, $S(O)_2$, NH or $NC_{1-4}$alkyl, and which ring is optionally substituted by halogen, hydroxy, $C_{1-4}$alkyl or $C_{1-4}$alkoxy;

$R^{18}$ and $R^{19}$ are independently selected from hydrogen and $C_{1-6}$alkyl;

or $R^{18}$, $R^{19}$ and the nitrogen atom to which they are attached form a heteroaliphatic ring of 4 to 7 ring atoms, which ring may optionally contain 1 or 2 more heteroatoms selected from O or S or a group $S(O)$, $S(O)_2$, NH or $NC_{1-4}$alkyl, and which ring is optionally substituted by halogen, hydroxy, $C_{1-4}$alkyl or $C_{1-4}$alkoxy;

or a pharmaceutically acceptable salt thereof.

6. The compound as claimed in claim 5 of formula (Ib) or a pharmaceutically acceptable salt thereof:

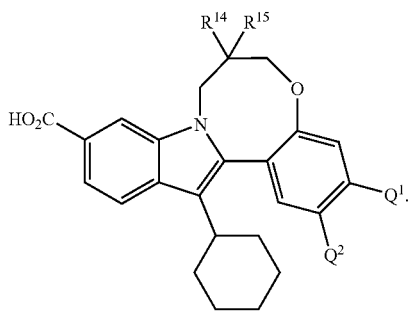

(Ib)

7. A pharmaceutical composition comprising a compound of formula (Ia) in association with a pharmaceutically acceptable carrier, wherein the compound of formula (Ia) is:

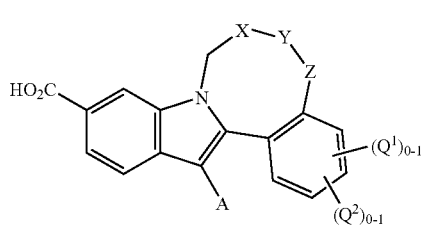

(Ia)

wherein
A is cyclohexyl, optionally substituted by halogen, hydroxy, $C_{1-4}$alkyl or $C_{1-4}$alkoxy;
$Q^1$ is halogen, hydroxy, $C_{1-6}$alkyl or $C_{1-6}$alkoxy;
$Q^2$ is absent;
W is —$CH_2$—;
X is —$CR^{14}R^{15}$—;
Y is —$CR^{14a}R^{15a}$—;
Z is O;
$R^{14}$, $R^{14a}$, $R^{15}$ and $R^{15a}$ are each independently selected from hydrogen, hydroxy, $C_{1-6}$alkyl, $C_{2-6}$alkenyl, $C_{1-6}$alkoxy, Het, $(CH_2)_{0-3}NR^{16}R^{17}$, $C(O)(CH_2)_{0-3}NR^{16}R^{17}$ and $NHC(O)(CH_2)_{0-3}NR^{16}R^{17}$;
$R^{16}$ and $R^{17}$ are independently selected from hydrogen, $C_{1-6}$alkyl, and $(CH_2)_{0-4}NR^{18}R^{19}$;
or $R^{16}$ and $R^{17}$, together with the nitrogen atom to which they are attached, form a heteroaliphatic ring of 4 to 7 ring atoms, which ring may optionally contain 1 or 2 more heteroatoms selected from O and S or a group selected from S(O), S(O)$_2$, NH and N$C_{1-4}$alkyl, and which ring is optionally substituted by halogen, hydroxy, $C_{1-4}$alkyl or $C_{1-4}$alkoxy;
$R^{18}$ and $R^{19}$ are independently selected from hydrogen and $C_{1-6}$alkyl;
or $R^{18}$ and $R^{19}$, together with the nitrogen atom to which they are attached, form a heteroaliphatic ring of 4 to 7 ring atoms, which ring may optionally contain 1 or 2 more heteroatoms selected from O and S or a group selected from S(O), S(O)$_2$, NH and N$C_{1-4}$alkyl, and which ring is optionally substituted by halogen, hydroxy, $C_{1-4}$alkyl or $C_{1-4}$alkoxy;
or a pharmaceutically acceptable salt thereof.

8. The compound as claimed in claim 5, wherein the compound is selected from the group consisting of:

N'-(11-carboxy-14-cyclohexyl-7,8-dihydro-6H-indolo[1,2-e][1,5]benzoxazocin-7-yl)-N,N-dimethylethane-1,2-diaminium bis(trifluoroacetate),
N-(11-carboxy-14-cyclohexyl-7,8-dihydro-6H-indolo[1,2-e][1,5]benzoxazocin-7-yl)-N,N',N'-trimethylethane-1,2-diaminium bis(trifluoroacetate),
N'-[(7R)-11-carboxy-14-cyclohexyl-7,8-dihydro-6H-indolo[1,2-e][1,5]benzoxazocin-7-yl]-N,N,N'-trimethylethane-1,2-diaminium bis(trifluoroacetate),
N'-[(7S)-11-carboxy-14-cyclohexyl-7,8-dihydro-6H-indolo[1,2-e][1,5]benzoxazocin-7-yl]-N,N,N'-trimethylethane-1,2-diaminium bis(trifluoroacetate),
(±)1-(11-carboxy-14-cyclohexyl-7,8-dihydro-6H-indolo[1,2-e][1,5]benzoxazocin-7-yl)-4-methylpiperazinediium bis(trifluoroacetate),
(±)-1-{2-[(11-carboxy-14-cyclohexyl-7,8-dihydro-6H-indolo[1,2-e][1,5]benzoxazocin-7-yl)(methyl)ammonio]ethyl}pyrrolidinium bis(trifluoroacetate),
N-(11-carboxy-14-cyclohexyl-3-fluoro-7,8-dihydro-6H-indolo[1,2-e][1,5]benzoxazocin-7-yl)-N,N',N'-trimethylethane-1,2-diaminium bis(trifluoroacetate),
(7R)-14-cyclohexyl-7-[[2-(dimethylamino)ethyl](methyl)amino]-3-fluoro-7,8-dihydro-6H-indolo[1,2-e][1,5]benzoxazocine-11-carboxylic acid,
(11-carboxy-14-cyclohexyl-7,8-dihydro-6H-indolo[1,2-e][1,5]benzoxazocin-7-yl)-N,N-dimethylmethanaminium trifluoroacetate,
3-chloro-14-cyclohexyl-7-[[2-(dimethylamino)ethyl](methyl)amino]-7,8-dihydro-6H-indolo[1,2-e][1,5]benzoxazocine-11-carboxylic acid,
14-cyclohexyl-7-{[2-(dimethylamino)ethyl]amino}-3-fluoro-7,8-dihydro-6H-indolo[1,2-e][1,5]benzoxazocine-11-carboxylic acid,
14-cyclohexyl-7-[[2-(dimethylamino)ethyl](ethyl)amino]-7,8-dihydro-6H-indolo[1,2-e][1,5]benzoxazocine-11-carboxylic acid,
14-cyclohexyl-7-[[2-(dimethylamino)ethyl](isopropyl)amino]-7,8-dihydro-6H-indolo[1,2-e][1,5]benzoxazocine-11-carboxylic acid,
14-cyclohexyl-7-{methyl[2-(methylamino)ethyl]amino}-7,8-dihydro-6H-indolo[1,2-e][1,5]benzoxazocine-11-carboxylic acid,
14-cyclohexyl-7-{methyl[2-(4-methylpiperazin-1-yl)ethyl]amino}-7,8-dihydro-6H-indolo[1,2-e][1,5]benzoxazocine-11-carboxylic acid,
14-cyclohexyl-7-[methyl(2-piperazin-1-ylethyl)amino]-7,8-dihydro-6H-indolo[1,2-e][1,5]benzoxazocine-11-carboxylic acid,
3-chloro-14-cyclohexyl-7-{[2-(dimethylamino)ethyl]amino}-7,8-dihydro-6H-indolo[1,2-e][1,5]benzoxazocine-11-carboxylic acid,
14-cyclohexyl-2-fluoro-7-(4-methylpiperazin-1-yl)-7,8-dihydro-6H-indolo[1,2-e][1,5]benzoxazocine-11-carboxylic acid,
14-cyclohexyl-7-{[3-(dimethylamino)propyl]amino}-7,8-dihydro-6H-indolo[1,2-e][1,5]benzoxazocine-11-carboxylic acid,
14-cyclohexyl-7-{[2-(dimethylamino)ethyl]amino}-2-fluoro-7,8-dihydro-6H-indolo[1,2-e][1,5]benzoxazocine-11-carboxylic acid,
7-[(2-aminoethyl)amino]-14-cyclohexyl-7,8-dihydro-6H-indolo[1,2-e][1,5]benzoxazocine-11-carboxylic acid,
14-cyclohexyl-7-(dimethylamino)-7,8-dihydro-6H-indolo[1,2-e][1,5]benzoxazocine-11-carboxylic acid,
14-cyclohexyl-7-(methylamino)-7,8-dihydro-6H-indolo[1,2-e][1,5]benzoxazocine-11-carboxylic acid, 7-amino-14-cyclohexyl-7,8-dihydro-6H-indolo[1,2-e][1,5]benzoxazocine-11-carboxylic acid, and 14-cyclohexyl-7-[(2-morpholin-4-ylethyl)amino]-7,8-dihydro-6H-indolo[1,2-e][1,5]benzoxazocine-11-carboxylic acid.

9. The pharmaceutical composition as claimed in claim 7, wherein the compound is selected from the group consisting of:

N'-(11-carboxy-14-cyclohexyl-7,8-dihydro-6H-indolo[1,2-e][1,5]benzoxazocin-7-yl)-N,N-dimethylethane-1,2-diaminium bis(trifluoroacetate), N-(11-carboxy-14-cyclohexyl-7,8-dihydro-6H-indolo[1,2-e][1,5]benzoxazocin-7-yl)-N,N',N'-trimethylethane-1,2-diaminium bis(trifluoroacetate), N'-[(7R)-11-carboxy-14-cyclohexyl-7,8-dihydro-6H-indolo[1,2-e][1,5]benzoxazocin-7-yl]-N,N,N'-trimethylethane-1,2-diaminium bis(trifluoroacetate), N'-[(7S)-11-carboxy-14-cyclohexyl-7,8-dihydro-6H-indolo[1,2-e][1,5]benzoxazocin-7-yl]-N,N,N'-trimethylethane-1,2-diaminium bis(trifluoroacetate), (±)1-(11-carboxy-14-cyclohexyl-7,8-dihydro-6H-indolo[1,2-e][1,5]benzoxazocin-7-yl)-4-methylpiperazinediium bis(trifluoroacetate), (±)-1-{2-[(11-carboxy-14-cyclohexyl-7,8-dihydro-6H-indolo[1,2-e][1,5]benzoxazocin-7-yl)(methyl)ammonio]ethyl}pyrrolidinium bis(trifluoroacetate), N-(11-carboxy-14-cyclohexyl-3-fluoro-7,8-dihydro-6H-indolo[1,2-e][1,5]benzoxazocin-7-yl)-N,N',N'-trimethylethane-1,2-diaminium bis(trifluoroacetate), (7R)-14-cyclohexyl-7-[[2-(dimethylamino)ethyl](methyl)amino]-3-fluoro-7,8-dihydro-6H-indolo[1,2-e][1,5]benzoxazocine-11-carboxylic acid, (11-carboxy-14-cyclohexyl-7,8-dihydro-6H-indolo[1,2-e][1,5]benzoxazocin-7-yl)-N,N-dimethylmethanaminium trifluoroacetate, 3-chloro-14-cyclohexyl-7-[[2-(dimethylamino)ethyl](methyl)amino]-7,8-dihydro-6H-indolo[1,2-e][1,5]benzoxazocine-11-carboxylic acid, 14-cyclohexyl-7-{[2-(dimethylamino)ethyl]amino}-3-fluoro-7,8-dihydro-6H-indolo[1,2-e][1,5]benzoxazocine-11-carboxylic acid, 14-cyclohexyl-7-[[2-(dimethylamino)ethyl](ethyl)amino]-7,8-dihydro-6H-indolo[1,2-e][1,5]benzoxazocine-11-carboxylic acid, 14-cyclohexyl-7-[[2-(dimethylamino)ethyl](isopropyl)amino]-7,8-dihydro-6H-indolo[1,2-e][1,5]benzoxazocine-11-carboxylic acid, 14-cyclohexyl-7-{methyl[2-(methylamino)ethyl]amino}-7,8-dihydro-6H-indolo[1,2-e][1,5]benzoxazocine-11-carboxylic acid, 14-cyclohexyl-7-{methyl[2-(4-methylpiperazin-1-yl)ethyl]amino}-7,8-dihydro-6H-indolo[1,2-e][1,5]benzoxazocine-11-carboxylic acid, 14-cyclohexyl-7-[methyl(2-piperazin-1-ylethyl)amino]-7,8-dihydro-6H-indolo[1,2-e][1,5]benzoxazocine-11-carboxylic acid, 3-chloro-14-cyclohexyl-7-{[2-(dimethylamino)ethyl]amino}-7,8-dihydro-6H-indolo[1,2-e][1,5]benzoxazocine-11-carboxylic acid, 14-cyclohexyl-2-fluoro-7-(4-methylpiperazin-1-yl)-7,8-dihydro-6H-indolo[1,2-e][1,5]benzoxazocine-11-carboxylic acid, 14-cyclohexyl-7-{[3-(dimethylamino)propyl]amino}-7,8-dihydro-6H-indolo[1,2-e][1,5]benzoxazocine-11-carboxylic acid, 14-cyclohexyl-7-{[2-(dimethylamino)ethyl]amino}-2-fluoro-7,8-dihydro-6H-indolo[1,2-e][1,5]benzoxazocine-11-carboxylic acid, 7-[(2-aminoethyl)amino]-14-cyclohexyl-7,8-dihydro-6H-indolo[1,2-e][1,5]benzoxazocine-11-carboxylic acid, 14-cyclohexyl-7-(dimethylamino)-7,8-dihydro-6H-indolo[1,2-e][1,5]benzoxazocine-11-carboxylic acid, 14-cyclohexyl-7-(methylamino)-7,8-dihydro-6H-indolo[1,2-e][1,5]benzoxazocine-11-carboxylic acid, 7-amino-14-cyclohexyl-7,8-dihydro-6H-indolo[1,2-e][1,5]benzoxazocine-11-carboxylic acid, and 14-cyclohexyl-7-[(2-morpholin-4-ylethyl)amino]-7,8-dihydro-6H-indolo[1,2-e][1,5]benzoxazocine-11-carboxylic acid.

10. The compound as claimed in claim 5, wherein the compound is N'-[(7R)-11-carboxy-14-cyclohexyl-7,8-dihydro-6H-indolo[1,2-e][1,5]benzoxazocin-7-yl]-N,N,N'-trimethylethane-1,2-diaminium bis(trifluoroacetate).

11. The pharmaceutical composition as claimed in claim 7, wherein the compound is N'-[(7R)-11-carboxy-14-cyclohexyl-7,8-dihydro-6H-indolo[1,2-e][1,5]benzoxazocin-7-yl]-N,N,N'-trimethylethane-1,2-diaminium bis(trifluoroacetate).

12. The compound as claimed in claim 5, wherein the compound is N'-[(7S)-11-carboxy-14-cyclohexyl-7,8-dihydro-6H-indolo[1,2-e][1,5]benzoxazocin-7-yl]-N,N,N'-trimethylethane-1,2-diaminium bis(trifluoroacetate).

13. The pharmaceutical composition as claimed in claim 7, wherein the compound is N'-[(7S)-11-carboxy-14-cyclohexyl-7,8-dihydro-6H-indolo[1,2-e][1,5]benzoxazocin-7-yl]-N,N,N'-trimethylethane-1,2-diaminium bis(trifluoroacetate).

14. The compound as claimed in claim 5, wherein the compound is (7R)-14-cyclohexyl-7-[[2-(dimethylamino)ethyl](methyl)amino]-3-fluoro-7,8-dihydro-6H-indolo[1,2-e][1,5]benzoxazocine-11-carboxylic acid.

15. The pharmaceutical composition as claimed in claim 7, wherein the compound is (7R)-14-cyclohexyl-7-[[2-(dimethylamino)ethyl](methyl)amino]-3-fluoro-7,8-dihydro-6H-indolo[1,2-e][1,5]benzoxazocine-11-carboxylic acid.

16. The compound as claimed in claim 5, wherein the compound is 14-cyclohexyl-7-{[2-(dimethylamino)ethyl]amino}-3-fluoro-7,8-dihydro-6H-indolo[1,2-e][1,5]benzoxazocine-11-carboxylic acid.

17. The pharmaceutical composition as claimed in claim 7, wherein the compound is 14-cyclohexyl-7-{[2-(dimethylamino)ethyl]amino}-3-fluoro-7,8-dihydro-6H-indolo[-1,2-e][1,5]benzoxazocine-11-carboxylic acid.

18. The compound as claimed in claim 6, wherein $Q^1$ is absent.

19. The compound as claimed in claim 18, wherein $R^{14}$ is $NR^{16}R^{17}$.

20. The compound as claimed in claim 19, wherein $NR^{16}R^{17}$ is selected from the group consisting of:

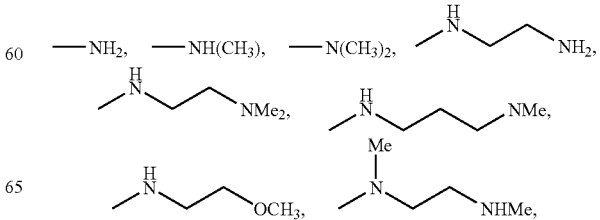

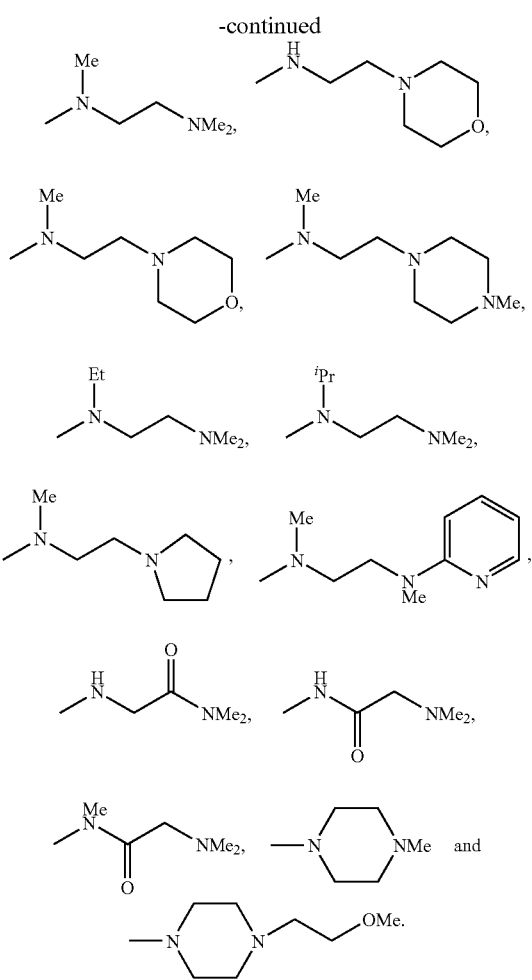

21. The compound as claimed in claim 20, wherein $R^{15}$ is hydrogen.

22. The pharmaceutical composition comprising the compound of claim 21 and a pharmaceutically acceptable carrier.

23. A compound selected from the group consisting of:
(7R)-14-cyclohexyl-7-[[2-(dimethylamino)ethyl](methyl)amino]-7,8-dihydro-6H-indolo[1,2-e][1,5]benzoxazocine-11-carboxylic acid; and
(7S)-14-cyclohexyl-7-[[2-(dimethylamino)ethyl](methyl)amino]-7,8-dihydro-6H-indolo[1,2-e][1,5]benzoxazocine-11-carboxylic acid;
or a pharmaceutically acceptable salt thereof.

24. The compound of claim 23, wherein said compound is N'-[(7R)-11-carboxy-14-cyclohexyl-7,8-dihydro-6H-indolo[1,2-e][1,5]benzoxazocin-7-yl]-N,N,N'-trimethylethane-1,2-diaminium bis(trifluoroacetate) or a pharmaceutically acceptable salt thereof.

25. The compound of claim 23, wherein said compound is (7R)-14-cyclohexyl-7-[[2-(dimethylamino)ethyl](methyl)amino]-7,8-dihydro-6H-indolo[1,2-e][1,5]benzoxazocine-11-carboxylic acid or a pharmaceutically acceptable salt thereof.

26. The compound of claim 23, wherein said compound is N'-[(7S)-11-carboxy-14-cyclohexyl-7,8-dihydro-6H-indolo[1,2-e][1,5]benzoxazocin-7-yl]-N,N,N'-trimethylethane-1,2-diaminium bis(trifluoroacetate) or a pharmaceutically acceptable salt thereof.

27. The compound of claim 23, wherein said compound is (7S)-14-cyclohexyl-7-[[2-(dimethylamino)ethyl](methyl)amino]-7,8-dihydro-6H-indolo[1,2-e][1,5]benzoxazocine-11-carboxylic acid or a pharmaceutically acceptable salt thereof.

28. The pharmaceutically composition comprising the compound of claim 24 and pharmaceutically acceptable carrier.

29. The pharmaceutically composition comprising the compound of claim 25 and pharmaceutically acceptable carrier.

30. The pharmaceutically composition comprising the compound of claim 26 and pharmaceutically acceptable carrier.

31. The pharmaceutically composition comprising the compound of claim 27 and pharmaceutically acceptable carrier.

* * * * *